United States Patent
Krishnadath et al.

(10) Patent No.: US 10,280,218 B2
(45) Date of Patent: May 7, 2019

(54) ANTIBODIES BINDING TO BMP4, AND USES THEREOF

(71) Applicant: ACADEMISCH MEDISCH CENTRUM, Amsterdam (NL)

(72) Inventors: Kausilia Krishnawatie Krishnadath, Overveen (NL); Silvia Calpe, Amsterdam (NL)

(73) Assignee: ACADEMISCH MEDISCH CENTRUM, Amsterdam (NL)

( * ) Notice: Subject to any disclaimer, the term of this patent is extended or adjusted under 35 U.S.C. 154(b) by 0 days.

(21) Appl. No.: 15/511,617

(22) PCT Filed: Sep. 16, 2015

(86) PCT No.: PCT/EP2015/071270
§ 371 (c)(1),
(2) Date: Mar. 15, 2017

(87) PCT Pub. No.: WO2016/042050
PCT Pub. Date: Mar. 24, 2016

(65) Prior Publication Data
US 2018/0162932 A1    Jun. 14, 2018

(30) Foreign Application Priority Data
Sep. 16, 2014    (WO) ................ PCT/NL2014/050632

(51) Int. Cl.
| | |
|---|---|
| C07K 16/22 | (2006.01) |
| C07K 16/00 | (2006.01) |
| C07K 16/18 | (2006.01) |
| A61K 33/24 | (2019.01) |
| A61K 35/00 | (2006.01) |

(52) U.S. Cl.
CPC .............. *C07K 16/22* (2013.01); *A61K 33/24* (2013.01); *A61K 35/00* (2013.01); *C07K 2317/22* (2013.01); *C07K 2317/31* (2013.01); *C07K 2317/33* (2013.01); *C07K 2317/34* (2013.01); *C07K 2317/35* (2013.01); *C07K 2317/569* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| | | |
|---|---|---|
| EP | 2047862 A1 | 4/2009 |
| WO | 2008/030611 A2 | 3/2008 |

OTHER PUBLICATIONS

Lawrence et al. (1999, Anti-Cancer Drugs 10:655-661).*
Hanauske et al. (1995, Investigational New Drugs 13: 43-49).*
Kornblith et al. (2003, Anticancer Research 23:543-548).*
Depenbrock et al. (1997, European Journal of Cancer 33:2404-2410).*
Gabrielson et al. (1999, Clinical Cancer Research 5:1638-1641).*
Georgoulias (2002, Current Medicinal Chemistry 9:869-877).*
Burris III et al. (1992, Journal of the National Cancer Institute 84:1816-1820).*
Martin et al. (1994, Journal of the National Cancer Institute 86:608-613).*
Izbicka et al. (1999, Investigational New Drugs 16:221-225).*
McIntyre et al. (2015, Bioassays 37:909-920).*
International Search Report and Written Opinion of International Patent Application No. PCT/EP2015/071270 dated Mar. 7, 2016.
Bhattacherjee, Aritra et al., "Bone Morphogenetic Protein 4 Mediates Estrogen-Regulated Sensory Axon Plasticity in the Adult Female Reproductive Tract", Journal of Neuroscience, Jan. 16, 2013, pp. 1050-10611, vol. 33, No. 3.
Kwak, Young-Don et al., "Secreted type of amyloid precursor protein induces glial differentiation by stimulating the BMP/Smad signaling pathway", Biochemical and Biophysical Research Communications, Apr. 13, 2014, pp. 394-399, vol. 447, No. 3.
Khurana, Satish et al., "SMAD Signaling Regulates CXCL12 Expression in the Bone Marrow Niche, Affecting Homing and Mobilization of Hematopoietic Progenitors", Stem Cells, Nov. 14, 2014, pp. 3012-3022, vol. 32, No. 11.
Weber, Franz E. et al., "Deletion Mutants of BMP Folding Variants Act as BMP Antagonists and Are Efficient Inhibitors for Heterotopic Ossification", Journal of Bone and Mineral Research, Blackwell Science, Inc., Dec. 1, 2003, pp. 2142-2151, vol. 18, No. 12.
Deng, Haiyun et al., "Overexpression of bone morphogenetic protein 4 enhances the invasiveness of Smad4-deficient human colorectal cancer cells", Cancer Letters, Aug. 28, 2009, pp. 220-231, vol. 281, No. 2.
Voorneveld, Philip W. et al., "Loss of SMAD4 Alters BMP Signaling to Promote Colorectal Cancer Cell Metastasis via Activation of Rho and ROCK", Gastroenterology, Jul. 1, 2014, pp. 196-208, vol. 147, No. 1.

* cited by examiner

*Primary Examiner* — Elizabeth C. Kemmerer
(74) *Attorney, Agent, or Firm* — McBee Moore Woodward & Vanik IP, LLC; Susan McBee; Chester Moore

(57) ABSTRACT

The present invention relates to antibody which binds to an epitope located within the BMPR1 binding region of BMP4.

12 Claims, 31 Drawing Sheets
Specification includes a Sequence Listing.

| | 1 | 2 | 3 | 4 | 5 | 6 | 7 | 8 | 9 | 10 | 11 | 12 |
|---|---|---|---|---|---|---|---|---|---|---|---|---|
| A | 1.186 | 1.32 | 0.951 | 1.286 | 1.303 | 1.24 | 0.537 | 1.092 | 0.892 | 0.064 | 0.043 | 0.034 |
| B | 0.917 | 1.193 | 0.966 | 1.356 | 0.926 | 1.341 | 0.121 | 0.209 | 0.959 | 0.161 | 0.571 | 0.101 |
| C | 0.931 | 1.196 | 0.972 | 1.407 | 1.296 | 1.33 | 0.757 | 1.22 | 1.228 | 1.125 | 0.059 | 0.522 |
| D | 1.182 | 1.196 | 1.048 | 0.564 | 0.536 | 1.454 | 0.739 | 1.133 | 0.055 | 0.641 | 0.431 | 0.172 |
| E | 1.146 | 0.813 | 1.353 | 1.29 | 1.441 | 0.807 | 0.903 | 1.028 | 0.872 | 0.16 | 0.047 | 0.497 |
| F | 1.064 | 0.707 | 1.319 | 1.235 | 0.996 | 0.793 | 0.801 | 0.032 | 0.185 | 0.099 | 0.04 | 0.905 |
| G | 0.845 | 0.891 | 1.262 | 0.968 | 1.154 | 1.455 | 0.715 | 0.583 | 0.405 | 1.015 | 0.283 | 0.372 |
| H | 1.147 | 1.347 | 0.945 | 1.336 | 1.06 | 0.044 | 0.692 | 0.599 | 0.516 | 0.535 | 0.494 | 0.055 |
| | | | | | | neg. | | | | | | neg. |

Figure 17 (A and B)

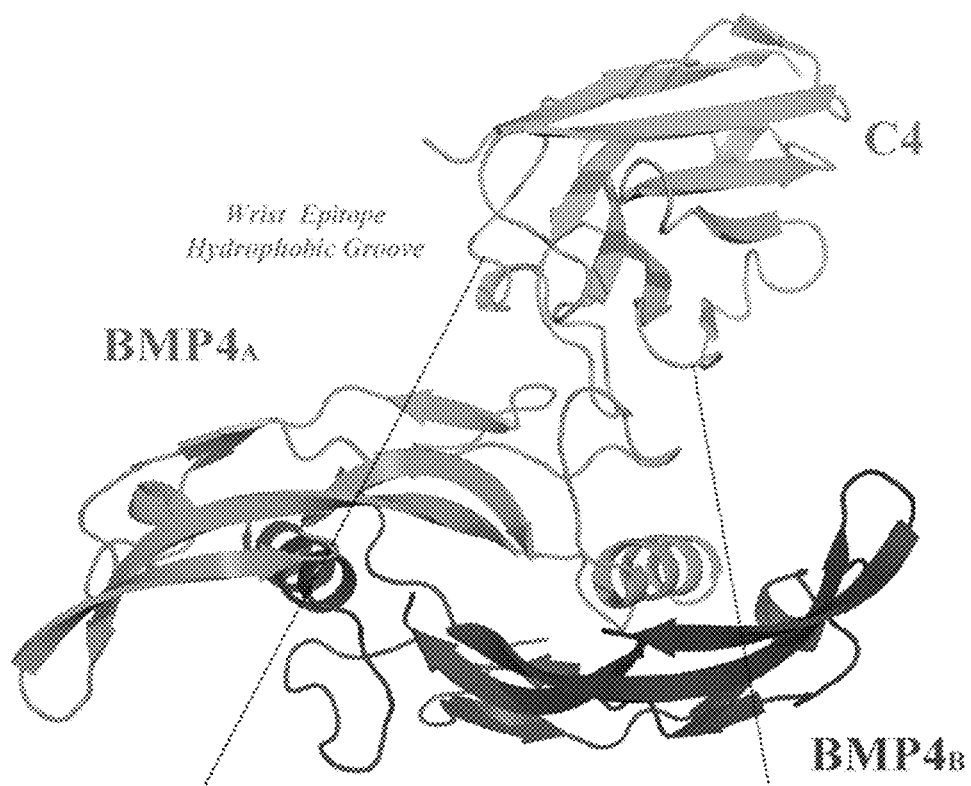
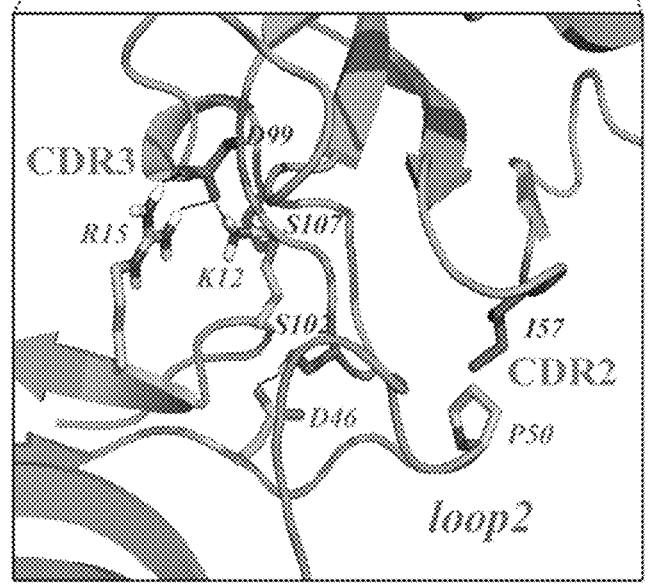
FIG. 19

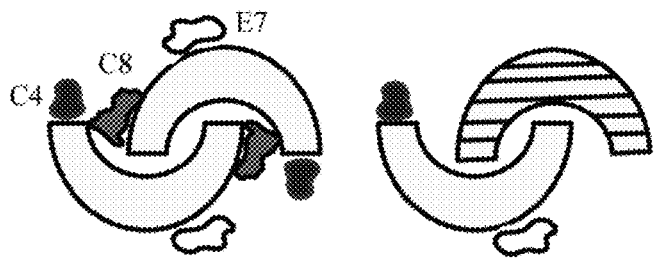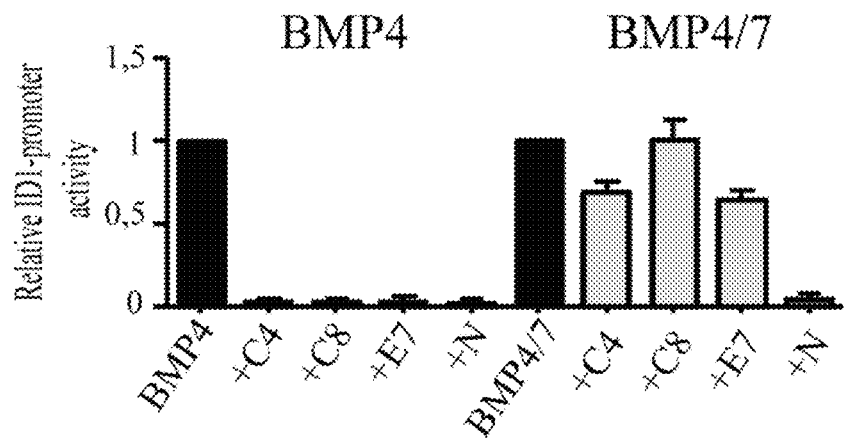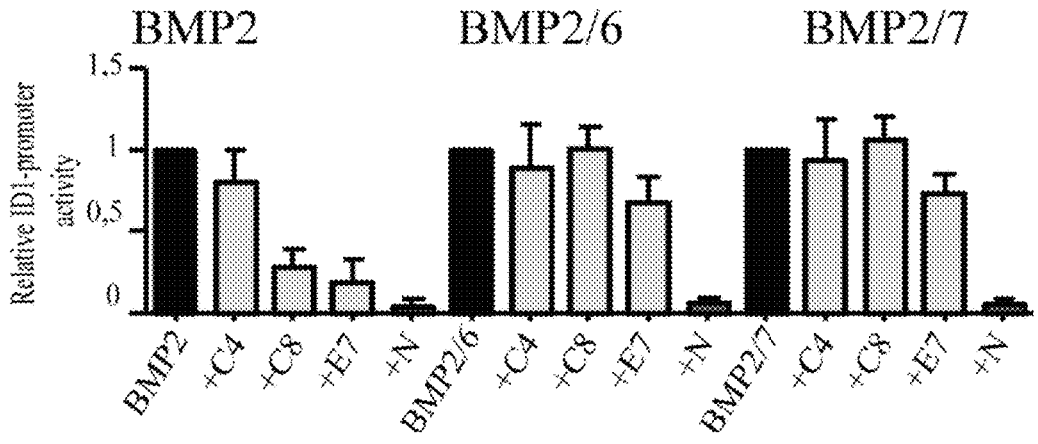
FIG. 27

SEQUENCE LISTING

```
<160> NUMBER OF SEQ ID NOS: 21

<210> SEQ ID NO 1
<211> LENGTH: 114
<212> TYPE: PRT
<213> ORGANISM: Artificial Sequence
<220> FEATURE:
<223> OTHER INFORMATION: BMP4

<400> SEQUENCE: 1

Lys His His Ser Gln Arg Ala Arg Lys Lys Asn Lys Asn Cys Arg Arg
1               5                   10                  15

His Ser Leu Tyr Val Asp Phe Ser Asp Val Gly Trp Asn Asp Trp Ile
            20                  25                  30

Val Ala Pro Pro Gly Tyr Gln Ala Phe Tyr Cys His Gly Asp Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Ser Ile Pro Lys Ala Cys Cys Val
65                  70                  75                  80

Pro Thr Glu Leu Ser Ala Ile Ser Met Leu Tyr Leu Asp Glu Tyr Asp
                85                  90                  95

Lys Val Val Leu Lys Asn Tyr Gln Glu Met Val Val Glu Gly Cys Gly
            100                 105                 110

Cys Arg

<210> SEQ ID NO 2
<211> LENGTH: 8
<212> TYPE: PRT
<213> ORGANISM: Artificial Sequence
<220> FEATURE:
<223> OTHER INFORMATION: CDR1

<400> SEQUENCE: 2

Gly Arg Thr Phe Ser Thr Tyr Ala
1               5

<210> SEQ ID NO 3
<211> LENGTH: 8
<212> TYPE: PRT
<213> ORGANISM: Artificial Sequence
```

```
<220> FEATURE:
<223> OTHER INFORMATION: CDR2

<400> SEQUENCE: 3

Ser Lys Gly Gly Gly Ile Thr Tyr
1               5

<210> SEQ ID NO 4
<211> LENGTH: 14
<212> TYPE: PRT
<213> ORGANISM: Artificial Sequence
<220> FEATURE:
<223> OTHER INFORMATION: CDR3

<400> SEQUENCE: 4

Asp Pro Val Ser Ser Val Ala Lys Ser Pro Val Ala Tyr Pro
1               5                   10

<210> SEQ ID NO 5
<211> LENGTH: 8
<212> TYPE: PRT
<213> ORGANISM: Artificial Sequence
<220> FEATURE:
<223> OTHER INFORMATION: CDR1 of C8

<400> SEQUENCE: 5

Gly Arg Thr Phe Arg Ile Asn Asp
1               5

<210> SEQ ID NO 6
<211> LENGTH: 7
<212> TYPE: PRT
<213> ORGANISM: Artificial Sequence
<220> FEATURE:
<223> OTHER INFORMATION: CDR2 of C8

<400> SEQUENCE: 6

Thr Ser Gly Gly Asn Thr Asn
1               5

<210> SEQ ID NO 7
<211> LENGTH: 14
<212> TYPE: PRT
<213> ORGANISM: Artificial Sequence
<220> FEATURE:
<223> OTHER INFORMATION: CDR3 of C8

<400> SEQUENCE: 7

Asp Gly Leu Arg Phe Asp Ser Thr Arg Tyr Arg Pro Phe Asp
1               5                   10

<210> SEQ ID NO 8
<211> LENGTH: 8
<212> TYPE: PRT
<213> ORGANISM: Artificial Sequence
<220> FEATURE:
<223> OTHER INFORMATION: CDR1 of E7

<400> SEQUENCE: 8

Gly Ser Ile Arg Gly Phe Val Ala
1               5

<210> SEQ ID NO 9
<211> LENGTH: 6
<212> TYPE: PRT
<213> ORGANISM: Artificial Sequence
<220> FEATURE:
```

```
<223> OTHER INFORMATION: CDR2 of E7

<400> SEQUENCE: 9

Thr Asn Gly Gly Thr Leu
1               5

<210> SEQ ID NO 10
<211> LENGTH: 9
<212> TYPE: PRT
<213> ORGANISM: Artificial Sequence
<220> FEATURE:
<223> OTHER INFORMATION: CDR3 of E7

<400> SEQUENCE: 10

Arg Gln Ile Gly Ala Ser Gly Tyr Asp
1               5

<210> SEQ ID NO 11
<211> LENGTH: 124
<212> TYPE: PRT
<213> ORGANISM: Artificial Sequence
<220> FEATURE:
<223> OTHER INFORMATION: C4

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Ala Met Gly Trp Phe Arg Gln Ala Pro Gly Lys Glu Arg Glu Phe Val
        35                  40                  45

Ala Ala Ile Ser Lys Gly Gly Gly Ile Thr Tyr Tyr Ser Asp Ser Val
    50                  55                  60

Arg Gly Arg Phe Thr Ile Ser Lys Glu Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Val Ser Ser Val Ala Lys Ser Pro Val Ala Tyr Pro
            100                 105                 110

Tyr Trp Gly Gln Gly Thr Gln Val Thr Val Ser Ser
        115                 120

<210> SEQ ID NO 12
<211> LENGTH: 123
<212> TYPE: PRT
<213> ORGANISM: Artificial Sequence
<220> FEATURE:
<223> OTHER INFORMATION: C8

<400> SEQUENCE: 12

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Arg Ile Asn
            20                  25                  30

Asp Met Gly Trp Tyr Arg Gln Ala Pro Gly Lys Ser Arg Asp Met Val
        35                  40                  45

Ala Arg Ile Thr Ser Gly Gly Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80
```

```
Gln Met Asn Ser Leu Lys Pro Glu Asp Thr Ala Val Tyr Tyr Cys Asn
            85                  90                  95

Ala Asp Gly Leu Arg Phe Asp Ser Thr Arg Tyr Arg Pro Phe Asp Ser
        100                 105                 110

Trp Gly Gln Gly Thr Gln Val Thr Val Ser Ser
        115                 120
```

<210> SEQ ID NO 13

<400> SEQUENCE: 13

000

<210> SEQ ID NO 14
<211> LENGTH: 117
<212> TYPE: PRT
<213> ORGANISM: Artificial Sequence
<220> FEATURE:
<223> OTHER INFORMATION: E7

<400> SEQUENCE: 14

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Arg Gly Phe Val
            20                  25                  30

Ala Met Ala Trp Tyr Arg Gln Ala Pro Gly Lys Gln Arg Glu Trp Val
        35                  40                  45

Ala Thr Val Thr Asn Gly Gly Thr Leu Tyr Gly Asp Ser Val Lys Gly
    50                  55                  60

Arg Phe Thr Gly Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Leu
                85                  90                  95

Arg Gln Ile Gly Ala Ser Gly Tyr Asp Tyr Trp Gly Gln Gly Thr Gln
            100                 105                 110

Val Thr Val Ser Ser
        115
```

<210> SEQ ID NO 15
<211> LENGTH: 114
<212> TYPE: PRT
<213> ORGANISM: Artificial Sequence
<220> FEATURE:
<223> OTHER INFORMATION: BMP2

<400> SEQUENCE: 15

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
```

Cys Arg

<210> SEQ ID NO 16
<211> LENGTH: 115
<212> TYPE: PRT
<213> ORGANISM: Artificial Sequence
<220> FEATURE:
<223> OTHER INFORMATION: BMP5

<400> SEQUENCE: 16

Ser Val Gly Asp Tyr Asn Thr Ser Glu Gln Lys Gln Ala Cys Lys Lys
1               5                   10                  15

His Glu Leu Tyr Val Ser Phe Arg Asp Leu Gly Trp Gln Asp Trp Ile
            20                  25                  30

Ile Ala Pro Glu Gly Tyr Ala Ala Phe Tyr Cys Asp Gly Glu Cys Ser
        35                  40                  45

Phe Pro Leu Asn Ala His Met Asn Ala Thr Asn His Ala Ile Val Gln
50                  55                  60

Thr Leu Val His Leu Met Phe Pro Asp His Val Pro Lys Pro Cys Cys
65                  70                  75                  80

Ala Pro Thr Lys Leu Asn Ala Ile Ser Val Leu Tyr Phe Asp Asp Ser
                85                  90                  95

Ser Asn Val Ile Leu Lys Lys Tyr Arg Asn Met Val Val Arg Ser Cys
            100                 105                 110

Gly Cys His
        115

<210> SEQ ID NO 17
<211> LENGTH: 139
<212> TYPE: PRT
<213> ORGANISM: Artificial Sequence
<220> FEATURE:
<223> OTHER INFORMATION: BMP6

<400> SEQUENCE: 17

Ser Ala Ser Ser Arg Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
            20                  25                  30

Glu Leu Lys Thr Ala Cys Arg Lys His Glu Leu Tyr Val Ser Phe Gln
        35                  40                  45

Asp Leu Gly Trp Gln Asp Trp Ile Ile Ala Pro Lys Gly Tyr Ala Ala
50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
130                 135

<210> SEQ ID NO 18
<211> LENGTH: 139
<212> TYPE: PRT

```
<213> ORGANISM: Artificial Sequence
<220> FEATURE:
<223> OTHER INFORMATION: BMP7

<400> SEQUENCE: 18

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65              70                  75                  80

Ala Thr Asn His Ala Ile Val Gln Thr Leu Val His Phe Ile Asn Pro
            85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
        130                 135

<210> SEQ ID NO 19
<211> LENGTH: 14
<212> TYPE: PRT
<213> ORGANISM: Artificial Sequence
<220> FEATURE:
<223> OTHER INFORMATION: hBMP2

<400> SEQUENCE: 19

Gln Ala Lys His Lys Gln Arg Lys Arg Leu Lys Ser Ser Cys
1               5                   10

<210> SEQ ID NO 20
<211> LENGTH: 16
<212> TYPE: PRT
<213> ORGANISM: Artificial Sequence
<220> FEATURE:
<223> OTHER INFORMATION: hBMP4

<400> SEQUENCE: 20

Ser Pro Lys His His Ser Gln Arg Ala Arg Lys Lys Asn Lys Asn Cys
1               5                   10                  15

<210> SEQ ID NO 21
<211> LENGTH: 6
<212> TYPE: PRT
<213> ORGANISM: Artificial Sequence
<220> FEATURE:
<223> OTHER INFORMATION: hDELTABMP4

<400> SEQUENCE: 21

Lys Lys Asn Lys Asn Cys
1               5
```

ANTIBODIES BINDING TO BMP4, AND USES THEREOF

FIELD OF THE INVENTION

The present invention is in the field of biology, biotechnology and medicine and relates to anti-BMP4 antibodies and pharmaceutical compositions comprising an anti-BMP4 antibody for use in the treatment of SMAD4 deficient cancer. The invention further relates to anti-BMP4 antibodies binding to a conformational epitope located within the BMPR1a binding site of BMP4 and pharmaceutical uses thereof. The invention also relates to single-domain antibodies.

BACKGROUND OF THE INVENTION

Smad4 is a component of the Smad pathway that is involved in signal transduction in the TGF-β pathway (Levy, L and Hill, C. S., Molec. Cell. Biol. 25:8108-8125 (2005); Fukuchi, M. et al., Cancer 95:737-743 (2002)). This gene, also known as dpc4 (for "decreased in pancreatic carcinoma"), appears to be a tumor suppressor gene, and a decrease in smad4 expression has been observed in a variety of primary carcinomas, including pancreatic carcinomas (Luttges, J. et al., Am. J. Pathol. 158:1677-1683 (2001); Subramanian, G. et al., Cancer Res. 64:5200-5211 (2004)), esophageal carcinomas (Fukuchi, M. et al., Cancer 95:737-743 (2002), cervical carcinomas (Maliekal, T. T. et al., Oncogene 22:4889-4897 (2003), and other primary human cancers (Iacobuzio-Donahue, C. A. et al., Clin. Canc. Res. 10:1597-1604 (2004), as well as in cell line cancer models including of pancreatic cancers (Lohr, M. et al., Cancer Res. 61:550-555 (2001); Yasutome, M. et al., Clin. Exp. Metastasis 22:461-473 (2005)), and of colon cancers (Levy, L., and Hill, C. S., Molec. Cell. Biol. 25:8108-8125 (2005)). A reduced expression of smad4 in tumors has been associated with poor prognosis for patient survival, particularly in patients with smad4-deficient pancreatic adenocarcinomas (Liu, F., Clin. Cancer Res. 7:3853-3856 (2001); Tascilar, M. et al., Clin. Cancer Res. 7:4115-4121 (2001); Toga, T. et al., Anticancer Res. 24:1173-1178 (2004)). The mechanism of the tumor suppressive activity of the smad4 gene product is poorly understood, but it is thought that it may act as a "switch" regulating the growth-suppressive and growth-activating activities of certain components of the TGF-β signaling pathway (for reviews, see Akhurst, A. J., J. Clin. Invest. 109:1533-1536 (2002); Bachman, K. E., and Park, B. H., Curr. Opin. Oncol. 17:49-54 (2004); Bierie, B., and Moses, H. L., Nature Rev. Cancer 6:506-520 (2006)). Smad4 deficient tumors often respond less well to chemotherapy.

Therefore, there is a need to provide an alternative or improved therapy for treating SMAD4 deficient cancer.

Bone morphogenetic proteins (BMPs) are growth factors that belong the TGFβ superfamily. They comprise of around 20 members, classified into distinct subfamilies, depending on their sequence homology and functionality. BMP-2/BMP-4 and BMP-5/BMP-6/BMP-7 form subgroups that have been extensively studied and demonstrated to have osteogenic capacities (Wilson et al. 2013).

Although first identified by their capacity to support bone and cartilage development (Wozney et al. 1988), BMPs are involved in organ development and regulate homeostasis in a wide array of tissues. Besides their homeostatic function in normal embryonic and adult tissues, BMPs also play important roles in the pathology of several diseases, such as obesity, diabetes and cancer (Bragdon et al. 2011). They mediate their function by controlling differentiation, proliferation, cell growth and apoptosis at the intra and intercellular level. BMPs are secreted to the extracellular matrix as mature active dimers and can act on the target cells by binding to two molecules of type I (BMPR1a or BMPR1b) and two molecules of type II (BMPR2 or ActR2) Serine/Threonine kinase receptors, thereby forming an hexameric complex that will initiate the intracellular signaling cascade (Miyazono, Kamiya, and Morikawa 2010). Depending on the presence or absence of pre-formed BMPR complexes, the signaling will be mediated via the SMAD family following a defined canonical pathway or by less defined non-canonical intracellular effectors (Mueller and Nickel 2012). Translocation to the nucleus of these transcription factors, will initiate transcription of BMP-target genes.

The significance of the critical role of BMPs in many biological processes is perhaps best manifested by the presence of a multi-level regulation of BMP function. At the transcriptional level, control of BMP expression can be mediated by gene methylation (Kimura et al. 2008; Wen et al. 2006; Zhang et al. 2007), or by specific microRNAs, such as microRNA196b and mIR20b (Braig et al. 2010). At the cytosol, the presence of the smad inhibitors (iSMADs), that compete for receptor or SMAD binding such as Smad 6 and 7 can also attenuate BMP function. Other inhibitors such as protein phosphatases (PP1 and PP2) dilute the strength of BMP signal by dephosphorylating both the receptors and the pSMADs (Wrighton, Lin, and Feng 2009). BMP signaling can also be modulated by the presence of extracellular molecules that bind to BMP, inhibiting or enhancing BMP activity (Zakin and De Robertis 2010). Co-receptors potentiate BMP function by enhancing ligand binding whereas pseudoreceptors inhibit BMP signaling by sequestering BMPR2 and rendering it unavailable for BMP ligands (Onichtchouk et al. 1999). Another well studied group of extracellular BMP modulators is the Cysteine-knot group of BMP antagonists, which bind distinct BMPs with high affinities and prevent their interaction with the receptors. Depending on the structure (size of the cysteine knot) they are divided into three groups: the DAN family (Gremlin, Sclerostin), the twisted gastrulation (Tsg), and chordin and noggin.

The interplay between BMPs and their antagonists is crucial in determining their effects in development and in adult tissues. For several years the role of specific BMPs has been addressed in many nondiseased and diseased tissues. One of the most intriguing and poorly understood BMPs is BMP4. BMP4 seems to have opposing roles in cancers (Kallioniemi 2012). In certain malignancies high levels of BMP4 seems to be associated with less malignant features while in, for instance, breast and colon cancers BMP4 non canonical signaling was involved in EMT and metastatic behavior (Guo, Huang, and Gong 2012; Voorneveld et al. 2014). A more recent observation is the role of BMP4 on cell differentiation and epithelial metaplasia (Mari et al. 2014). To resolve the actual role of BMPs in different disorders it is required to study their specific function in diverse disease models.

The option of regulating BMP signaling at the extracellular receptor level is highly attractive, since extracellular regulation of signaling can be easily targeted to manipulate its function. Therefore, several natural antagonists have been tested to study the BMP effects on cellular processes. This approach is, however, hampered by the fact that the natural BMP inhibitors are limited to study the effect of the individual BMPs due to several factors intrinsic to their mechanism of action. In general, natural BMP antagonists are non selective in nature and modulate signaling of not only different BMPs, but also other members of the TGFB family, such as activins and nodal (Balemans and Van Hul 2002). Thus, studies using natural antagonists might not reflect results from the inactivation of individual BMPs. Moreover, the multi-target antagonism is not limited to the TGFB family members, as most antagonists can also interfere with wnt signaling pathways which indirectly affect BMP function (Yanagita 2005). Also several mechanisms of action have been described for some of these antagonists, rendering these molecules highly unspecific at inhibiting BMP function. For instance, Chordin possesses BMP-independent functions due to its binding to cell surface proteins and, thus, altering of cellular integrity (Chen et al. 2004). In some cases, BMP modulators possess such opposing modes of regulation, that they can act both as anti- or pro-BMP function, like in the case of Tsg and CV2 (Gazzerro and Canalis 2006; Oelgeschläger et al. 2000; Rentzsch et al. 2006; Wills, Harland, and Khokha 2006). Another complicating factor is that their activity is in turn tightly regulated by extracellular factors, including other BMP antagonists and other proteins, such as the metalloproteases Xolloid and Tolloid (Piccolo et al. 1997). Thus, if the expression of antagonists overlaps, it might result in activation of BMP signaling instead of inhibition. Therefore, these natural antagonists are ill-suited to inhibit or to define the individual action of each BMP and to study the role of specific BMPs in different disorders.

There are also antibodies available which bind to BMP4, anti-BMP4 R&D (Clone 66119, Mouse IgG2B, MAB757) and anti-BMP4 Abcam (Rabbit polyclonal, ab39973). In WO2008030611 antibodies are described which have an affinity for BMP2 and BMP4. Disadvantage of existing anti-BMP4 antibodies is that they have a low affinity for BMP4, are less capable of inhibiting BMP4 signaling and/or functionally blocking BMP4 in-vivo. It is an objective of the invention to overcome one or more of these disadvantages.

SUMMARY OF THE INVENTION

The invention is based on the surprising finding that by reducing BMP4 signaling using anti-BMP4 antibodies, growth of SMAD4 deficient tumor cells was reduced in mice. The invention therefore provides an antibody binding to BMP4 for use in the treatment of a SMAD4 deficient tumor, as well as a use of an antibody binding to BMP4 for the preparation of a medicament for the treatment of a SMAD4 deficient tumor. In FIGS. 37 and 38 herein it is shown that anti-BMP4 antibodies (C4C4 and C8C8) inhibited SMAD4 deficient tumor growth to the same extent as cisplatinum. This was very surprising, as it was shown by Lombardo et al. 2011, GASTROENTEROLOGY 2011; 140: 297-309, that treatment of patient-derived SMAD4 deficient tumors with BMP4 antagonist Noggin generated tumors that grew faster instead of slower (shown in FIG. 6 of Lombardo et al.). Hence, it was expected that counteracting BMP4 was not a suitable option for treating SMAD4 deficient tumors. In WO2008030611, antibodies are disclosed which bind to BMP4 and BMP2 (see Table 1). In example 14 of WO2008030611 it is hypothetically suggested that a direct in vivo effect on tumor growth may be obtained using toxin conjugated antibodies in mice. This example thus suggests to use anti-BMP4/2 antibodies as a targeting molecule to deliver a conjugated toxin to the tumor cells. A treatment of cancer using the inhibition of BMP4 signaling is not suggested.

In a further aspect, the invention provides an antibody specifically binding to BMP4 (meaning that the antibody only binds BMP4 while it does not substantially bind to another antigen like BMP2) for use in the treatment of cancer. A use of an antibody specifically binding to BMP4 for the preparation of a medicament for the treatment of cancer is also provided. An advantage of the use of such BMP4-specific antibodies is that these antibodies specifically binding to BMP4 have less side effects in vivo than antibodies binding to both BMP4 and BMP2. No specific anti-BMP4 antibodies are disclosed in WO2008030611, since the antibodies used in WO2008030611 bind BMP4 and BMP2. Other anti-BMP4 antibodies are known, including anti-BMP4 Clone 66119, Mouse IgG2B, R&D, MAB757, described in Satish Khurana et al. Stem Cells, Vol. 32, no. 11, 14 Nov. 2014, pages 3012-3022), anti-BMP4 3H2 (Prepotech, 500-M121, described in A. Bhattacherjee et al., Journal of Neuroscience, vol. 33, no. 3, 16 Jan. 2013, pages 1050-1061,) and anti-BMP4 EPR6211 (Millipore, MABD188, described in Kwak Young-Don et al., Biochemical and Biophysical Research Communications, vol. 447, no. 3, 13 Apr. 2014, pages 394-39). However, these antibodies are not used in anti tumor therapies.

The invention further provides a pharmaceutical composition comprising an antibody capable of inhibiting BMP4 signaling and a pharmaceutically acceptable carrier for use in the treatment of a SMAD4 deficient tumor. Preferably, said antibody is a specific anti BMP4 antibody. In some embodiments said pharmaceutical composition further comprises an anti-cancer drug. Said anti-cancer drug preferably comprises platinum complexes. In a preferred embodiment, said anti-cancer drug is cis-diamminedichloroplatinum (II) (CDDP, cis-platin), oxaliplatin or carboplatin or a derivative thereof. Preferably, said cancer is selected from the group consisting of testicular cancer, bone cancer, prostate cancer, mammary cancer, lung cancer, colorectal cancer, breast cancer, gastric cancer, pancreatic cancer, esophageal cancer, ovarian cancer, squamous cell carcinoma and head and neck cancer. More preferably said cancer is selected from the group consisting of colorectal cancer, esophageal cancer, squamous cell carcinoma, pancreatic cancer and gastric cancer. In these cancer types, SMAD4 deficient tumors frequently occur.

The invention further provides an isolated, synthetic or recombinant antibody which binds to at least 4 residues of an epitope located within residues 10-17, 24-31, 45-72, 89, 91, 101, 103, 104, and 106 of BMP4 having the amino acid sequence of SEQ ID NO:1. This is a conformational epitope. An advantage of these antibodies is that they effectively inhibit tumor growth in SMAD4 deficient tumor cells. Furthermore, they are much more potent in inhibiting BMP4 signaling compared to the existing antibodies and are therefore effective at a much lower concentration. In WO2008030611 several antibodies are described which have an affinity for BMP2 and BMP4. The antibodies 8B3 and 7D6 (Example 3, Tables 1 and 2 of WO2008030611) bind to the epitope ISMLYLOENELVVLK of BMP2. A difference between the above-mentioned antibodies of the invention and the 8B3 and 7D6 antibodies of WO2008030611 is that said antibodies of the invention bind to at least 4 residues of the BMPR1a binding site of BMP4. This epitope is located within residues 10-17, 24-31, 45-72, 89, 91, 101, 103, 104, and 106 of the BMP4. In examples 11 and 17 herein, it is shown that differences in epitope explain that antibodies which bind to the BMPR1a binding site are indeed much more potent in inhibiting BMP4 signaling compared to the existing antibodies and are therefore effective at a much lower concentration. In Example 7 and FIG. 10b of WO2008030611 it is shown that antibodies 8B3 and 7D6 are capable of inhibiting binding of the Type I BMP receptor, but at a higher concentration than the antibodies of the invention. The concentration at which some antibodies described in WO2008030611 can effectively inhibit BMP4 binding to BMPR1 in vitro is at about 100 nM. The capability of inhibition of BMP4 signaling of these antibodies is not shown, but the BMP4 signaling inhibition capability of other anti-BMP2/4 monoclonal antibodies is shown in FIG. 11b, reaching effective inhibition at a concentration between 2 and 4 μg/ml. This is in clear contrast with the blocking efficiency of the above-mentioned antibodies of the invention. The inventors have demonstrated inter alia in FIG. 32D that BMP4 signaling can be inhibited effectively with antibodies according to the invention at a concentration around 100 and 1000 pM.

Furthermore, antibodies of the invention can inhibit tumor growth by direct inhibition of BMP4 signaling. In contrast, WO2008030611 teaches that anti BMP4 antibodies should be conjugated to a toxin to have an in vivo inhibitory effect on tumor growth (see example 14).

There are other antibodies known which bind to BMP4, described in Satish Khurana et al. A. Bhattacherjee et al., and Kwak Young-Don et al. Other antibodies that are available are anti-BMP4 Abcam (Rabbit polyclonal, ab39973), clone PA354-16.1.1 (Mouse Monoclonal IgG2ak, Millipore, MABD411) and), Clone M912262 (Antibodies online, ABIN934071). The inventors have shown herein that antibodies disclosed in Satish Khurana et al., A. Bhattacherjee et al., Kwak Young-Don et al., and 3 other monoclonal antibodies summarized in Table 5 do not bind to the same epitope as C4C4 and C8C8 (see FIGS. 16F, 31, 33D, and 34C). The inventors found that antibodies of the invention have much stronger inhibitory effects on BMP4 signaling compared to the antibodies of the prior art, as shown in FIG. 32D herein.

The inventors have identified novel antibodies which are capable of blocking BMP4 signaling more strongly and/or at lower concentrations.

Preferably, the $K_D$ of said antibody is lower than 1590 pM$^{-1}$, more preferably lower than 1500, 1400, 1300, 1200, 1100, 1000, 900, 800, 750, 700, 650, 635, 600, 575, 513, 393, 392, 100, 91, 75, 50, 32, 31, 25, 10 pM$^{-1}$. Preferably, said antibody is capable of inhibiting BMP4 signaling with at least equivalent or lower IC50 in a ID1 promoter activity assay as Noggin. In another preferred embodiment said antibody is capable of inhibiting BMP4 signaling with at least equivalent or lower IC50 of 1.5 μM, more preferably 1.4, 1.3, 1.2, 1.1, 1.0, 0.9, 0.8 0.7, 0.6, 0.5, 0.4, 0.3, 0.2 μM or lower.

In a preferred embodiment said epitope is located in the wrist within residues 10-17, 24-31, 45-72, 89, 91, 101, 103, 104, and 106 of BMP4.

Preferably, an antibody according to the invention binds within residues 10-17, 45-56, and 69 of BMP4. This epitope contains a hydrophobic groove, which the inventors believe is important for BMP4 specific binding. An advantage of the antibodies according to this embodiment is that said antibodies have a low affinity for other members of the BMP family and are highly effective in specifically inhibiting BMP4 signaling. Preferably, said antibody does not substantially bind to BMP2, BMP5, BMP6 or BMP7. A further advantage thereof is that said antibody does not inhibit BMP2 mediated signaling, thereby diminishing or even avoiding adverse side effects when used in vivo. More preferably, said antibody specifically binds to at least one residue selected from the group consisting of Lys10, Asn11, Lys12, Asn13, Cys14, Arg15, Arg16, and His17, at least one residue selected from the group consisting of Gly45, Asp46, Cys47, Pro48, Phe49, Pro50, Leu51, Ala52, Asp53, His54, Leu55 and Asn56, and to Ser69 of BMP4. Preferably, said antibody binds to more than 4, 5, 6, 7, 8, 9, 10, 11, 12, 13, 14, 15 preferably 16 residues thereof. In a highly preferred embodiment, said antibody specifically binds to at least Lys12, Arg15, Asp46, and Pro50 of BMP4.

In a preferred embodiment, an antibody according to the invention is a single chain antibody. In a preferred embodiment, said antibody comprises a heavy chain CDR2 consisting of the amino acid sequence of SEQ ID NO: 3 or a sequence not differing more than 2 amino acid thereof, a heavy chain CDR3 consisting of the amino acid sequence of SEQ ID NO:4, or a sequence not differing more than 1 amino acid thereof, and preferably further a heavy chain CDR1 consisting of the amino acid sequence of SEQ ID NO: 2 or a sequence not differing more than 1 amino acid thereof. In a highly preferred embodiment, said antibody comprises the amino acid sequence of SEQ ID NO: 11.

In another embodiment, an antibody according to the invention binds within residues 24-31, 57-68, 70-72, 89, 91, 101, 103, 104 and 106 of BMP4 (as depicted in SEQ ID NO:1). This region represents a "hydrophobic pocket" within the wrist epitope of BMP4. An advantage of antibodies which bind to this region is that these antibodies have a very high affinity for BMP4 and BMP2 and are also capable of efficiently inhibiting BMP4 and BMP2 signaling. Preferably, said antibody specifically binds to at least one residue selected from the group consisting of Ser24, Asp25, Val26, Gly27, Trp28, Asn29, Asp30, Trp31; at least one residue selected from the group consisting of Ser57, Thr58, Asn59, His60, Ala61, Ile62, Val63, Gln64, Thr65, Leu66, Val67, and Asn68; at least one residue selected from the group consisting of Val70, Asn71 and Ser72; at least one residue selected from the group consisting of Tyr103 and Gln104; and Met89, Tyr91, Lys101, and to Met106 of BMP4. Preferably, said antibody binds to more than 9, 10, 11, 12, 13 preferably 14 residues thereof. In a highly preferred embodiment, said antibody specifically binds to Asp30, Trp31, Leu66 and Lys101.

In a preferred embodiment, said antibody is a single chain antibody. In a preferred embodiment, said single chain antibody is capable of binding to a "hydrophobic pocket" region within the wrist epitope of BMP4 as described above. In a preferred embodiment, an antibody according to the invention comprises a heavy chain CDR3 consisting of the amino acid sequence of SEQ ID NO: 7 or a sequence not differing more than 1 amino acid thereof. Without wishing to be bound by theory, the inventors believe that this CDR3 is important for the binding interaction with the hydrophobic pocket of the wrist of BMP4. Preferably, said antibody further comprises a heavy chain CDR1 consisting of the amino acid sequence of SEQ ID NO: 5 or a sequence not differing more than 1 amino acid thereof, and a heavy chain CDR2 consisting of the amino acid sequence of SEQ ID NO:6, or a sequence not differing more than 1 amino acid thereof. In a highly preferred embodiment, said antibody comprises the amino acid sequence of SEQ ID NO: 12.

In yet another embodiment of the antibody of the invention, said antibody binds specifically within residues 34, 35, 39, 86-88, 90, 97, 98, 100, 102 and 109 of BMP4. This region represents the so called "knuckle" epitope of BMP4. Antibodies specifically binding to residues in this region also have a high affinity for BMP4, but in addition also a high affinity for BMP2 and slightly less for BMP5, and BMP6. Preferably, said antibody binds specifically binding to Ala34, Gln39, Ser88, Leu90 and Leu100.

In a preferred embodiment, said antibody is a single chain antibody. In a preferred embodiment, an antibody capable of binding to said knuckle as described above comprises a heavy chain CDR1 consisting of the amino acid sequence of SEQ ID NO: 8 or a sequence not differing more than 1 amino acid thereof and a heavy chain CDR2 consisting of the amino acid sequence of SEQ ID NO:9, or a sequence not differing more than 1 amino acid thereof. Without wishing to be bound by theory, the inventors believe that these CDRs are important for the binding interaction with the knuckle of BMP4. Said antibody preferably further comprises a heavy chain CDR3 consisting of the amino acid sequence of SEQ ID NO: 10 or a sequence not differing more than 1 amino acid thereof. In a highly preferred embodiment, said antibody comprises the amino acid sequence of SEQ ID NO: 14.

Antibodies according to the invention are preferably capable of inhibiting BMP4 signaling. Preferably, a single chain antibody according to the invention is a VHH.

The inventors have further found that linking two or more of the antibodies according to the invention results in hetero or homo multimeric molecules with increased antigen affinity for the antigens and/or an increased inhibitory effect on BMP signaling. In a further aspect, the invention therefore provides a multimeric antibody comprising at least one, more preferably at least two antibodies of the invention. In a preferred embodiment, said multimeric antibody comprises at least two of said antibodies capable of binding to the hydrophobic groove of wrist of BMP4 as described above. An advantage thereof is that such multimeric antibody has an improved affinity for BMP4 and also has an improved inhibitory effect on BMP4 signaling. Said multimeric antibody, as exemplified by C4C4 as described in the examples, proved to have a very high affinity to BMP4 (KD 9.7 pM) which is 10 times higher than that of Noggin (KD 91 pM) and 70 times higher compared to BMPR1a (KD 635 pM). Consequently, it exhibits a highly potent neutralizing activity for BMP4 signaling. In another embodiment, said multimeric antibody comprises at least two of said antibodies capable of binding to the hydrophobic pocket of wrist of BMP4 as described above. An advantage thereof is that such multimeric antibody has an improved affinity for BMP4 and BMP2 and also has an improved inhibitory effect on BMP4 as well as BMP2 signaling. In addition, such multimeric antibody have an ability to significantly abrogate BMP activity, almost to the level of Noggin. In another embodiment, said multimeric antibody comprises at least one antibody capable of binding to the knuckle of BMP4 as described above and one antibody capable of binding to the hydrophobic pocket of BMP4 as described above. An advantage thereof is that such multimeric antibody has an ability to significantly abrogate BMP activity.

In a further aspect the invention provides a composition comprising an antibody according to the invention as described above or a multimeric antibody of the invention and, preferably, a pharmaceutically acceptable carrier.

In another aspect, the invention provides a multimeric antibody according to the invention or a composition according to the invention for use in a medical treatment, preferably in the treatment of a disease caused by abnormal or elevated BMP4 levels. Preferably said disease is selected from the group consisting of: fibrodysplasia ossificans progressiva (FOP), progressive osseous heteroplasia (POH), spinal chord injury, intramuscular hematoma, complications from orthopedic surgery, psoriatic arthritis, osteoarthritis, ankylosing spondylitis (AS), seronegative arthropathies, skeletal hyperpstosis, otosclerosis, stapes ankylosis, bone cancer, prostate cancer, mammary cancer, lung cancer, heterotopic ossification, cardiac hyperthrophy, intraventricular hemorrhage, chronic kidney disease, exotoses, artheroscle-rosis, valvular heart disease, glomerulosclerosis, hypoxic pulmonary hypertension, cancer, and hair loss. Preferably said cancer is selected from the group consisting of testicular cancer, bone cancer, prostate cancer, mammary cancer, lung cancer, colorectal cancer, breast cancer, gastric cancer, pancreatic, esophageal cancer, ovarian cancer, squamous cell carcinoma, head and neck cancer.

In a further aspect, the invention provides an isolated nucleic acid molecule encoding at least the heavy chain of an antibody according to the invention. Preferably, said nucleic acid molecule encodes an antibody according to the invention. In an embodiment, said nucleic acid is a cDNA.

The invention further provides an expression vector comprising a nucleic acid molecule of the invention.

The invention further provides a host cell comprising an expression vector of the invention.

In another aspect, the invention provides a hybridoma expressing an antibody according to the invention.

In another aspect, the invention provides a method of blocking BMP4 signaling in vitro, comprising providing an antibody according to the invention or a multimeric antibody according to the invention to a cell sample.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

FIG. 19 shows a cartoon diagram of BMP4-C4 binding as determined by HADDOCK. A) The BMP4 dimer is shown in green and red. C4 is shown in cyan. B) Enlarged view of the molecular interface between BMP4 and C4. Dotted lines represent hydrogen bonds and/or salt bridges. BMP4 (yellow) and C4 (magenta) residues participating in interactions are displayed as sticks.

FIG. 27 shows the epitope mapping with heterodimer BMPs. C2C12 were activated with 10 ng/ml of human BMP4 and BMP4/6 (FIG. 27A) or 50 ng/ml of BMP2, BMP2/6 or BMP2/7 (FIG. 27B), from R&D systems. Error bars represent standard deviations of the mean, calculated from at least three independent experiments, with experimental triplicates each. Error bars represent standard deviations of the mean, calculated from a representative experiment, with experimental triplicates. N=Noggin.

FIG. 28 (A) shows that C2C12 cells were incubated with conditioned media from a panel of different colon cancer cell lines. FIG. 28(B) shows that C2C12 cells were incubated with conditioned media of the indicated cancer cell lines. C4C4, C8C8 or human Fc-Noggin were added at the same time at a concentration of 500 ng/ml for 16 hours. HT29 cells were treated with Carboplatin (FIG. 28C), 5'FU (D) or Oxaliplatin (FIG. 28E) at the indicated concentrations with or without VHHs or Noggin. After 48 hours the viability was measured. Experiments were repeated at least three times with experimental triplicates each. **p=<0.01, *p=<0.1. Statistical analysis was done using a two-tailed P-test.

FIG. 29A shows that C4C4 and C8C8 can inhibit pSMAD phosphorylation in HT29 cells. FIG. 29B shows that HCT116 but not HT29 express SMAD4. C4C4 and C8C8 inhibit the phosphorylation of the kinases p38 (29C), Akt (FIG. 29D) as well as ERK (FIG. 29E).

DETAILED DESCRIPTION OF THE INVENTION

Definitions

Figure 1A:
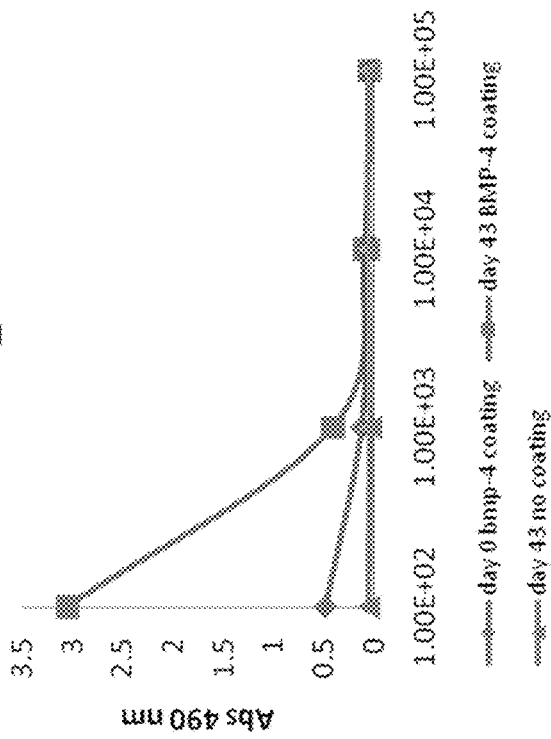
FIGS. 1 (A and B) shows the titration of the sera of llama#18-2 and llama#31-2 that were immunized with purified BMP-4 in the presence of adjuvant Stimune (Prionics, Lelystad, The Netherlands) on BMP4. Both llamas show a clear increase in signal measured in the immune serum of day 43, compared to preimmune serum of day 0. The signal is specific, since no signal was measured with serum of day 43 in non-coated wells.

As used herein, the term "SMAD4" has its general meaning in the art. SMAD4 (also known as MADH4 and DPC4) represents the most unique member of the Smad family. This protein acts as a shared hetero-oligomerization partner in complexes with the pathway-restricted Smads (Lagna et al., Nature, 1996, 383, 832-836; Zhang et al., Curr. Biol., 1997, 7, 270-276). Recently it has been demonstrated that although SMAD4 does not interact with the TGF-beta receptor, it does perform two distinct functions within the Smad signaling cascade. Through its N-terminus SMAD4 promotes the binding of the Smad complex to DNA, and through its C-terminus it provides an activation signal required for the Smad complex to stimulate transcription (Liu et al, Genes Dev., 1997, 11, 3157-3167). SMAD4 was first isolated as a possible tumor suppressor gene during studies of pancreatic carcinomas. Homo sapiens SMAD4 gene is localized to chromosome 18q21.1 (Hahn et al., Science, 1996, 271, 350-353), the sequence of which is deposited in Genebank under accession number NG_013013.1.

As used herein, the term "SMAD4 deficient tumor" refers to a tumor characterized by the fact that at least part of its cells have a decreased expression of the SMAD4 gene or have a reduced function of the SMAD4 protein. Deficient tumors may be characterized by a decreased amount, preferably to less than 50%, more preferably less than 40%, 30%, 20% or 10% compared to control cells, or the loss of the SMAd4 protein, by the presence of SMAD4 genomic aberrations (mutations, deletions, etc) which result in a decreased function or the loss of function of the SMAD4 gene, hypermethilation of the SMAD4 locus or by decreased RNA levels of SMAD4.

The term "epitope" used herein indicates an antigenic determinant and is interpreted to mean a site on an antigen recognized by an antibody.

As used herein, the term "conformational epitope" refers to a portion of a full-length protein, or an analog or mutant thereof, having structural features native to the amino acid sequence encoding the epitope within the full-length natural protein. Native structural features include, but are not limited to, glycosylation and three dimensional structure. The length of the epitope defining sequence can be subject to wide variations as these epitopes are believed to be formed by the three-dimensional shape of the antigen (e.g., folding). Thus, amino acids defining the epitope can be relatively few in number, but widely dispersed along the length of the molecule, being brought into correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

With regard to recognition of conformational epitopes, the antibody recognizes a 3-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography 2-dimensional nuclear magnetic resonance spectroscopy and site-directed spin labeling and electron paramagnetic resonance spectroscopy. See, for example, Epitope Mapping Protocols in Methods in Molecular Biology, Vol. 66, Glenn E. Morris, Ed. (1996), the disclosure of which is incorporated in its entirety herein by reference.

The term "immunoglobulin" (abbreviated as "Ig") as used herein is well-known in the art and equals the term "antibody". The term "antibody" as used herein refers to any polypeptide comprising an antigen-binding site with at least one complementarity determining region (CDR). The term includes, but is not limited to polyclonal antibodies, monoclonal antibodies, monospecific antibodies, multispecific antibodies, humanized antibodies, chimeric antibodies, human antibodies, and single-chain antibodies (e.g., VHH, VNAR). The term "antibody" also includes antibody fragments such Fab, F(ab')2, Fv, scFv, Fd, dAb, and other antibody fragments or other constructs comprising CDRs that retain antigen-binding function. Typically, such fragments would comprise an antigen-binding domain (or "antigen-binding portion", these terms are used interchangeably herein). The antibodies may be any of the known antibody isotypes and their conformations, for example, IgA, such as IgA1 or IgA2, IgD, IgE, IgG, such as IgG1, IgG2a, IgG2b, IgG3, IgG4, or IgM class, or may constitute mixtures thereof in any combination, such as a mixture of antibodies from the IgG1 and IgG2a class.

In embodiments, the term "antibody", also referred to in the art as "immunoglobulin" encompasses a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable (VL) and a constant (CL) domain, while the heavy chain folds into a variable (VH) and three constant (CH, CH2, CH3) domains. Interaction of the heavy and light chain variable domains (VH and VL) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen binding determinants of the molecule, and thus determines the specificity of an antibody for its target antigen. The majority of sequence variability occurs in six hypervariable regions, three each per variable heavy and light chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the VH and VL domains. Chothia and Lesk (1987) define the "hypervariable loops" (H or L) based on the location of the structural loop regions in the VH and VL domains; the numbering for the hypervariable loops is defined as H1: 27-35; H2: 52-56; and H3: 95-102 (equivalent to CDR3 of Kabat numbering) for VHH domains (Chothia and Lesk, 1987). As these individual schemes define CDR and hypervariable loop regions that are adjacent or overlapping, those of skill in the antibody art often utilize the terms "CDR" and "hypervariable loop" interchangeably, and they may be so used herein.

The region outside of the CDR is referred to as the framework region (FR). The FR provides structural integrity to the variable domain and ensures retention of the immunoglobulin fold. This characteristic structure of antibodies provides a stable scaffold upon which substantial antigen-binding diversity can be explored by the immune system to obtain specificity for a broad array of antigens (Padlan et al, 1994).

The term "antigen-binding portion" of an antibody (or "antigen-binding fragment"), as used herein, refers to one or more fragments of an antibody that retain the ability to specifically bind to an antigen (e.g., to an epitope within the BMP4 protein). It has been shown that the antigen-binding function of an antibody can be performed by fragments of a full-length antibody. The antibody fragment may be obtained by manipulation of a naturally-occurring antibody, or may be obtained using recombinant methods. Examples of binding fragments encompassed within the term "antigen-binding portion" of an antibody include (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fab' fragment, which is essentially an Fab with part of the hinge region {see, FUNDAMENTAL IMMUNOLOGY (Paul ed., 3.sup.rd ed. 1993); (iv) a Fd fragment consisting of the VH and CHI domains; (v) a Fv fragment consisting of the VL and VH domains of a single arm of an antibody, (vi) a dAb fragment (Ward et al., (1989) Nature 341:544-546), which consists of a VH domain; (vii) an isolated complementarity determining region (CDR); and (viii) a nanobody, a heavy chain variable region containing a single variable domain and two constant domains. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. ScL USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

In a non-limiting example, the antibody fragment may be a single domain antibody (also single chain antibody) derived from naturally-occurring sources. The term single domain or single chain antibody may also be a multivalent presentation thereof. Typical single chain antibodies are heavy chain antibodies of camelid origin (Hamers-Casterman et al, 1993), which lack light chains and thus their antigen binding sites consist of one domain, termed VHH. Single-domain antibodies have also been observed in shark and are termed VNARs (Nuttall et al, 2003); other single-domain antibodies may be engineered based on human heavy or light chain sequences (Jespers et al, 2004; To et al, 2005). As used herein, "single-domain antibody" includes those directly isolated from VL, VH, VHH or VNAR reservoir of any origin through phage display or other display technologies and those generated through further modification of such single-domain antibody by humanization, affinity maturation, stabilization, solubilisation (e.g., camelization), or other methods of antibody engineering. Also encompassed by the present invention are homologues, derivatives, or fragments that retain or improve the antigen-binding function and specificity of the single-domain antibody.

A person of skill in the art would be well-acquainted with the structure of a single-domain antibody (see, for example, 3DWT, 2P42 in Protein Data Bank). A single-domain antibody comprises a single immunoglobulin domain that retains the immunoglobulin fold; most notably, only three CDR form the antigen-binding site. However, not all CDR may be required for binding the antigen. For example, and without wishing to be limiting, one, two, or three of the CDR may contribute to binding and recognition of the antigen by the single-domain antibody of the present invention. The CDR of the single-domain antibody are referred to herein as CDR1, CDR2, and CDR3, and are based on Kabat numbering (Kabat et al. 1991).

The single-domain antibody may be of camelid origin, and thus may be based on camelid framework regions; alternatively, the CDR may be grafted onto the framework regions of other antibody domains, for example but not limited to VNAR, human VH or human VL framework regions. In yet another alternative, the CDR described above may be grafted onto the framework regions of other types of antibody fragments (Fv, scFv, Fab). The present embodiment further encompasses an antibody fragment that is "humanized" using any suitable method known in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody when introduced into human subjects. In the process of CDR grafting, one or more than one of the heavy chain CDR defined herein may be fused or grafted to a human variable region (VH, or VL), or to other human antibody fragment framework regions (Fv, scFv, Fab). In such a case, the conformation of said one or more than one hypervariable loop is preserved, and the affinity and specificity of the single-domain antibody for its target (i.e., BMP4) is also preserved. CDR grafting is known in the art and is described in at least the following: U.S. Pat. Nos. 6,180,370, 5,693, 761, 6,054,297, 5,859,205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. Nos. 5,869,619, 5,766,886, 5,821,123, and European Patent No. 519596. Persons of skill in the art would be amply familiar with methods of preparing such humanized antibody fragments.

An "isolated antibody", as used herein, is intended to refer to an antibody that is substantially free of other antibodies having different antigenic specificities (e.g., an isolated antibody that specifically binds a BMP4 protein is substantially free of antibodies that specifically bind antigens other than BMP4 proteins). An isolated antibody that specifically binds a human BMP4 protein may, however, have cross-reactivity to other antigens, such as BMP4 proteins from other species. Moreover, an isolated antibody is preferably substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope. The term "human antibody", as used herein, is intended to include antibodies having variable regions in which both the framework and CDR regions are derived from human germline immunoglobulin sequences. Furthermore, if the antibody contains a constant region, the constant region also is derived from human germ line immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell. The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "isotype" refers to the antibody class (e.g., IgM or IgG) that is encoded by the heavy chain constant region genes. The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody. The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "Kassoc" or "$k_a$", as used herein, is intended to refer to the association rate of a particular antibody-antigen interaction, whereas the term "KdiS" or "$k_d$," as used herein, is intended to refer to the dissociation rate of a particular antibody-antigen interaction. The term "$K_D$," as used herein, is intended to refer to the dissociation constant, which is obtained from the ratio of $k_d$ to $k_a$ (i.e., $k_d/k_a$) and is expressed as a molar concentration (M). $K_D$ values for antibody can be determined using methods well established in the art. A preferred method for determining the $K_D$ of an antibody is by using surface plasmon resonance, preferably using a biosensor system such as a Biacore® system.

The term "IC50" as used herein describes the half maximal inhibitory concentration (IC50) which is a measure of the effectiveness of a compound in inhibiting biological function, e.g. inhibition of an antibody on BMP4 signaling in C2C12 cells as described herein.

The term "high affinity" as used herein when relating to affinity of the antibody for a certain epitope, such affinity has a value of $K_D$ of $1\times10^{-7}$ M or less, more preferably $1\times10^{-8}$ M or less, more preferably $6\times10^{-9}$ M or less, more preferably $3\times10^{-9}$ M or less, more preferably $2\times10^{-9}$ M or less.

The term "binds to" or "binding to" as used herein in the context of the interaction between an antibody and an antigen, is intended to refer to the capability of the antibody of binding to the antigen by an immunoglobulin variable region of the antibody with a dissociation constant of $K_D$ of $1\times10^{-6}$ M or less, preferably of $1\times10^{-7}$ M or less, more preferably $1\times10^{-8}$ M or less, more preferably $6\times10^{-9}$ M or less, more preferably $3\times10^{-9}$ M or less, more preferably $2\times10^{-9}$ M or less. Said antibody may, or may not, additionally bind another antigen. For instance, an antibody binding to BMP4 may also be able to bind BMP2.

As used herein, an antibody that "specifically binds" to a certain antigen is intended to refer to an antibody that binds to said certain antigen, but does not substantially bind to another antigen. For instance, an antibody that specifically binds BMP4 typically does not substantially bind BMP2.

The term "binds within" a certain epitope as used herein refers to an antibody which binds to one, but preferably at least 2, 3, 5, 6, 7, 8 or more residues within an epitope of BMP4. It may be that binding also takes place outside the residues mentioned. However, in preferred embodiments, said antibody does not substantially bind to any other epitope of BMP4.

The term "does not substantially bind" to an epitope, as used herein, means does not bind or does not bind with a high affinity to the epitope, i.e. binds to the epitope with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

BMPs are secreted as inactive precursors (proBMPs) that need to be cleaved extracellularly in order to release their mature and active forms. As used herein, the term "BMP2" is used to refer to mature bone morphogenic protein 2, preferably of human origin. The nucleotide sequence of human pro-BMP2 is publicly available by reference to GenBank Accession No. NM_001200. The corresponding amino acid sequence of mature BMP2 is presented herein as SEQ ID NO: 15.

As used herein, the term "BMP4" is used to refer to human mature bone morphogenic protein 4. The nucleotide sequence of human pro-BMP4 is publicly available by reference to GenBank Accession No. NM_130851. The corresponding amino acid sequence of mature BMP4 is presented herein as SEQ ID NO: 1. The numbering of the residues as used herein refer to the positions of SEQ ID NO:1. As BMP4 is highly conserved among individuals, said epitope is also highly conserved, but may vary slightly between individuals. Therefore, antibodies that bind to said epitope of a variant of BMP4 are within the scope of the present invention. BMP4 is defined by the amino acid of SEQ ID NO:1 or a sequence at least 85%, preferably at least 86, 87, 88, 89, 90, 91, 92, 93, 94, 95, 96, 97, 98, 99% identical thereto.

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at http://ca.expasy.org/tools/ blast/), BLAST-P, Blast-N, or FASTA-N, or any other appropriate software that is known in the art.

The term the "wrist" of BMP4 as used herein refers to the region within the BMP4 protein which binds to type I receptors, such as BMPR1a and BMPR1b.

The term "knuckle" of BMP4 as used herein refers to the region within the BMP4 protein which binds to type II receptors, such as BMPR2, ActRII and ActRIIB.

As used herein, the term "BMP5" is used to refer to human mature bone morphogenic protein 5. The amino acid sequence of pro-BMP5 is publicly available by reference to GenBank Accession No. NP_066551.1 and mature human BMP5 is presented herein as SEQ ID NO: 16.

As used herein, the term "BMP6" is used to refer to human mature bone morphogenic protein 6. The amino acid sequence of pro-BMP6 is publicly available by reference to GenBank Accession No. NP_001709.1 and its mature form is presented herein as SEQ ID NO: 17.

As used herein, the term "BMP7" is used to refer to human mature bone morphogenic protein 7. The amino acid sequence of pro-BMP7 is publicly available by reference to GenBank Accession No. NP_001710.1 and its mature form is presented herein as SEQ ID NO: 18.

The term "disease associated with abnormal BMP4 expression" refers to any disease wherein BMP4 expression in a test sample of a subject is aberrant, preferably elevated compared to a test sample of a healthy control.

The term "BMP4 signaling" as used herein refers to the ability of BMP4 to activate the canonical (the phosphorylation of SMAD 1/5/8) and/or noncanonical pathways (including but not limited to phosphorylation of ERK, p38 and Akt).

The term "BMP2 signaling" as used herein refers to the ability of BMP2 to activate the canonical (the phosphorylation of SMAD 1/5/8) and/or noncanonical pathways (including but not limited to phosphorylation of ERK, p38 and Akt).

The term "C4" as used herein refers to single chain antibody according to the invention which binds to the hydrophobic groove of the wrist of BMP4.

The term "C4C4" as used herein refers to a dimer of said C4 single chain antibody.

The term "C8" as used herein refers to single chain antibody according to the invention which binds to the hydrophobic groove of the wrist of BMP4.

The term "C8C8" as used herein refers to a dimer of said C8 single chain antibody.

As used herein, lung cancer refers to cancer that begins in the lung including but not limited to non-small cell lung cancer and small cell lung cancer.

As used herein, testicular cancer refers to cancer that starts in the testicles, including but not limited to seminomas and non-seminomas.

As used herein, breast cancer refers to cancer that starts in the tissue of the breast, including but not limited to ductal carcinoma and lobular carcinoma.

As used herein, colon cancer refers to cancer that starts in the large intestine or the rectum, including but not limited to carcinoma, lymphoma, carcinoid tumours, melanoma and sarcomas.

As used herein, ovarian cancer refers to cancer that starts in the ovaries, including but not limited to epithelial tumours, germ cell tumours and stromal tumours.

As used herein, head and neck cancer refers to a group of cancers that starts in the upper aerodigestive tract, including but not limited to the lip, oral cavity, nasal cavity, paranasal sinuses, pharynx, and larynx.

As used herein, esophageal cancer refers to cancer that starts in the esophagus, including but not limited to squamous cell carcinoma and adenocarcinoma.

As used herein, gastric cancer refers to cancer that starts in the stomach, including but not limited to adenocarcinoma, soft tissue sarcoma, lymphoma and carcinoid tumours.

As used herein, the term anti-cancer drug refers to drugs used to treat malignancies or cancerous growths that may be used alone or in combination with other treatments. Examples of anti-cancer drugs include but are not limited to platinum complexes.

As used in the context of the specification, the term platinum complex refers to compounds comprising platinum that form intrastrand and interstrand cross-links between purines on DNA. Examples include but are not limited to cisplatin (also known as cis-diamminedichloroplatinum (II) or CDDP), oxaliplatin, carboplatin and derivatives thereof.

As used herein, the phrase 'derivatives thereof' in relation to platinum complexes refers to platinum containing compound comprising different ligands.

Various aspects of the invention are described in further detail in the following subsections.

Antibody Binding to BMP4 for Use in the Treatment of a SMAD4 Deficient Tumor.

Smad4 deficient tumors may be identified using methods known in the art, for instance using in vitro screening methods described in EP2046374A2. Smad4 deficient tumors may suitably be treated using anti-BMP4 antibodies which are capable of inhibiting BMP4 signaling. Such antibodies are known in the art and disclosed for instance in WO2008030611. In some embodiments, an anti-BMP4 antibody according to the present invention is used.

Antibodies which Bind to the Wrist or the Knuckle of BMP4

The invention is based on the finding that antibodies which bind to the wrist or the knuckle of BMP4 have a high affinity for BMP4 compared to presently available anti-BMP4 antibodies. In example 7 herein, affinities of several antibodies according to the invention are compared with a commercially available anti-BMP4 antibody. Without wishing to be bound by theory, the inventors believe that this is the result from the fact that the available antibodies are directed to different epitopes of BMP4 (example 8, 9 and 10). The invention therefore relates to any antibody which binds the wrist or to the knuckle of BMP4.

In an embodiment, the antibody of the invention binds to the wrist of BMP4. These antibodies are capable interfering with type I receptors of BMP4, such as BMPR1a and BMPR1b. Without wishing to be bound by theory, the inventors are of the opinion that this region of interaction with the type I receptors is located within residues 10-17, 24-31, 45-72, 89, 91, 101, 103, 104, and 106 of BMP4. Any antibody which is capable of binding thereto is within the scope of the present invention.

Standard assays to evaluate the binding ability of the antibodies toward one or more epitopes are known in the art including, for example, ELISAs, Western blots, flow cytometry and RIAs. Other suitable assays are described in detail in the Examples. The binding kinetics (e.g., binding affinity) of the antibodies also can be assessed by standard assays known in the art, such as by ELISA, Scatchard and Biacore analysis. Preferably, said antibody has an affinity $K_D$ lower than 1590 pM$^{-1}$ for BMP4, as determined using surface plasmon resonance analysis. Preferably, said $K_D$ is lower than 1000 pM$^{-1}$, more preferably lower than 1500, 1400, 1300, 1200, 1100, 1000, 900, 800, 750, 700, 650, 635, 600, 575, 513, 393, 100, 91, 75, 50, 32, 25, 10 pM$^{-1}$.

Furthermore, the inventors have described herein that the antibodies of the invention inhibit BMP4 signaling to the same extent as Noggin. This may be explained by the wide reach of contact points of Noggin, which simultaneously masks both BMPR1a and BMPR2 epitopes. Whereas a C-terminal finger-like region of Noggin is the responsible for blocking BMPR2 binding, an N-terminal clip-like region binds to the BMPR1a epitope. This remarkable structural reach is conserved amongst BMP antagonists and might explain their lack of BMP-specificity.

Assays for determining whether an antibody competes with Noggin are known in the art. In a preferred embodiment, such assays include SPR sandwich cross-binding or "epitope binning" assay, preferably as described herein.

Antibodies which Bind to the Hydrophobic Groove of the Wrist of BMP4

The present invention is further based on the surprising finding that, in contrast to Noggin and anti-BMP4 antibodies known in the art, the antibodies which bind to the hydrophobic groove of the wrist of BMP4, do not affect signaling of the highly homologous BMP2 and/or of other BMPs including BMP5, 6, and 7 (example 5). The inventors have shown that the antibodies which bind to the hydrophobic groove of BMP4 can prevent transcriptional activation of BMP4-responsive genes, such as ID1, through inhibition of phosphorylation of the transcription factor SMAD1/5/8 (example 5).

The inventors have also shown that antibodies which bind to the hydrophobic groove of the wrist of BMP4 inhibit BMP4-mediated function only, in contrast to Noggin, that also inhibits BMP2,5,6, and 7. The homo-bihead C4C4 proved to be the single domain antibody with the highest affinity to BMP4, 10 times higher than that of Noggin. These antibodies can effectively inhibit BMP4 function, while leaving important homeostatic functions of the other BMPs intact. Unselective inhibition of BMP signaling in mice, has been shown to increase tumor burden and activation of metastatic dormancy of breast cancer cells. Thus, when using BMP inhibition as therapy, avoiding the deleterious side effects of unchecked cancer stem cell proliferation is of major importance. In the intestinal organoid cultures inhibition of BMP4 alone by antibodies of the invention which binds to the hydrophobic groove of the wrist of BMP4 (also referred to as "C4C4" herein) does not affect stem cell proliferation. The inventors have also found that certain colorectal cancer cell lines strictly secrete BMP4 and that selective inhibition of BMP4 by the antibodies of the invention in these cells is enough to increase chemosensitivity to several chemotherapeutic agents. Thus, antibodies which bind to the hydrophobic groove of the wrist of BMP4 have an important potential for clinical, diagnostic and therapeutic use in colorectal cancers but also in other neoplasms in which BMP4 might play a specific pathogenic role, such as breast, lung, prostate, and gastric cancer.

The BMP4-specificity is clearly exemplified in example 6, in which inhibition of multiple BMPs leads to proliferation of stem cells in culture, whereas specific inhibition of BMP4 (by C4C4) fails to do so.

The inventors have further demonstrated that the above mentioned effects are caused by the specificity of the antibodies of the present invention to a specific part of the wrist of BMP4.

The epitope binning experiments of the inventors (example 8) and subsequent HADDOCK modelling (example 9) have shown that antibodies of this embodiment are capable of binding specifically to the hydrophobic groove of the wrist of BMP4. This is the only area involved in BMPR binding that presents differences in residues between BMP2 and BMP4. Specifically, HADDOCK modeling confirms that hydrophobic groove residues Lys12, Arg15, Asp46, and Pro50 of BMP4 are involved in hydrophobic interactions with residues located in the CDR2 and CDR3 of C4. Mutational experiments have validated the modeling (example 10).

Preferably, said antibody binds to the hydrophobic groove of the wrist, preferably within residues 10-17, 45-56, and 69 of BMP4. In a further preferred embodiment, said antibody of this embodiment does not substantially bind to BMP2, BMP5, BMP6 or BMP7. A further advantage thereof is that said antibody does not inhibit BMP2 mediated signaling. Even more preferably, said antibody specifically binds to at least one residue selected from the group consisting of Lys10, Asn11, Lys12, Asn13, Cys14, Arg15, Arg16, and His17, at least one residue selected from the group consisting of Gly45, Asp46, Cys47, Pro48, Phe49, Pro50, Leu51, Ala52, Asp53, His54, Leu55 and Asn56, and Ser69 of BMP4. Preferably, said antibody which is capable of binding to the hydrophobic groove of the wrist of BMP4 binds to more than 4, 5, 6, 7, 8, 9, 10, 11, 12, 13, 14, 15 preferably 16 residues thereof and most preferably to all said residues, because this will result in better binding. In a highly preferred embodiment, said antibody specifically binds to at least Lys12, Arg15, Asp46, and Pro50 of BMP4.

In a preferred embodiment, said antibody binds to at least one of the residues 15, 49, 50, 51, 52, 53, 54 and 69 of BMP4. Preferably, said antibodies or antigen binding portions thereof have a specific high affinity for BMP4 and do not substantially bind to other members of the BMP family. Preferably, said antibodies are capable of functionally inhibiting a signaling function of BMP4.

In one preferred embodiment, said antibody binds to at least Arg15 of BMP4. In another preferred embodiment, said antibody binds to at least one, more preferably 2, 3, 4, 5 or 6 residue(s) of Phe49, Pro50, Leu51, Ala52, Asp53 and His54 of BMP4. In another preferred embodiment, said antibody binds to Ser69 of BMP4. In a preferred embodiment, antibody or an antigen binding portion thereof, specifically binding to Arg15, at least one residue selected from the group consisting of Phe49, Pro50, Leu51, Ala52, Asp53 and His54, and Ser69 of BMP4.

In a preferred embodiment, said antibody does not substantially bind to an amino acid located outside the hydrophobic groove of the wrist of BMP4. An advantage thereof is that no cross reaction with other proteins will occur.

The docking model showed that the hydrophobic groove residues, which are non-conserved, are involved in binding with residues from the CDR2 and CDR3 of said antibodies, therefore validating its BMP4-specificity.

In a preferred embodiment, the invention further provides an antibody according to the present invention, wherein the heavy chain variable domain comprises a CDR2 region comprising the amino acid sequence of SEQ ID NO: 3 or an amino acid sequence at least 87% identical thereto, and wherein the heavy chain variable domain comprises a CDR3 region comprising the amino acid sequence of SEQ ID NO: 4 or an amino acid sequence at least 86% identical thereto. In an alternative embodiment, Arg2 of SEQ ID NO: 3 may be substituted by Pro2. In an alternative embodiment, Ser1 of SEQ ID NO: 4 may be substituted by Ile1. Preferably, said amino acid sequence at least 87% identical to SEQ ID NO: 3 differs not more than 1 amino acid from SEQ ID NO: 3. Preferably, said amino acid sequence at least 87% identical to SEQ ID NO: 4 differs not more than 2 amino acids from SEQ ID NO: 4, more preferably not more than 1 amino acid.

Preferably, the antibody which binds to the hydrophobic groove of the wrist of BMP4 comprising the amino acid sequence of SEQ ID NO: 11 or a sequence at least 70%, more preferably 71, 72, 73, 74, 75, 80, 85, 90, 91, 92, 93, 94, 95, 96, 97, 98, 99, or 100% identical thereto. The inventors have found that Glu1 of SEQ ID NO: 11 may be substituted by Gln or Asp, Arg27 by Pro and Ser53 by Ile without detrimental effect.

Antibodies which Bind to the Hydrophobic Pocket of the Wrist of BMP4

The inventors have found that antibodies which bind to the hydrophobic pocket of the wrist of BMP4 inhibit both BMP2 and BMP4 signaling. Its affinity for BMP4 binding and of BMP2 is higher to those found for Noggin. These antibodies are also effective at neutralizing BMP4 and BMP2 signaling (example 5).

The epitope binning experiments of the antibodies of the invention (example 8) and subsequent HADDOCK modelling (example 9) have shown that antibodies of this embodiment are capable of binding to the hydrophobic pocket of the wrist of BMP4. This is the only area involved in BMPR binding that presents differences in residues between BMP2, BMP4 and the other BMPs (BMP5, 6 and 7). Specifically, HADDOCK modeling confirms that residues Asp30, Trp31, Leu66 and Lys101 of BMP4 are involved in hydrophobic interactions with residues located in the CDR3 of C8. Mutational experiments have validated this modeling (example 10).

Therefore, in a preferred embodiment, said antibody is capable of binding to the hydrophobic pocket of the wrist of BMP4. Preferably, said antibody binds within residues 24-31, 57-72, 89, 91, 101, 103, 104 and 106 of BMP4. Preferably, said antibody binds to at least one residue selected from the group consisting of Ser24, Asp25, Val26, Gly27, Trp28, Asn29, Asp30, Trp31; at least one residue selected from the group consisting of Ser57, Thr58, Asn59, His60, Ala61, Ile62, Val63, Gln64, Thr65, Leu66, Val67, and Asn68; at least one residue selected from the group consisting of Val70, Asn71 and Ser72; at least one residue selected from the group consisting of Tyr103 and Gln104; and Met89, Tyr91, Lys101, and Met106 of BMP4. Preferably, said antibody binds to more than 9, 10, 11, 12, 13, preferably 14 or more residues thereof. In a highly preferred embodiment, said antibody specifically binds to Asp30, Trp31, Leu66 and Lys101.

Using HADDOCK modeling, the inventors have concluded that binding between the antibodies which are capable of binding to the hydrophobic pocket of the wrist of BMP4 is driven by interactions between residues in the CDR3 region of said antibodies and the hydrophobic pocket of the wrist of BMP4. In the hydrophobic surface of the αhelix of BMP4, L66 sticks out to interact with T105 of said antibody. Residues in loop1 of BMP4 provide a hydrophobic area allowing for interactions like P109 with W31 of BMP4 and the double salt bridge between D30 and R106 of said antibody. Also F110 and F102 make multiple contacts with the area that D30 is enclosed. Y107 forms a hydrogen bond with K101 located at the inner side of the β8 strand.

In a preferred embodiment of the antibody capable of binding to "hydrophobic pocket" region within the wrist of BMP4 as described above, comprises therefore a heavy chain CDR3 consisting of the amino acid sequence of SEQ ID NO: 7 or a sequence not differing more than 1 amino acid thereof. It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CD R3 sequence. See, for example, Klimka et ah, British J. of Cancer 83 [pound]2):252-260 (2000) [describing the production of a humanized anti-CD30 antibody using only the heavy chain variable domain CDR3 of murine anti-CD30 antibody Ki-4]; Beiboer et al, J. Mol. Biol. 296:833-849 (2000) [describing recombinant epithelial glycoprotein-2 (EGP-2) antibodies using only the heavy chain CDR3 sequence of the parental murine MOC-31 anti-EGP-2 antibody]; Rader et al, Proc. Natl. Acad. ScI U.S.A. 95:8910-8915 (1998) [describing a panel of humanized anti-integrin [alpha]v[beta]3 antibodies using a heavy and light chain variable CDR3 domain of a murine anti-integrin [alpha]v[beta]3 antibody LM609 wherein each member antibody comprises a distinct sequence outside the CDR3 domain and capable of binding the same epitope as the parent murine antibody with affinities as high or higher than the parent murine antibody]; Barbas et al., J. Am. Chem. Soc. 116:2161-2162 (1994) [disclosing that the CDR3 domain provides the most significant contribution to antigen binding]; Barbas et ah, Proc. Natl. Acad. ScL J7.-S.i4. 92:2529-2533 (1995) [describing the grafting of heavy chain CDR3 sequences of three Fabs (SI-I, SI-40, and SI-32) against human placental DNA onto the heavy chain of an anti-tetanus toxoid Fab thereby replacing the existing heavy chain CD3 and demonstrating that the CDR3 domain alone conferred binding specificity]; and Ditzel et al, J. Immunol. 157:739-749 (1996) [describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab]. Each of these references is hereby incorporated by reference in its entirety.

Accordingly, within certain aspects, the present invention provides antibodies comprising one or more heavy chain CDR3 domain from a non-human antibody, such as a mouse or rat antibody, wherein the monoclonal antibody is capable of specifically binding to the hydrophobic pocket of the wrist of BMP4. Within some embodiments, such inventive antibodies comprising one or more heavy chain CDR3 domain from a non-human antibody (a) are capable of competing for binding with; (b) retain the functional characteristics; (c) bind to the same epitope; and/or (d) have a similar binding affinity of the corresponding parental non-human antibody. Within other aspects, the present invention provides monoclonal antibodies comprising one or more heavy chain CDR3 domain from a first human antibody, such as, for example, a human antibody obtained from a non-human animal, wherein the first human antibody is capable of specifically binding to the hydrophobic pocket of the wrist of BMP4 and wherein the CDR3 domain from the first human antibody replaces a CDR3 domain in a human antibody that is lacking binding specificity for the hydrophobic pocket of the wrist of BMP4 to generate a second human antibody that is capable of specifically binding to the hydrophobic pocket of the wrist of BMP4. Within some embodiments, such inventive antibodies comprising one or more heavy chain CDR3 domain from the first human antibody (a) are capable of competing for binding with; (b) retain the functional characteristics; (c) bind to the same epitope; and/or (d) have a similar binding affinity as the corresponding parental first human antibody.

Preferably, said antibody further comprises a heavy chain CD R1 consisting of the amino acid sequence of SEQ ID NO: 5 or a sequence not differing more than 1 amino acid thereof, and heavy chain CDR2 consisting of the amino acid sequence of SEQ ID NO:6, or a sequence not differing more than 1 amino acid thereof. The inventors have found that Ile6 of SEQ ID NO: 5 may be substituted by Val, Asn5 of SEQ ID NO:6 may be substituted by Ser and Pr12 of SEQ ID NO:7 may be substituted by Gln and Asp14 of SEQ ID NO:7 may be substituted by Gly. Preferably, the antibody which binds to the hydrophobic pocket of BMP4 comprising the amino acid sequence of SEQ ID NO: 12 or a sequence at least 70%, more preferably 71, 72, 73, 74, 75, 80, 85, 90, 91, 92, 93, 94, 95, 96, 97, 98, 99, or 100% identical thereto. The inventors have found that Glu1 of SEQ ID NO: 12 may be substituted by Gln or Asp, Ile31 by Val, Asn56 by Ser, Pro109 by Gln and Asp111 by Gly without detrimental effect.

Antibodies which Bind to the Knuckle of BMP4

The inventors have further found that antibodies which are capable of binding specifically to the knuckle of BMP4 have a specificity to BMP2,4,5 and 6. Functional experiments show that these antibodies can effectively inhibit BMP2 and BMP4 signaling, and to a lesser extent also inhibit BMP5 and BMP6 signaling.

The epitope binning experiments of the inventors (example 8) and subsequent HADDOCK modelling (example 9) have shown that antibodies of this embodiment are capable of binding specifically to the knuckle of BMP4. Specifically, HADDOCK modeling confirms that hydrophobic groove residues Ala34, Gln39, Ser88, Leu90, Leu100 of BMP4 are involved in hydrophobic interactions with residues located in the CDR1 and CDR2 of E7. Mutational experiments have validated this modeling (example 10).

Preferred antibody of the invention binds therefore specifically to the knuckle of BMP4, preferably within residues 34, 35, 39, 86-88, 90, 97, 98, 100, 102 and 109. Preferably, said antibody binds specifically binding to Ala34, Gln39, Ser88, Leu90, Leu100.

The inventors have observed that all the binding determinants located at the core of the knuckle are invariant between the BMPs, in particular, S88 at the center is highly conserved (Weber et al., 2007). This explains why targeting this region renders antibodies which bind to the knuckle of BMP4 crossreactive to other members of the BMP family.

Using Haddock modeling, the inventors have found out that the heavy chain CDR1 and CRD2 are important for binding. In a preferred embodiment of the antibody capable of binding to said knuckle as described above, said antibody comprises a heavy chain CDR1 consisting of the amino acid sequence of SEQ ID NO: 8 or a sequence not differing more than 1 amino acid thereof and a heavy chain CDR2 consisting of the amino acid sequence of SEQ ID NO:9, or a sequence not differing more than 1 amino acid thereof. Without wishing to be bound by theory, the inventors believe that these CDRs are important for the binding interaction with the knuckle of BMP4. Said antibody preferably further comprises a heavy chain CD R3 consisting of the amino acid sequence of SEQ ID NO: 10 or a sequence not differing more than 1 amino acid thereof. In a highly preferred embodiment, said antibody comprises the amino acid sequence of SEQ ID NO: 14.

In an alternative embodiment Gly5 of SEQ ID NO:8 may be substituted by Ser. Preferably, the antibody which binds to the hydrophobic pocket of BMP4 comprising the amino acid sequence of SEQ ID NO: 14 or a sequence at least 70%, more preferably 71, 72, 73, 74, 75, 80, 85, 90, 91, 92, 93, 94, 95, 96, 97, 98, 99, or 100% identical thereto. The inventors have found that Glu1 of SEQ ID NO: 14 may be substituted by Gln or Asp, Gly30 by Ser and Gly59 by Ser without detrimental effect.

Production of Antibodies of the Invention

The antibody of the invention may be produced by any method known in the art. Various procedures known in the art may be used for the production of polyclonal antibodies which can bind to said epitope. For production of the antibodies, various host animals can be immunized by injection with a BMP4 protein or a BMP4 polypeptide fragment bound to a suitable carrier. Suitable carriers can include, but are not limited to, BSA (bovine serum albumin), KLH (keyhole limpet hemocyanin), OVA (ovalbumin), THY (Thyroglobulin) and RSA (rabbit serum albumin). The host animal is preferably immunized with a BMP4 polypeptide comprising residues of BMP4 (SEQ ID NO:1), or a sequence at least 85%, preferably at least 90% identical thereto. Preferably, the host animals can be immunized by injection with a BMP4 protein or a polypeptide comprising any of the epitopes of BMP4 or residues thereof as defined above. In a preferred embodiment, said BMP4 protein or polypeptide comprises at least 6, more preferably 7, 8, 9, 10, 11, 12, 13, 14 residues selected from residues 10-17, 24-31, 45-72, 89, 91, 101, 103, 104, and 106 of BMP4. Preferably, BMP4 protein or polypeptide comprises 10-17, 45-56, and 69 of BMP4. In another embodiment, said BMP4 protein or polypeptide comprises one residue selected from the group consisting of Lys10, Asn11, Lys12, Asn13, Cys14, Arg15, Arg16, and His17, at least one residue selected from the group consisting of Gly45, Asp46, Cys47, Pro48, Phe49, Pro50, Leu51, Ala52, Asp53, His54, Leu55 and Asn56, and Ser69 of BMP4. In another embodiment, said BMP4 protein or polypeptide comprises at least the residues at least Lys12, Arg15, Asp46, and Pro50 of BMP4. In another embodiment, said BMP4 protein or polypeptide comprises residues 15, 49, 50, 51, 52, 53, 54 and 69 of BMP4.

In another embodiment, said BMP4 protein or polypeptide comprises at least at least 6, more preferably 7, 8, 9, 10, 11, 12, 13, 14 residues selected from residues 24-31, 57-68, 70-72 89, 91, 101, 103, 104 and 106 of BMP4. Preferably at least at least 6, more preferably 7, 8, 9, 10, 11, 12, 13, 14 residues selected from the group consisting of Ser24, Asp25, Val26, Gly27, Trp28, Asn29, Asp30, Trp31, at least one residue selected from the group consisting of Ser57, Thr58, Asn59, His60, Ala61, Ile62, Val63, Gln64, Thr65, Leu66, Val67, and Asn68, at least one residue selected from the group consisting of Val70, Asn71 and Ser72, at least one residue selected from the group consisting of Tyr103 and Gln104, and Met89, Tyr91, Lys101, and Met106 of BMP4. In another embodiment, said BMP4 protein or polypeptide comprises further Asp30, Trp31, Leu66 and Lys101 of BMP4.

In another embodiment, said BMP4 protein or polypeptide comprises at least 6, more preferably 7, 8, 9, 10, 11, 12, 13, 14 residues selected from residues 34, 35, 39, 86-88, 90, 97, 98, 100, 102 and 109 of BMP4. In another embodiment, said BMP4 protein or polypeptide comprises further Ala34, Gln39, Ser88, Leu90, Leu100 of BMP4.

Monoclonal antibodies may be made using the hybridoma method widely known in the art (see e.g., Kohler et al., Nature, 256:495, 1975) or may be made by recombinant DNA methods (e.g., as in U.S. Pat. No. 4,816,567) or other methods available in the art. Generally, a hybridoma can be produced by fusing a suitable immortal cell line (e.g., a myeloma cell line such as SP2/0) with antibody producing cells of the immunized animal. The antibody producing cell, preferably those of the spleen or lymph nodes, are obtained from animals immunized with the antigen of interest. The fused cells (hybridomas) can be isolated using selective culture conditions, and cloned by limiting dilution. Culture medium in which hybridoma cells are growing is assayed for production of monoclonal antibodies directed against the antigen. Preferably, the binding specificity of mabs produced by hybridoma cells is determined by immunoprecipitation or by an in vitro binding assay, such as radioimmunoassay (RIA) or ELISA. Cells which produce antibodies with the desired binding properties can be selected by a suitable screening assay. Methods for such isolation and screening are well known in the art.

Other suitable methods of producing or isolating antibodies which bind within said epitope of BMP4, including human or artificial antibodies, can be used, including, for example, methods which select a recombinant antibody (e.g., single chain Fv or Fab) from a library, or which rely upon immunization of transgenic animals (e.g., mice) capable of producing a repertoire of human antibodies (see e.g., Jakobovits et al., Proc. Natl. Acad. Sci. USA, 90:2551-2555, 1993; Jakobovits et al., Nature, 362:255-258, 1993; Lonberg et al., U.S. Pat. No. 5,545,806; Surani et al., U.S. Pat. No. 5,545,807).

Selection of antibody fragments from libraries using enrichment technologies such as phage-display (Matthews D J and Wells J A. Science. 260:1113-7, 1993), ribosome display (Hanes, et al., Proc. Natl. Acad. Sci. (USA) 95:14130-5, 1998), bacterial display (Samuelson P., et al., Journal of Biotechnology. 96:129-54, 2002) or yeast display (Kieke M C, et al., Protein Engineering, 10:1303-10, 1997) has proven to be successful alternatives to classical hybridoma technology (see for example: Little M. et al., Immunology Today, 21:364-70, 2000).

Methods of producing antibodies binding to a specific conformational epitope are known in the art. For example, homologous sequences to the sequences taught herein may be generated using Deep sequencing (Next Generation Sequencing (NGS)) of the VHH repertoire of the llama from which the antibodies were isolated can generate homologs of the antibodies. It will even lead to following of the mutations led to the maturation process of the VHH by identifying the intermediate sequences (as described in McCoy et al, Plos Pathogens 10, e1004552, 2014).

Variant antibodies of the invention may suitably be generated by screening Family specific libraries. By designing a degenerated primer based on the last amino acids of the variable CDR3 of the antibodies as described herein and use it together with a primer annealing to FR1 to generate a sublibrary from the RNA of the llama used to select the family members of the antibodies described herein, present in the VHH repertoire will be amplified. Selection from such family libraries in the same conditions described herein, will yield a VHH that binds to the same epitope (ref. Koh et al J. Biol. Chem. 285; 19116-19124, 2010).

Methods of verifying whether an antibody binds to an epitope are known in the art Suitably, to verify whether a certain antibody binds to a specific conformational epitope, epitope mapping is combined with docking or structure determination as described herein. The epitope targeted by any VHH binding to BMP4 may be tested by competition with for example the C4 or C8 antibodies described herein. Docking, Pepscan or ultimately, structure determination of VHH-BMP4 co-crystals, may be used to determine precisely the site of binding.

Variant Antibodies

Any antibody (preferably a murine monoclonal antibody, rabbit, goat, llama or a human antibody (produced e.g., in a transgenic mouse)) raised against said epitope of the invention or against a protein comprising an immunogenic epitope of the invention is a parent antibody. Said parent antibody may be further altered to create a chimeric or humanized form of the antibody using methods well known in the art Such chimeric or humanized antibodies, may serve as parent antibodies for further variation or mutagenesis. Parent antibodies of the invention may be further mutagenized e.g., within the CDR domain(s) to create a variant antibody with an optimized property of interest, e.g., binding affinity, IC50, specificity, etc. An amino acid substitution variant antibody is preferred and has at least one amino acid residue of the parent antibody molecule removed and a different residue inserted in its place. The sites of greatest interest for substitutional mutagenesis include the CDR regions, but FR alterations are also contemplated. Conservative amino acid substitutions are preferred. If such substitutions result in a change in a biological activity of the antibody; then more substantial changes, i.e., non-conservative amino acid changes, may be introduced and the products screened.

A convenient way for generating substitutional variants is affinity maturation using phage display. Briefly, several CDR region sites are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity, specificity, IC50) as herein disclosed. In order to identify candidate CDR region sites for modification, alanine scanning mutagens can be performed to identify CDR region residues contributing significantly to antigen binding. Alternatively, or in addition, it may be beneficial to analyze a crystal structure of the antigen-antibody complex to identify contact points between the antibody and BMP4. Such contact residues and neighboring residues are candidates for substitution according to the techniques elaborated herein or known in the art. Alternatively, or in addition, random mutagenesis may be performed on one or more CDR sequences at one or more residue positions, either while the CDR is operably linked to the variable region or while the CDR is independent of other variable region sequence and then the altered CDR returned to a variable region using recombinant DNA technology. Once such variant antibodies are generated and expressed, the panel of variants is subjected to screening as described herein and antibodies with superior properties in one or more relevant assays may be selected for further development.

Any cysteine residue not involved in maintaining the proper conformation of an anti-BMP4 antibody of the invention may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the parent antibody.

Glycosylation of antibodies or antigen binding fragments thereof is typically either N-linked or O-linked. N-linked refers to the attachment of the carbohydrate moiety to the side chain of an asparagines residue. The tripeptide sequence asparagines-X-serine and asparagines-X-threonine, where X is any amino acid except praline, are the recognition sequences for enzymatic attachment of the carbohydrate moiety to the asparagines side chain. Thus the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

An antibody according to the invention is preferably a single-domain antibody. The single-domain antibody may be of camelid origin, and thus may be based on camelid framework regions; alternatively, the CDR may be grafted onto other antibody domains, for example but not limited to VNAR or human VHH framework regions. In a preferred aspect of the invention, said antibody of the invention is a single-domain antibody, preferably a VHH. Their smaller size and their ability to reach protein hidden grooves renders them highly effective at providing BMP-specific inhibition. The use of single-domain antibody is also advantageous as they may be produced easily and inexpensively in large quantities, as opposed to antibodies produced from hybridoma cell lines. Additionally, hybridoma lines may be unstable and decrease antibody expression levels over time. Single-domain antibodies or binding fragments are also advantageous for molecular imaging applications due to their short plasma half-life, which achieves fast contrast-to-noise ratio needed for imaging.

Preferably, the antibody of the invention is a humanized antibody. An advantage thereof is that humanized antibodies are less immunogenic when used in humans.

An antibody having VH regions having high (i.e., 80% or greater) homology to the VH region of the sequences set forth above, can be obtained by mutagenesis (e.g., site-directed or PCR-mediated mutagenesis) of nucleic acid molecules encoding SEQ ID NOs:11, 12 and 14, followed by testing of the encoded altered antibody for retained function using the assays described herein.

In another preferred embodiment, said antibody may have a substantially identical sequence to SEQ ID NO:11, 12 or 14. A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides.

Conservative amino acid mutation may include addition, deletion, or substitution of an amino acid; in one non-limiting example, the conservative amino acid mutation is a conservative amino acid substitution. A conservative amino acid substitution is defined herein as the substitution of an amino acid residue for another amino acid residue with similar chemical properties (e.g. size, charge, or polarity).

A conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (H is or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or 1), phenylalanine (Phe or F), valine (Val or V), leucine (Leu or L), tryptophan (Trp or W), methionine (Met or M), alanine (Ala or A), and glycine (Gly or G).

"Acidic amino acid" refers to hydrophilic amino acids having a side chain pK value of less than 7, which are typically negatively charged at physiological pH. Acidic amino acids include glutamate (Glu or E), and aspartate (Asp or D).

The substantially identical sequences of the present invention may be at least 70% identical; in another example, the substantially identical sequences may be at least 70, 71, 72, 73, 74, 75, 80, 85, 90, 91, 92, 93, 94, 95, 96, 97, 98, 99, or 100% identical at the amino acid level to sequences described herein. Importantly, the substantially identical sequences retain the activity and specificity of the reference sequence. As would be known to one of skill in the art, amino acid residues of an antibody, particularly within the framework regions may be mutated (substituted or deleted) without affecting the functional properties of the antibody (antigen recognition and binding).

Multimeric Antibodies

The invention further relates to a multimeric antibody comprising at least one antibody according to the invention. Said multimeric antibody preferably comprises at least 2 antibodies thereof according to the invention. An advantage thereof is that such multimeric antibodies have a higher affinity for the epitope as defined herein.

In a preferred embodiment of the multimeric antibody of the invention, said multimeric antibody is a homodimer of the antibody of the invention. More preferably said antibody is a single-domain antibody, more preferably a VHH. An advantage of said homodimer, is its high affinity to BMP4 (KD=9.7 pM), which is 10 times higher than that of Noggin (KD=91 pM, Table 1) and 70 times higher compared to BMPR1a (KD=635 pM). Additionally, its inhibitory effect on the BMP4 downstream signaling and subsequent transcriptional inhibition proved to be akin to those of Noggin (FIG. 13A).

Preferably, said multimeric antibody comprises at least one, more preferably at least two antibody of the invention. In a preferred embodiment, said multimeric antibody comprises at least two of said antibodies capable of binding to the hydrophobic groove of wrist of BMP4 as described above. An advantage thereof is that the multimeric antibody according to this embodiment has an improved affinity for BMP4 and also has an improved inhibitory effect on BMP4 signaling. Said multimeric antibody of this embodiment, as exemplified by the C4C4 as described in the example, proved to have a very high affinity to BMP4 (KD 9.7 pM) which is 10 times higher than that of Noggin (KD 91 pM) and 70 times higher compared to BMPR1a (KD 635 pM). Consequently, it exhibits a highly potent neutralizing activity for BMP4 signaling. In contrast to Noggin, the multimeric antibodies according to this embodiment do not affect signaling of the highly homologous BMP2 and of other BMPs including BMP5,6, and 7.

In another embodiment, said multimeric antibody comprises at least two of said antibodies capable of binding to the hydrophobic pocket of the wrist of BMP4 as described above. An advantage thereof is that such multimeric antibody has an improved affinity for BMP4 and BMP2 and also has an improved inhibitory effect on BMP4 as well as BMP2 signaling. In addition, such multimeric antibody have an ability to significantly abrogate BMP activity, almost to the level of Noggin. In particular, low doses of multimeric antibodies according to this embodiment were shown to be as effective as Noggin in maintaining intestinal cell cultures. Since recombinant Noggin is expensive, multimeric antibody according to this embodiment may represent a cheaper alternative for these types of cultures.

In another embodiment, said multimeric antibody comprises at least one antibody capable of binding to the knuckle of BMP4 as described above and one antibody capable of binding to the hydrophobic pocket of BMP4 as described above. An advantage thereof is that such multimeric antibody has an ability to significantly abrogate BMP activity, to the level of Noggin. The multimeric antibody according to this embodiment binds and presents a slight effect on BMP5 activation (FIG. 13C).

Methods of producing multimeric antibodies are known in the art and described for instance in EP 1293514 A1 and WO 1994004691 A2.

In another embodiment, said multimeric antibody comprises at least one of said antibodies of the invention and one antibody binding to a serum protein, including, but not limited to albumin or IgG. An advantage thereof is that such multimeric antibody has a prolonged halflife in serum which could enhance the therapeutic effects.

In another embodiment, said multimeric antibody comprises at least one of said antibodies of the invention and one antibody serving as a transporter over barriers, such as the proinflammatory peptide substance P. An advantage thereof is that such multimeric antibody can be delivered orally or nasally for delivery in the blood.

In another embodiment, said multimeric antibody comprises at least one of said antibodies of the invention and a therapeutic agent, including but not limited to a therapeutic Ig-like domain, a toxic protein or peptide, a radioactive substance. An advantage thereof is that such multimeric antibody has an enhanced therapeutic effect.

The multimeric antibody of the invention may be produced by any suitable method known in the art. For example, and without wishing to be limiting in any manner, multimerization may be achieved using self-assembly molecules (Zhang et al, 2004; Merritt & Hol, 1995), as described in WO2003/046560. The described method produces pentabodies by expressing a fusion protein comprising the antibody of the present invention and the pentamerization domain of the B-subunit of an AB5 toxin family (Nielson et al, 2000); the pentamerization domain assembles into a pentamer, through which a multivalent display of the antibody is formed. Each subunit of the pentamer may be the same or different. Additionally, the pentamerization domain may be linked to the antibody or antibody fragment using a linker; such a linker should be of sufficient length and appropriate composition to provide flexible attachment of the two molecules, but should not hamper the antigen-binding properties of the antibody. In one non-limiting example, the linker may be the GS linker as described herein.

Other forms of the multimeric antibody of the invention are also encompassed by the present invention. For example, and without wishing to be limiting, the antibody may be presented as a dimer, a trimer, or any other suitable oligomer. This may be achieved by methods known in the art, for example direct linking connection (Nielsen et al, 1996), c-jun/Fos interaction (de Kruif et al, 1996), "Knob into holes" interaction (Ridgway et al, 1996).

Another method known in the art for multimerization is to dimerize the antibody using a Fc domain. In this approach, a Fc gene inserted into an expression vector; the nucleotide sequence of the antibody can be amplified and inserted into the vector such that the C-terminus of the antibody is linked to the hinge region of the Fc without addition of extra residues. The resulting vector can be transfected to cells and the fusion protein may be recombinantly expressed, then purified by affinity chromatography (for example, on a protein A column). One non-limiting example of such a method of multimerization is described by Bell et al (2010) and Iqbal et al (in press). Techniques for implementing such dimerization would be known to those of skill in the art.

Preferably, the antibody according to the invention is bound to another antibody using a linker. In a preferred embodiment, said linker comprises at least 10 amino acids. In a preferred embodiment, said linker comprises two consecutive peptide spacers, each having the amino acid sequence GGGGS. In a highly preferred embodiment, said multimeric antibody is a homodimer, preferably comprising SEQ ID NO:11, 12 or 14.

Within some embodiments, such the antibody according to the invention comprising one or more heavy chain CD R3 domain from a non-human antibody (a) are capable of competing for binding with; (b) retain the functional characteristics; (c) bind to the same epitope; and/or (d) have a similar binding affinity of the corresponding parental non-human antibody.

Antibodies that Bind to the Same Epitope as Antibodies of the Invention

In another embodiment, the invention provides antibodies that bind to the same epitope of BMP4 as any of the antibodies of the present invention (i.e. antibodies are provided that have the ability to cross-compete for binding to the BMP4 epitopes as taught herein). In some embodiments, the reference antibody for cross-competition studies can be an antibody according to the present invention. Such cross-competing antibodies can be identified based on their ability to cross-compete with an antibody disclosed herein in standard binding assays.

Imaging Agents

The present invention also encompasses a molecular imaging agent comprising an antibody in accordance with the present invention linked to a detectable agent. For example, the antibody of the invention may be linked to a radioisotope, a paramagnetic label such as gadolinium or iron oxide, a fluorophore, Near Infra-Red (NIR) fluorochrome or dye, an echogenic microbubble, an affinity label (for example biotin, avidin, etc), enzymes, or any other suitable agent that may be detected by diagnostic imaging methods. In a specific, non-limiting example, the antibody may be linked to a near infrared fluorescence (NIRF) imaging dye, for example and not wishing to be limiting Cy5.5, Alexa680, Dylight680 or Dylight800.

The antibody of the present invention may also comprise additional sequences to aid in expression, detection, or purification of the antibody. For example, and without wishing to be limiting, the antibody may comprise a targeting or signal sequence (for example, but not limited to ompA), a detection tag (for example, but not limited to c-Myc), a purification tag (for example, but not limited to a histidine purification tag, HHHHHH), or any combination thereof. In a preferred embodiment, the antibody comprises at the C terminal an amino acid sequence [linker] that contain at least one reactive Cys or one Lys or a combination of these amino acids to which various labels can be coupled to render these molecules suitable for imaging, for instance for non-invasive imaging using techniques like MRI, PET, SPECT or optical imaging.

Pharmaceutical Compositions

In another aspect, the present invention used a composition, e.g., a pharmaceutical composition, containing one anti-BMP4 antibody or a combination of anti BMP4 antibodies or antigen-binding portion(s) thereof, preferably the antibodies as taught herein, formulated together with a pharmaceutically acceptable carrier. Pharmaceutical compositions comprising antibodies binding to BMP4 or antigen binding portions thereof are well known in the art and are described in more detail for example in WO2008030611. Their use against SMAD4 deficient tumors was, however, not disclosed before the present invention. Such compositions may include one or a combination of (e.g., two or more different) antibodies or a multimeric antibody. Suitably, an antibody or multimeric antibody of the invention is used. Pharmaceutical compositions of the invention also can be administered in combination therapy, i.e. combined with other agents. For example, the combination therapy can include an anti-BMP4 antibody, preferably as taught herein, combined with at least one other anti-inflammatory or immunosuppressant agent. As used herein, "pharmaceutically acceptable carrier" includes any and all solvents, dispersion media, coatings, antibacterial and antifungal agents, isotonic and absorption delaying agents and the like that are physiologically compatible. Typically, the carrier is suitable for intravenous, intramuscular, subcutaneous, parenteral, spinal or epidermal administration (e.g., by injection or infusion). Depending on the route of administration, the active compound, i.e. antibody, or antigen binding fragment thereof or multimeric antibody of the invention, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge et al, J. Pharm. ScL 66:1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol and the like; and (3) metal chelating agents, such as citric acid, ethylenediamine tetraacetic acid (EDTA), sorbitol, tartaric acid, phosphoric acid and the like.

Examples of suitable aqueous and nonaqueous carriers that may be employed in the pharmaceutical compositions of the invention include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of presence of microorganisms may be ensured both by sterilization procedures, supra and by the inclusion of various antibacterial and antifungal agents, for example, paraben, chlorobutanol, phenol sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art Except insofar as any conventional media or agent is incompatible with the active compound, use thereof in the pharmaceutical compositions of the invention is contemplated. Supplementary active compounds can also be incorporated into the compositions. Therapeutic compositions typically must be sterile and stable under the conditions of manufacture and storage. The composition can be formulated as a solution, microemulsion, liposome or other ordered structure suitable to high drug concentration. The carrier can be a solvent or dispersion medium containing, for example, water, ethanol, polyol (for example, glycerol, propylene glycol and liquid polyethylene glycol and the like) and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, typically from about 0.1 percent to about 70 percent, most typically from about 1 percent to about 30 percent of active ingredient in combination with a pharmaceutically acceptable carrier.

In preferred embodiment, the pharmaceutical composition may further comprise an anti-cancer drug.

Anti-cancer drugs, such as platinum complexes are known to be useful for the treatment of different kinds of cancers. Exemplary kinds of cancer include, but are not limited to lung cancer, testicular cancer, breast cancer, colon cancer, ovarian cancer, head and neck cancer, esophageal cancer or gastric cancer. All of these cancer types are known to be treatable with anti-cancer drugs based on or including platinum complexes and are also known to develop resistances against the anti-cancer drugs used to treat these types of cancers.

In a preferred embodiment, said anti-cancer drug comprises platinum complexes. In a preferred embodiment, a specific anti BMP4 antibody is used in combination with cisplatin. In another preferred embodiment, said specific specific anti BMP4 antibody is an antibody which binds within residues 10-17, 45-56, and 69 of SEQ ID NO:1 or a n antibody that competes with said antibody.

Medical Use of BMP4 Antibodies

Due to advantages mentioned above, antibodies according to the invention are highly suitable for use in a medical treatment of a subject wherein BMP4 mediated signaling needs to be inhibited. The invention therefore further relates to the antibodies, multimeric antibodies or compositions as defined herein, for medical use. Said antibodies, multimeric antibodies and compositions have numerous in vitro and in vivo diagnostic and therapeutic utilities involving the diagnosis and treatment of BMP4 mediated disorders. Medical uses of anti-BMP4/2 antibodies are known in the art and described for instance in WO2008030611. For example, these molecules can be administered to cells in culture, in vitro or ex vivo or to human subjects, e.g., in vivo, to treat, prevent and to diagnose a variety of disorders. These disorders are preferably treated, prevented or diagnosed with an antibody according to the present invention. As used herein, the term "subject" is intended to include human and non-human animals. The term "non-human animals" includes all vertebrates, e.g., mammals and non-mammals, such as non-human primates, sheep, dogs, cats, cows, horses, chickens, amphibians and reptiles. Preferred subjects include human patients having disorders mediated by BMP4 activity. The methods are particularly suitable for treating human patients having a disorder mediated by BMP4 expression or function. In some embodiments, said human patients suffer from a SMAD4 deficient tumor. When antibodies to BMP4 are administered together with another agent, the two can be administered either in order or simultaneously.

Given the specific binding of the antibodies of the invention for BMP4, the antibodies of the invention can be used to specifically detect BMP4 expression by cells and tissues, and moreover, they can be used to purify BMP4 via immunoaffinity purification.

BMP4 is associated with a variety of diseases involving inflammation and abnormal bone formation and ossification. These diseases include Spondyloarthritides (SpA) diseases that, together, are characterized by spinal inflammation, significant pain, and functional disability. SpA diseases include, for example, ankylosing spondylitis, psoriatic spondyloarthritides, reactive spondyloarthritides, spondyloarthritides associated with inflammatory bowel disease, and undifferentiated spondyloarthritides. In particular anti-BMP4 antibody, multimeric antibody or composition as defined herein of the present invention may be effective in the treatment of ankylosing spondylitis (AS), other spondyloarthropathies, and related inflammatory rheumatic diseases, which are typically characterized by inflammatory back pain, usually caused by sacroiliitis and enthesitis. Thus, the invention encompasses methods of treating the aforementioned diseases comprising administering an antibody, multimeric antibody or composition according to the invention herein to a subject.

Furthermore, these antibodies may even have the potential for clinical diagnostic and therapeutic use in certain diseases in which BMP4 but no other BMPs might play a specific pathogenic role, such as glomerulosclerosis (Tominaga et al. 2011) and hypoxic pulmonary hypertension (Anderson et al., 2010). Therefore, in a highly preferred embodiment an antibody, multimeric antibody or composition as provided herein is used in the treatment of diseases in which BMP4 but no other BMPs might play an specific pathogenic role, more preferably in the treatment of glomerulosclerosis.

Furthermore, antibodies of the invention which not only inhibit BMP4 but also BMP2 (such as antibodies binding to the hydrophobic pocket of the wrist of BMP4), but also BMP2, 5 and 6 (such as antibodies binding to the knuckle of BMP4), can also be used in diseases where multiple BMPs play a pathogenic role in disease development. For example, indiscriminate BMP inhibition by promiscuous chemical inhibitors has been proven to be effective to reduce metastasis in mammary (Owens et al 2014), Lung (Haio et al 2014) and prostate cancer (Leet et al 2011). They have also been proven effective at preventing endothelial dysfunction and osteogenic differentiation in chronic kidney disease (Kajimoto et al 2014) as well as decrease vascular inflammation, calcification and osteogenic activity in arthrosclerosis (Derwal et al 2012). Natural inhibitors, such as Noggin, have also been proven effective in heterotopic ossification (Yu et al 2008) and reducing lung cancer proliferation (Feeley et al 2006). However, due to their off-target effects, such as inhibition of other signaling pathways such as TGFβ or wnt, their therapeutic potential is arguable. For instance, indiscriminate inhibition of BMP function can activate dormant metastatic breast tumour cells (Gao et al., 2012) or increase colonic tumour burden in vivo (Whissell et al., 2014). Several other studies have further argued the clinical potential of such inhibitors (Vogt et al., 2011).

Because antibodies according to the present invention are provided that have a higher affinity than Noggin, and also present less off-target effects, they are better suited to overcome the limitations that affect the clinical and research applications of current BMP inhibitors.

The present invention also encompasses nucleic acid molecules encoding the antibodies as described herein. The sequence of said nucleic acid molecule may be codon-optimized. The present invention also encompasses vectors comprising the nucleic acids as just described.

The above disclosure generally describes the present invention. Unless defined otherwise, all technical and scientific terms used herein have the same meaning as those commonly understood by one of ordinary skill in the art to which this invention belongs. A more complete understanding can be obtained by reference to the following specific examples which are provided herein for purposes of illustration only, and are not intended to limit the scope of the invention.

EXAMPLE SECTION

Example 1: Immunization

Recombinant BMP4 was purchased from R&D systems and treated according to the manufacturer protocol. BMP4 was dissolved in 4 mM HCl at 0.1 mg/ml and 50 µg was diluted in PBS (1 ml), mixed with 1 ml adjuvant Stimune and injected intramuscular in two llamas (llama#18-2 and llama#31-2) according to the following schedule: Immunizations on day 0, day 14, day 28 and day 35. Blood was taken at day 0 (preimmune) and day 43 (immune). Large blood uptake at day 43 was used for PBL isolation and RNA extraction.

Immune Responses

Figure 1B:
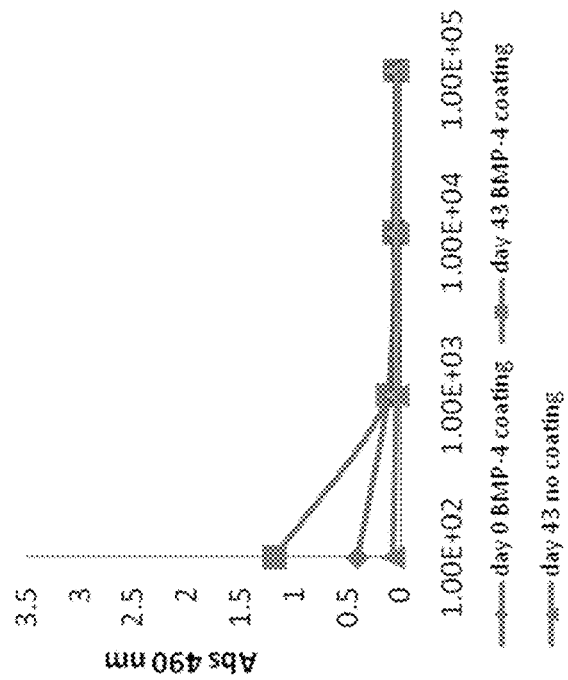

Immune responses directed against BMP4 were measured in the serum taken at day43 (end of immunizations and PBL isolation) and compared to signal measured in serum of day 0 (preimmune). BMP4 was coated at 200 ng/well of a Maxisorp plate and ELISA was performed with serial dilutions of preimmune serum (day0) and immune serum (day43). Immune sera of both llama showed binding to immobilized BMP4 in contrast to preimmune sera (FIG. 1). Measured signal for immune sera is specific as no signal was detected in non-coated well (FIG. 1). The signal measured is only heavy chain antibody response since a polyclonal anti-VHH (K976) was used for detection.

Example 2: Library Constructions

Construction of VHH Libraries

Figure 3:
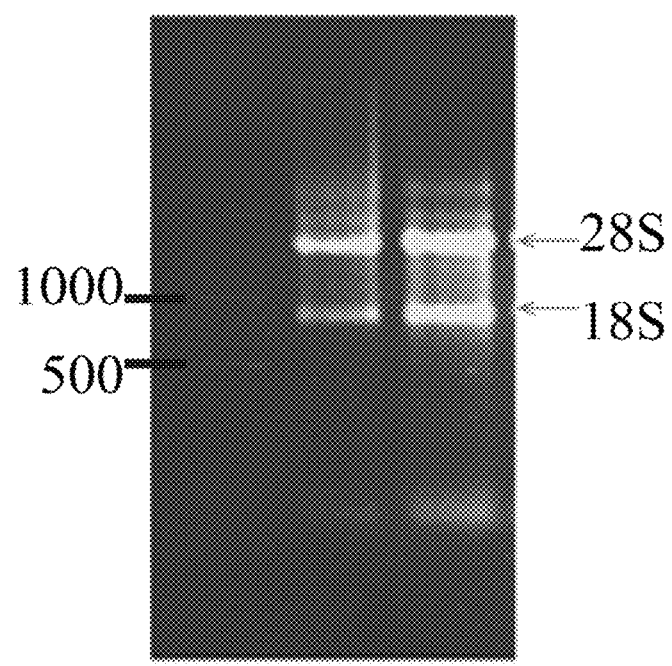
FIG. 3 shows the quality of the RNA samples isolated from the PBLs of llama#18.2 and #31.2. Blood taken at day 43 was stratified on a Ficoll gradient (GE Health care) and lymphocyte band was selected, washed with PBS, then cell were lyzed and RNA was purified through 2 cycle of phenol-chloroform-isoamyl alcohol extraction. Finally RNA was precipitated and concentration measured at 260 nm. 5 µl RNA samples were analyzed on 1% TBE agarose gel to assess its quality. The 28S and 18S ribosomal RNA bands are clearly visible confirming RNA integrity.

RNA was isolated from the lymphocytes purified from blood taken on day 43. Blood was layered on a Ficoll gradient and centrifuged. Lymphocytes layer was isolated, washed and lysed. RNA was extracted with phenol: chloroform: isoamylalcohol. RNA concentrations were measured at 260 nm and quality of the RNA was assessed by gel electrophoresis (FIG. 3).

Figure 2:
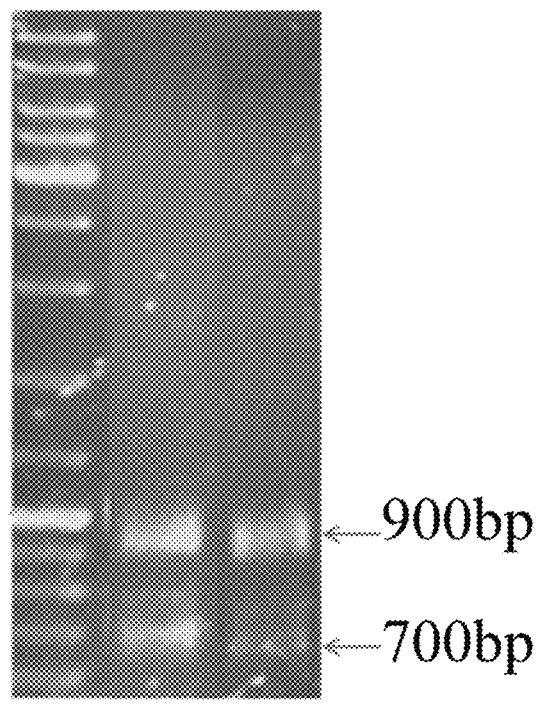
FIG. 2 shows the specific amplification of VH and VHH fragments from reverse transcribed RNA. About 40 µg of RNA was reverse transcribed into cDNA and used as template for PCR to amplify VH and VHH regions of classical IgG and heavy chain only IgG using primers annealing at the leader peptide site and at CH2 domain. Two DNA fragments are visible on gel, corresponding to VHH (700 pb) and VH (900 bp) due to the lack of CH1 domain in heavy chain antibodies. The 700 bp fragment was cut from the gel and purified. About 80 ng was used as a template for nested PCR to introduce a SfiI site at the 5'.

About 40 µg RNA was transcribed into cDNA using reverse transcriptase Kit (Life Technologies). The cDNA was cleaned on Macherey Nigel PCR cleaning columns. IG H (both conventional and heavy chain) fragments were amplified using primers annealing at the leader sequence region and at the CH2 region. Two DNA fragments (~700 bp and 900 bp) were amplified representing the VHH and VH, respectively (FIG. 2).

Figure 4:
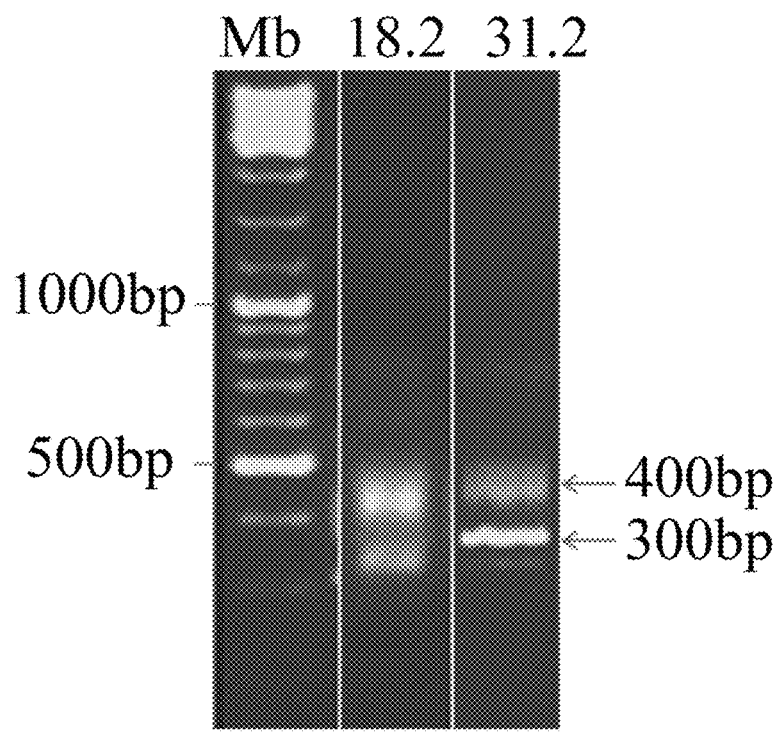
FIG. 4 shows a digestion of the VHH fragments prior to cloning. Amplified 700 pb fragments were digested with BstEII (a restriction site present just before the linker between variable domain and constant domain of IgG), resulting in the collapse of the 700 bp fragment into fragments of approximate 300 and 400 bp. The reaction mixture was further digested with SfiI prior to the isolation of the 400 bp fragments from gel and cloning into the plasmid pUR8100.

The amplified VHH fragment was cut from the gel and extracted using Macherey Nigel columns. Subsequently, a nested PCR was applied to introduce a SfiI site at the 5' of the 700 bp fragment. The generated PCR fragments were cleaned using Marcherey Nigel columns and eluted DNA were subsequently digested with BstEII (internal restriction site in IG H) and SfiI. Digested DNA was separated on an agarose gel and the 400 bp fragment was isolated from gel (FIG. 4).

Figure 5:
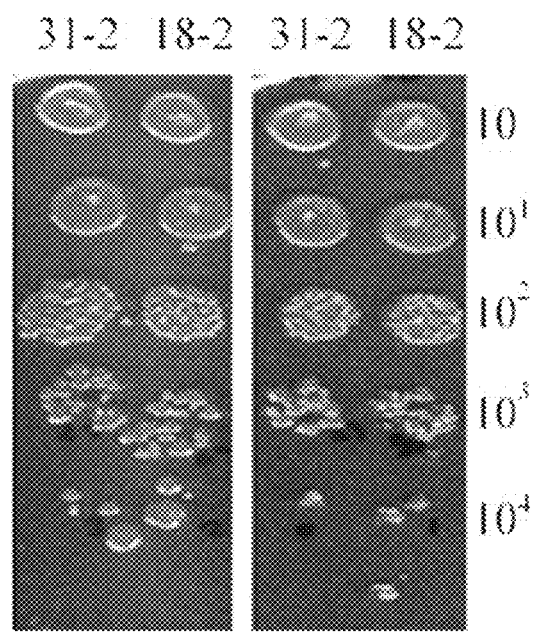
FIG. 5 shows the number of E. coli bacteria transformed with a ligation of 330 ng of 400 bp fragments into 1 μg of pUR8100. Competent E. coli strain TG was transformed with the ligation mixture through electroporation. Number of transformants was calculated from 10-fold titration of the transformation, spotting onto LB-agar supplemented with 100 μg/ml ampicillin and 2% glucose and counting of the ampicillin resistant colonies. Spotting was in duplicate and the number of colonies was average of the 2 spottings.

The purified 400 bp fragments (~330 ng) were ligated into the phagemid pUR8100 (~1 µg) and transformed into TG1. The numbers of transformants (=size of the VHH libraries) were calculated from dilutions of the rescued TG1 culture (FIG. 5). Libraries size was ~2×10$^7$ for both libraries.

The insert frequency was determined by picking 12 random clones from each library and running colony PCR. The insert frequency was found to be 100%.

Example 3: Selections of Anti BMP4

Phage-Display Selection

Figure 6:
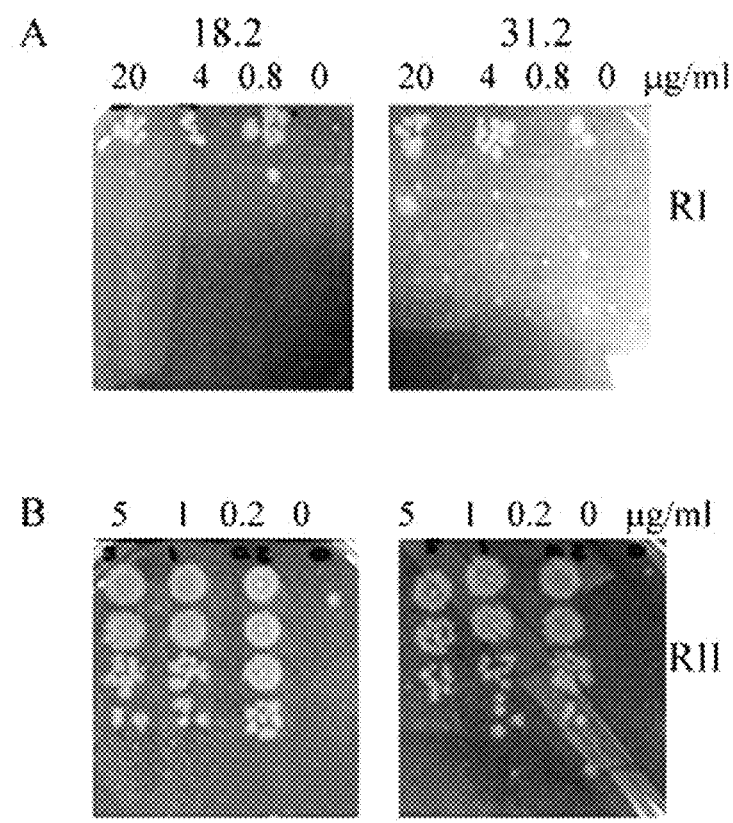
FIG. 6 shows the outputs of the 2 rounds of panning selection on immobilized BMP4. The amount of BMP4 coated into Maxisorp wells for the $1^{st}$ round of selection (RI, A) was different from the amount of BMP4 coated in the $2^{nd}$ round (RII, B). BMP4 concentrations used for coating are indicated on top in μg/ml. Number of eluted phages were calculated from titration of the infected E. coli TG1 and spotting on LB agar supplemented with 100 μg/ml ampicillin and 2% glucose.

Two rounds of selections were needed to select anti-BMP-4. Whereas 1$^{st}$ round selection (RI) yielded only few binders and almost no enrichment of eluted phages compared to no antigen (FIG. 6A), 2$^{nd}$ round (RII) of selection on BMP-4 shows a much improved output and enrichment in the phage dilutions compared with RI (FIG. 6B).

Figures 7, 9:
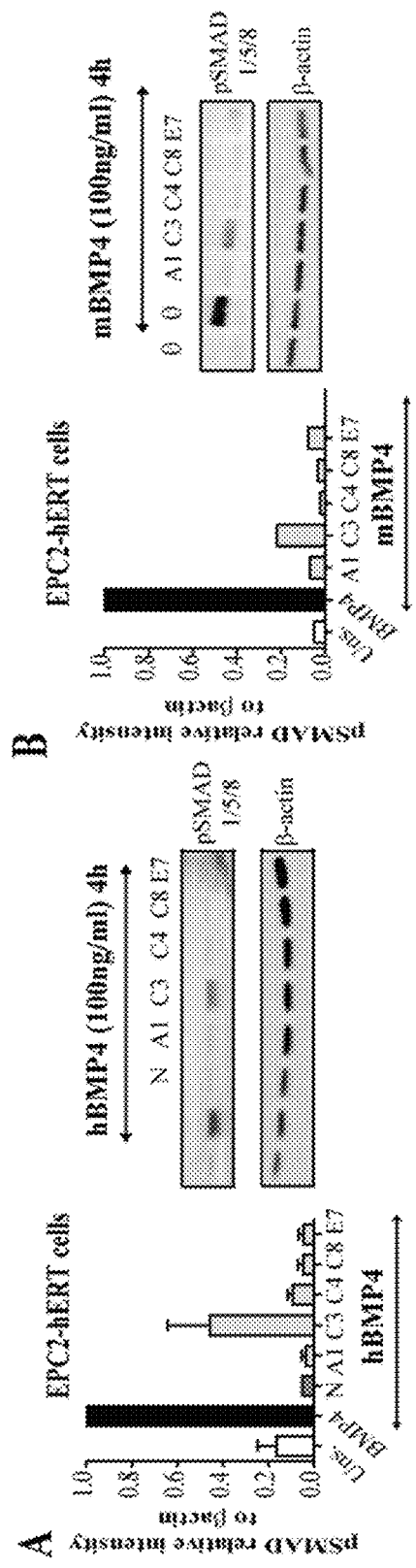
FIG. 7 shows binding of individual clones to immobilized BMP4 by ELISA. 47 single clones were picked from the output of RII on BMP4 coated at 0.2 μg/ml from library 18-2 (column 1-6) and from library 31-2 (column 7-12) of the master plate QVQ16. Wells H6 and H12 contained empty TG1 strain and will be used as negative controls. Bacteria containing the different VHH were grown at 37° C. and expression of the VHH was induced with Isopropyl β-D-1-thiogalactopyranoside (IPTG). VHH were extracted from disrupted bacteria and applied to wells coated with 200 ng/well of BMP4. After washing of unbound VHH, bound VHH were detected with anti-myc mAb 9E10 and a secondary anti-mouse coupled to peroxidase. The amounts of bound VHH were quantified by colorimetric conversion of ortho-phenylenediamine (OPD) in the presence of $H_2O_2$, which was measured at 490 nm.
FIG. 9 shows the functional characterization of the anti-BMP4 VHH antibodies. The Normal Esophageal Squamous Cell line EPC2-hERT was activated with 100 ng/ml of human (A) or mouse (B) BMP4 for 4 hours. VHH antibodies or human Noggin at a concentration of 5 μg/ml were added at the same time. Phosphorylation of SMAD1/5/8 was detected by western blot after cell lysis. Equivalent protein loading was confirmed by detection of β-actin. Band intensity was measured with the ImageJ program. Error bars represent standard deviations of the mean, calculated from 3 independent experiments.

Screening of Monoclonal VHH 47 single clones were picked from the outputs selected on 0.2µg/ml BMP4 from each library (library 18-2 columns 1 to 6; library 31-2 columns 7 to 12). Wells H6 and H12 contained E. coli TG1 containing empty plasmid. The clones were grown in deep-wells 96-wells plates and VHH production was induced with IPTG. The periplasmic fractions made from these clones were used to screen for binding to BMP4 with ELISA. Maxisorp plates were coated with BMP4 at 2 µg/ml. After blocking with 4% skimmed Milk in PBS (MPBS) for 1 hr, the plates were incubated with periplasm in 2% MPBS for 2 hrs. Bound VHH were detected with anti-VHH polyclonal antibody for 1 hr, followed by a secondary anti-rabbit coupled to a peroxidase. OPD was used for the final detection and the read-out with a plate reader at 490 nm. FIG. 7 shows the results of the VHH ELISA for BMP4 in which a several positive clones can be distinguished. More binders were found in library 18-2 compared to library 31-2 in concordance with the results of the immune response, where a slightly higher immune response was measured in the serum of llama 18-2 compared to llama 31-2.

Based on ELISA signal and HinfI finger print, 15 clones (9 clones from library 18-2 and 6 clones from library 31-2) were sequenced.

VHH A1, C3, C4, C8, E7 and F3 were chosen for production in large scales. VHH expression was induced with IPTG and purified from the periplasm using TALON. Purified VHH were analyzed with SDS-PAGE (FIG. 8A).

Figure 8:
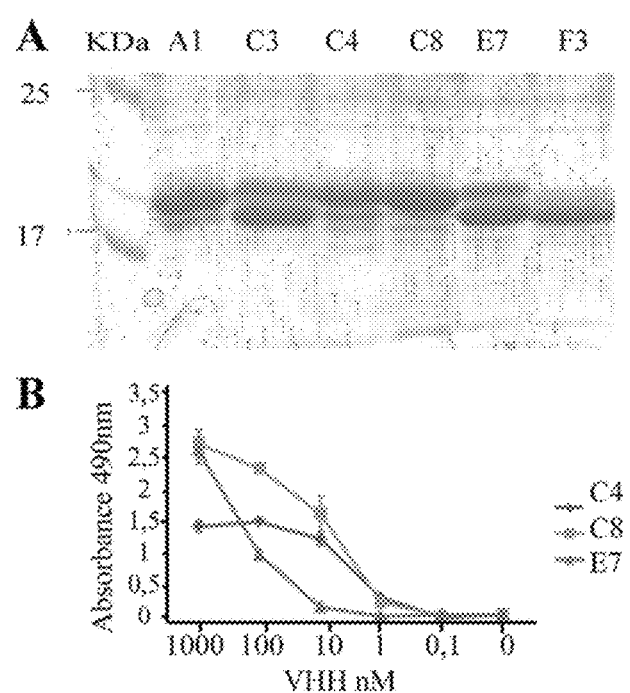
FIG. 8 shows purified anti-BMP4 VHH. VHH in wells A1, C3, C4, C8, E7 and F3 of master plate QVQ16 were selected for subcloning and large scale purification. A) Purified VHH were analyzed by SDS-PAGE and Coomassie staining. All the VHH were pure except for some minor processing of presumably the tags. B) Binding of purified C4, C8 and E7 to immobilized BMP4 was measured with titration ELISA. The apparent affinity of the 3 VHH is C8>C4>E7.

Binding of the VHH C4, C8 and E7 to immobilized BMP4 was measured in a dose-response ELISA to assess their apparent affinity (FIG. 8B). The apparent affinity of C8 appeared to be slightly higher than that of C4, whereas E7 appeared to show the lowest affinity of the 3 VHHs.

Example 4: Biheads Construction

Construction of Bi-Valent and Bi-Specific VHH Against BMP4

The DNA sequences of the VHHs C4, C8 and E7 were amplified using PCR. Different primers sets were designed to amplify the VHH. The primers at the 3' of the N-terminal VHH and at the 5' of the C-terminal VHH encoded two-times the repeat of the pentapeptide 'Gly-Gly-Gly-Gly-Ser' (GS-linker), or no pentapeptide. These same primers contain a unique restriction site (BamHI). Whereas the primer at 5' of the VHH located at the N terminus and the primer at the 3' of the C terminal VHH are plasmid encoded.

After PCR amplification, the generated fragments were digested with a unique N-terminal restriction site (SfiI) and BamHI for the VHH that will be located at the N terminus, and with BamHI and a unique C-terminal restriction site (BstEII) for VHH that will be located at the C terminus. The fragments are ligated into an expression vector, which was digested with SfiI and BstEII.

The following biheads: C4-homobihead, C8-homobihead and C8-E7 heterobihead, were constructed in 2 versions: One with linker length of 10 amino acids (two-times GS-linker) and another version with 20 amino acids (four-times GS linker)

The VHH-bihead constructed in this way may be produced in *E. coli* after IPTG induction. The formed bihead is secreted into the periplasm due to the presence of a PelB-signal sequence.

Example 5: In Vitro Activity

Anti-BMP4 VHHs Bind to and Inhibit BMP4-Mediated Signaling

To test whether these anti-BMP4 VHHs not only bind BMP4 but also inhibit its signaling, we tested their ability to inhibit phosphorylation of SMAD after BMP4 stimulation in EPC2-hTERT cells, a normal squamous esophageal cell line with no basal levels of SMAD1/5/8 phosphorylation. All tested VHHs were able to inhibit SMAD1/5/8 phosphorylation (FIG. 9A). VHHs A1, C4, C8 and E7 were able to completely inhibit BMP4-mediated SMAD activation, whereas VHH C3 was less effective. Because human and mouse BMP4 are highly homologous molecules (97% of homology in their mature regions), we tested whether VHH would also inhibit mouse BMP4 signaling. EPC2-hTERT cells were stimulated with mouse BMP4 and pSMAD activation detected by Western Blotting. The same pattern of signaling inhibition of the different VHHs was confirmed (FIG. 9B), indicating that our VHHs can prevent human but also mouse BMP4-mediated activation.

Cell Culture

The human hTERT-immortalized esophageal cell line, EPC2-hTERT, was a kind gift of Prof. A. Rustgi, University of Pennsylvania, Philadelphia, Pa., USA (Harada et al., 2003). EPC2-hTERT cells were cultured with KSFM media supplemented with 100 units/ml of penicillin, 100 μg/ml of streptomycin, 50 μg/ml of Bovine Pituitary Extract (Life Technologies) and 1 ng/ml of human recombinant Epidermal Growth Factor (Life Technologies). C2C12 mouse myoblasts (stably transfected with a reporter plasmid for BMP activity) were a kind gift of Dr. L. Zilberberg and Dr. D. Rifkin (Zilberberg et al., 2007) (New York University, School of Medicine, New York, N.Y., USA). C2C12 cells were cultured in complete Dulbecco's Modified Eagle Medium (DMEM) supplemented with 10% Fetal Bovine Serum (FBS), 2 mM glutamine, 100 units/ml of penicillin, 100 μg/ml of streptomycin and 700 μg/ml of G418 (InvivoGen SAS, Toulouse, France).

Western Blot

To detect phosphorylation of SMAD1/5/8 in vitro, EPC2-hTERTs were cultured in 24-well plates and activated with 100 ng/ml of BMP2, BMP4, BMP5, BMP6 or BMP7 (R&D Systems) for 4 hours with or without VHH at the indicated concentrations. After activation, each well was washed twice with ice-cold PBS and lysed with 100 μl M-PER lysis buffer (Sigma-Aldrich, MO, United States) containing Halt Protease and Phosphatase Inhibitor Cocktail (Thermo Scientific, Landsmeer, The Netherlands). Cell debris were pelleted and supernatant was collected. 15 μg of protein was then separated by 10% SDS-PAGE and transferred onto a PVDF membrane (Millipore, Amsterdam, The Netherlands). The blots were then blocked with 5% milk in Tris-buffered saline supplemented with 0.1% Tween-20 (TBST) for 1 hour at room temperature and washed in TBST before overnight incubation at 4° C. with antiphospho-SMAD1/5/8 (Cell Signalling), anti-βactin (Santa Cruz) or anti-GAPDH (Millipore) in 5% Bovine Serum Albumin (BSA). Blots were then washed with TBST and incubated for 1 hour at room temperature in 1:2000 horseradish peroxidase—conjugated secondary antibody in TBST. After a final wash with TBST, blots were incubated for 5 minutes in LumiGlow (BIOKE, Leiden, The Netherlands) and then chemiluminescence was detected using a Fuji LAS4000 illuminator (Fujifilm Medical Systems, Stamford, Conn.). Protein was quantitated with Image).

To detect BMPs in organoid or tissues lysates, the following antibodies were used: αBMP7 MAB3541 (R&D Systems) and αBMP6 AF507 (R&D Systems) at 1:1000; and αBMP5 ab10858 (Abcam, Cambridge, UK), αBMP2 500-P195 (Prepotech, London, UK) and αBMP4 MAB757 (R&D Systems) at 1:500 in 5% BSA. Organoids grown for five days without the presence of Noggin, were washed with ice-cold PBS and lysed as described above for the EPC2-hTERT cell lines. Mouse intestinal tissues were lysed at a ratio 1:20 with T-PER buffer (Sigma-Aldrich), homogenized for 2 minutes and then incubated on ice for 30 minutes. Cell debris were pelleted and supernatant was collected. Gel electrophoresis and western blots procedures were followed as described above.

Specificity Anti-BMP4 VHH

Figure 10:
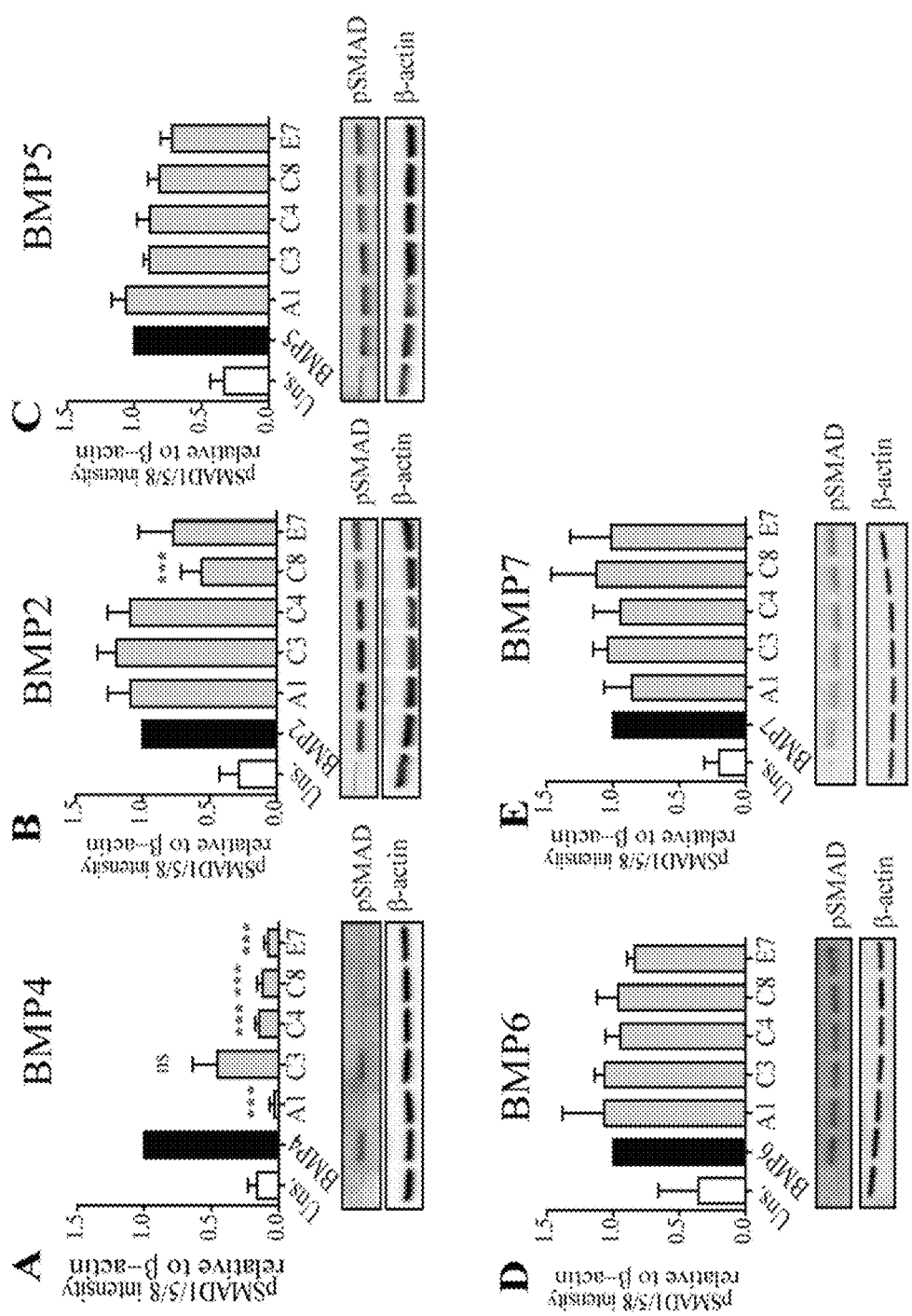
FIG. 10 shows the anti-BMP4 VHHs specificity to the different BMPs. EPC2-hERT cells were activated with 100 ng/ml of human BMP4 (A), 2 (B), 5 (C), 6(D) or 7(E) for 4 hours. VHH antibodies at a concentration of 5 μg/ml were added at the same time as the BMPs. Phosphorylation of SMAD1/5/8 was detected by western blot after cell lysis. Equivalent protein loading was confirmed by detection of beta-actin. Protein quantification was measured with Image). Error bars represent standard deviations of the mean, calculated from 3 independent experiments. ***=<0.0001

Due to the high similarities (~60-80%) between the mature regions of BMP4 and other members of the BMP family, we extended our analysis and tested the specificity of the VHHs in regards to BMP2, BMP5, BMP6 and BMP7 signaling (FIG. 10A-E). We found that whereas A1, C3, and C4 were BMP4 specific, C8 was also able to inhibit BMP2-mediated signals (FIG. 10A-10B). Interestingly, E7 seemed to also have an inhibiting effect on BMP2 and BMP5 signaling, yet these differences were not statically significant (FIG. 10A-B). None of the VHHs were able to inhibit BMP6 or BMP7 signaling (FIG. 10D-10E).

VHHs Also Inhibit BMP-Mediated Transcription

Figure 11:
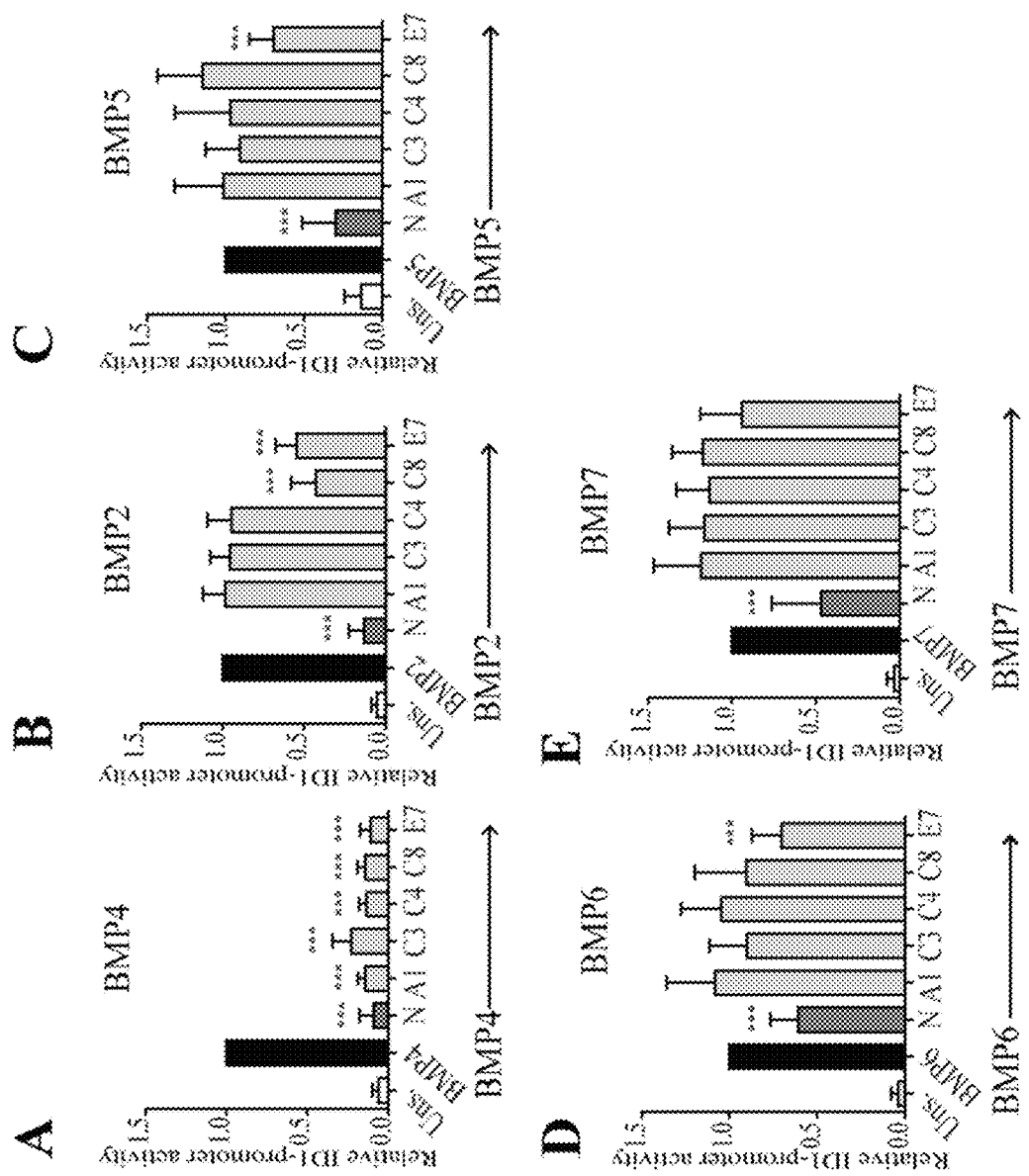
FIG. 11 shows that VHH inhibit BMP reporter activation. C2C12 were activated with human BMP4 (5 ng/ml) (A), BMP2 (50 ng/ml) (B), BMP5 (200 ng/ml) (5), BMP6 (50 ng/ml) (D) and BMP7 (200 ng/ml) (E) for 16 hours. VHH antibodies (light grey bars) and human Fc-Noggin at a concentration of 5 μg/ml (dark grey bar) were added at the same time as the BMPs, Luciferase activity was assayed with the Bright-Glo™ Luciferase Assay System. Luciferase values were normalized to background activity (no cells) and represented as a ratio to the activity of BMP-stimulated cells (black bars). Error bars represent standard deviations of the mean, calculated from three independent experiments, with experimental triplicates each. ***=<0.0001

Next, we set out to determine whether our VHHs would also inhibit BMP-mediated transcriptional activity. One of the most studied BMP target genes is the Inhibitor of Differentiation 1 (ID1). This is an immediate early gene that is activated by binding of the phosphorylated SMADs to its promoter region (López-Rovira et al., 2002). Thus, we employed the BMP-responsive C2C12 cells, which are stably transfected with the BRE-luciferase vector containing the BMP-Responsive-Element (the mouse ID1 promoter) cloned into the pGL3 luciferase vector (Zilberberg 2007). BMPR1a is highly expressed in C2C12, whereas BMPR1b is only detected at very low levels, and thus unlikely to play a role in BMP function in this set up (Zilberberg 2007). C2C12 cells were treated with the different BMPs with or without our VHHs or human Noggin at a concentration of 5 µg/ml. Luciferase activity was measured after 16 hours incubation. Most of the transcriptional data is in concordance with the results obtained with the phosphorylation of SMAD1/5/8. All VHHs were able to inhibit BMP4-mediated transcriptional activity to the same level as the natural inhibitor Noggin (FIG. 11A). As observed in the previous experiment only C8 and E7 were able to exert an inhibitory effect in BMP2-transcriptional activation (FIG. 11B). Surprisingly, E7 also was able to inhibit BMP5 and BMP6, albeit to a lesser extent than with the other BMPs (FIG. 11C-D). No VHH was able to inhibit BMP7-mediated transcriptional activation (FIG. 11E).

In sum, these sets of experiments confirm that VHH-mediated inhibition of phosphorylation of SMAD results in an inhibition of transcription of the BMP target gene ID1. They validate the generation of BMP4- (A1, C3 and C4), BMP2/4- (C8) and BMP2/4/5/6 (E7) specific VHHs. Remarkably, E7 mediated inhibition of BMP5/6 signaling is only observable in the luciferase experiment. This might indicate that small inhibition of SMAD phosphorylation might be enough to produce a difference in its transcriptional activity.

Dimerization Leads to Increased Functional Activity

Because the linking of VHH monomers can result in hetero- or homodimeric VHHs with increased antigen neutralizing activities (Mukherjee et al. 2012), we constructed three bivalent VHHs with two consecutive peptide spacers (GGGGS) as a linker. C4 was linked to C4 to generate a BMP4-specific homo-dimer (C4C4). C8 was linked to C8 to generate a BMP2/4 specific homo-dimer and E7 was linked to C8 to generate a BMP2/4/5/6 specific hetero-dimer. We sought to determine whether they would be more effective at inhibiting BMP signaling after dimerization, by comparing them to the monomers. To that end, we tested their ability to inhibit BMP2/4 mediated phosphorylation of SMAD1/5/8 in EPC2-hTERT cells. As shown in FIG. 12A, dimerization of C4 results in a more effective inhibition of BMP4 signaling, as C4C4 is effective at a much lower concentration (0.1 µg/ml) than the monomer C4. As expected and like the C4 monomer, the C4C4 dimer was unable to block BMP2 signaling (FIG. 12B). Interestingly, whereas C8 dimerization had no enhancement of the effectiveness to inhibit BMP4 signaling (FIG. 12C), it resulted in a more effective inhibition of BMP2, as C8C8 was able to inhibit BMP2-derived pSMAD at a lower concentration than C8 (FIG. 12D). The most effective concentration for C8C8 was 0.5 µg/ml, at which it was able to inhibit both BMP2 and BMP4 signaling. Albeit similar to the C8 monomer, C8E7 proved to be better at inhibiting both BMP2 and BMP4 as compared to the E7 monomer (FIGS. 12E and 12F), indicating that C8 (and not E7) might be the dominant molecule in this hetero-dimer.

Thus, whereas C4C4 is the strongest inhibitor of BMP4, C8C8 is the strongest at inhibiting BMP2-mediated SMAD activation. These results confirm that the dimerization of C4 and C8 has resulted in the generation of more effective VHHs for the inhibition of BMP4 or BMP2/4 signaling, respectively.

Figure 13:
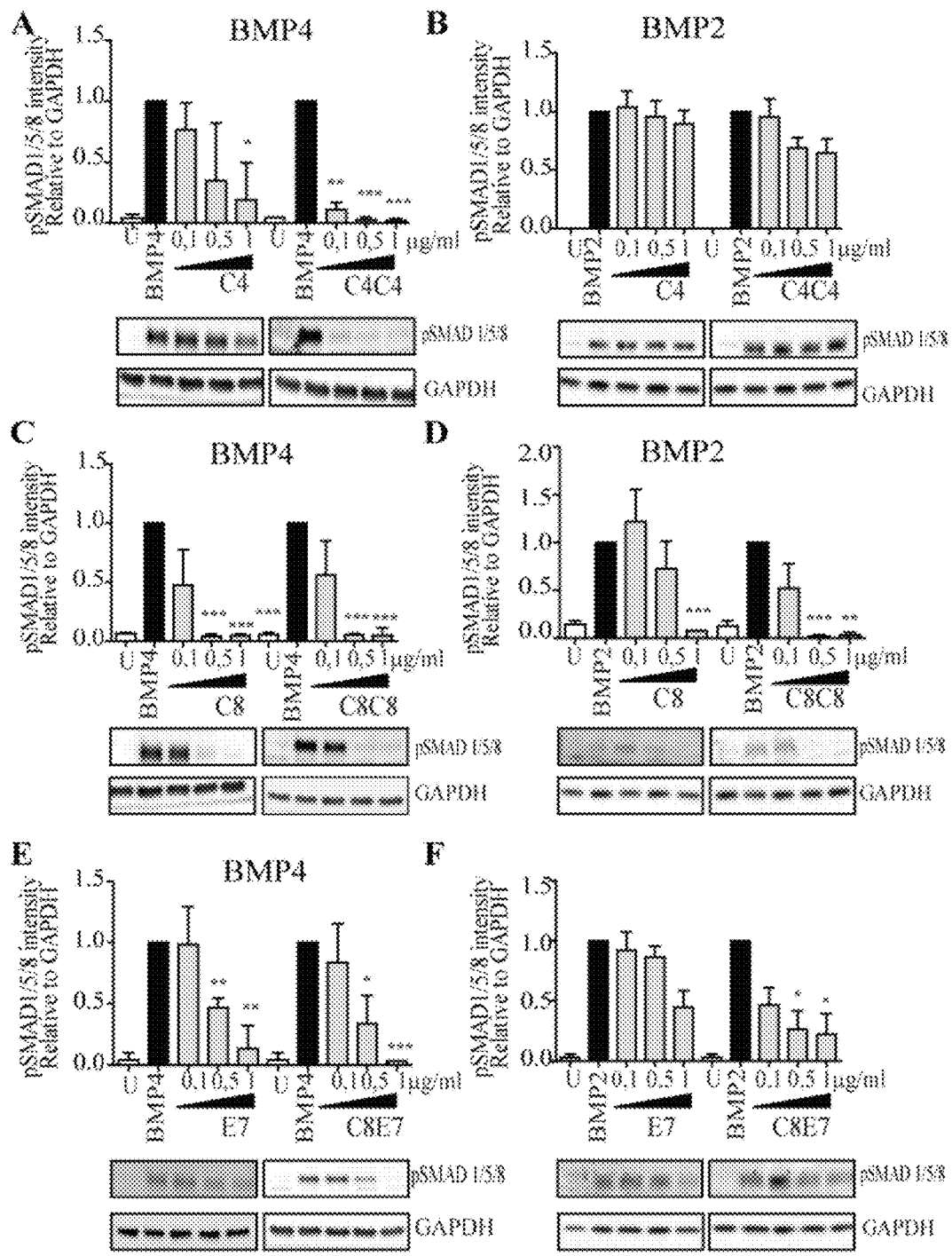
FIG. 13 shows that biheads inhibit BMP reporter activation. C2C12 were activated with human BMP2 (50 ng/ml), BMP4 (5 ng/ml), BMP5 (200 ng/ml), BMP6 (50 ng/ml) and BMP7 (200 ng/ml) for 16 hours. Noggin (N, dark grey bar) at 5 μg/ml was used as control. C4C4 (A), C8C8 (B) or C8E7 (C) were added at the same time as the BMPs at the indicated concentrations. Luciferase activity was assayed with the Bright-Glo™ Luciferase Assay System. Luciferase values were normalized to background activity and represented as ratio to the activity of BMP-stimulated cells (black bars). Error bars represent standard deviations of the mean, calculated from at least three independent experiments, with experimental triplicates each. *=<0.0001, =<0.01

To address whether the inhibition of the pSMAD signaling by the dimers also results in transcriptional inhibition of BMP target genes, we tested their ability to inhibit luciferase activity in the C2C12 cells (FIG. 13). Therefore, these cells were stimulated with different BMPs. Dimers at increasing concentrations were added at the same time and luciferase activity was measured 16 hours after. As expected, FIG. 13A shows that even at higher concentrations (5 µg/ml) C4C4 is not able to inhibit BMP2-mediated transcriptional activity, demonstrating its BMP4-specificity. At 0.1 µg/ml, C4C4 can block BMP4-mediated transcriptional activation to the same extent to that of Noggin. As seen in FIGS. 13B and 13C, C8C8 and C8E7 not only inhibit BMP4- but also BMP2-mediated transcriptional activation, confirming the pSMAD results. C8C8 is more efficient at inhibiting BMP2-mediated transcription than C8E7. Surprisingly, in contrast to its monomer, C8C8 was shown to weakly inhibit BMP5-mediated transcriptional activity. This might be explained by a loss of specificity after dimerization. Because E7 was shown to inhibit BMP5-mediated activation of pSMAD and ID1 activity, the ability for C8E7 to inhibit BMP5 transcriptional inhibition was not surprising (FIG. 13C). In contrast to E7, C8E7 is unable to impair BMP6-mediated transcriptional activation. The notion that C8 might be the dominant molecule in this heterodimer, might explain this contrasting result.

BMP Activity Luciferase Reporter Assay

C2C12 cells were plated in 96-well plates at $5 \times 10^3$ cells/well and cells were allowed to attach overnight. 100 µl of DMEM with 0.1% BSA were added in each well. VHH antibodies and human Fc-Noggin at the indicated concentrations were added at the same time. Wells with unstimulated cells were added as controls. Cells were treated in triplicate with the BMPs at the indicated concentrations for 16 hours. Luciferase activity was measured by adding 100 µl of luciferase substrate solution from the Bright-Glo™ Luciferase Assay System (Promega Benelux, Leiden, The Netherlands). After 3 minutes of incubation, luciferase activity was measured with Synergy HT Multi-Mode Microplate Reader (Biotek, Winooski, Vt., United States). Luciferase values were normalized to background activity (activity of wells with no cells) and represented as ratio to the activity of BMP-stimulated cells.

Example 6: Ex Vivo Activity

VHHs Inhibit Endogenous BMP Activity Ex Vivo in Organoid Cultures

Figure 14:
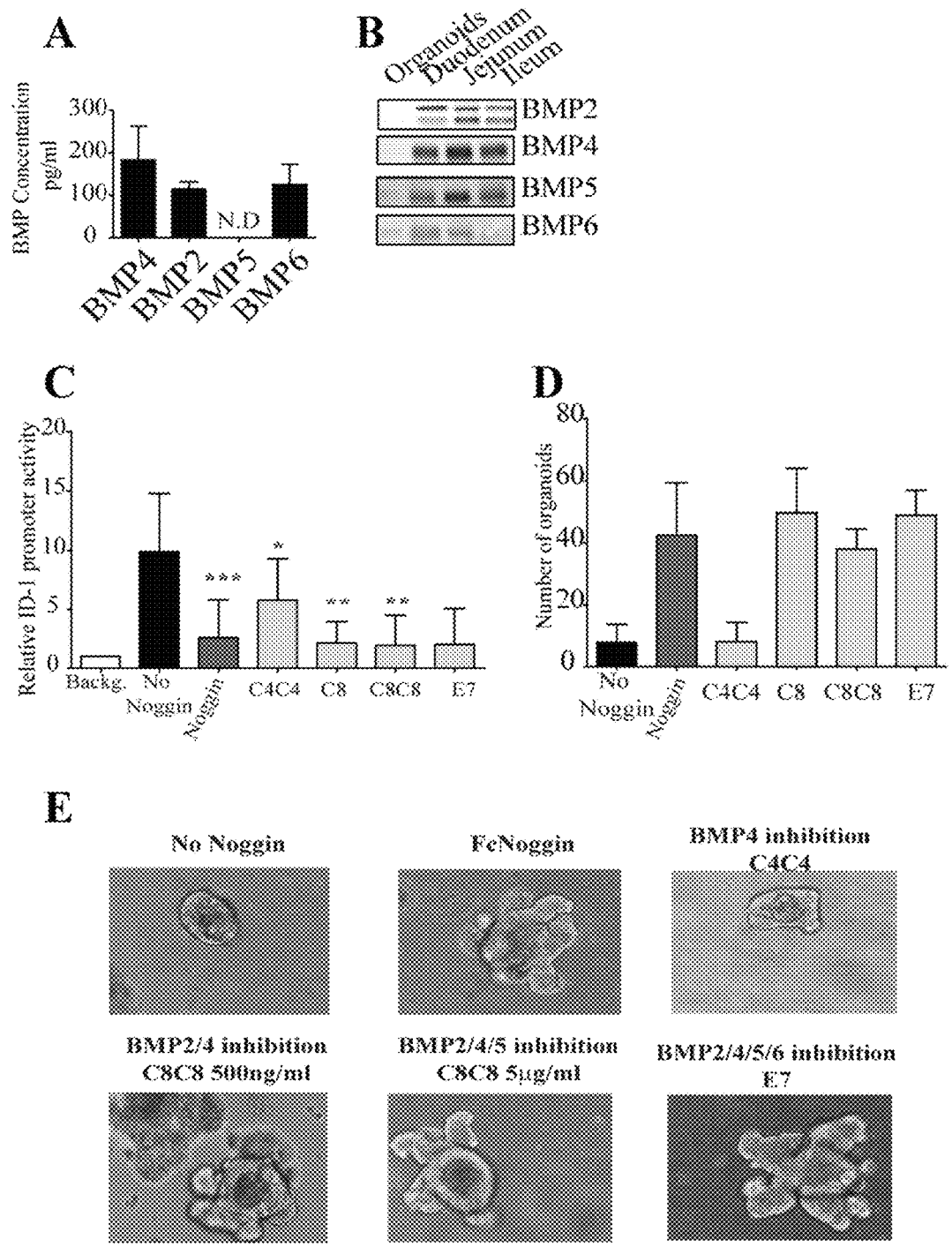
FIG. 14 shows the ability to inhibit endogenous BMP4 function in ex vivo intestinal organoid cultures. A) ELISA determinations of BMP4, 2, 5, and BMP6 secretion in mouse intestinal organoids cultured in the absence of Noggin for three days. BMP5 levels were not detected (N.D). B) Western blot analysis of lysates of mouse intestinal organoids grown under No Noggin conditions. Lysates from mouse duodenum, jejunum and ileum, were used as positive controls. C) BMP activity of organoid supernatants. C2C12 were cultured with conditioned media of organoids cultured under different conditions: BMP4 inhibition by C4C4 at 100 ng/ml; BMP2,4 inhibition by C8C8 at 500 ng/ml; BMP2,4,5 inhibition by C8C8 at 5 μg/ml; BMP2,4,5,6 inhibition by E7 at 5 μg/ml. Supernatants were collected at day 3. Luciferase activity was measured after 16 hours incubation, and the values were normalized to background activity (no cells) and represented as a ratio to the activity of unstimulated C2C12 cells: cells cultured with fresh Advanced DMEM/F12 media (Uns.). Error bars represent standard deviations of the mean as compared to No noggin (black bar). Data collected from at least five experiments with experimental triplicates each. *=<0.0001, =<0.01, *=<0.1. D) Number of organoids formed in cultures of mouse intestinal organoids grown for 5 days at the different conditions. Data collected from at least 5 experiments with experimental triplicates each. \*\*\*=<0.0001, \*\*=<0.01, \*=<0.1. E) Representative bright field images of mouse intestinal organoids grown under the indicated conditions for 5 days.

Finally, the VHHs were tested in an intestinal organoid culture system for their ability to neutralize the function of BMP4 ex vivo. Inhibition of BMP activity is one of the requirements to maintain Intestinal Stem Cells in vitro cultured as "organoids" that mimic crypt-villus structures and is usually provided by the addition of Noggin to the media. Murine small intestine organoids were cultured in the presence or absence of the VHH biheads and compared to Noggin. To precisely determine which BMPs are present in these cultures, BMP secretion was measured in the conditioned media of intestinal organoids grown without Noggin for three days. Whereas BMP2, BMP4 and BMP6 could be detected by ELISA (FIG. 14A), BMP5 levels were negative, most likely due to the low sensitivity of the ELISA assay (>250 pg/mL), and not due to the lack of BMP5 in these cultures. Indeed, analysis of the protein lysates of these organoids, detected the presence of BMP2, BMP4, BMP5 and BMP6 (FIG. 14B). Next, freshly isolated crypts from murine small intestines were cultured with the VHHs and tested for their ability to provide endogenous BMP inhibition and to sustain organoid cultures ex vivo. Analysis of BRE-luciferase activity in the supernatants of these cultures confirmed the functionality of these VHHs (FIG. 14C). Whereas specific BMP4 inhibition provided by C4C4 resulted in a partial decrease in the BRE-luciferase activity, concomitant inhibition of BMP2 and BMP4 was sufficient to result in a total blockage of BRE-luciferase activity. Further inhibition of BMP5 and BMP6 in these cultures, did not result in an increase in BRE-luciferase activity, revealing a minor role for these two BMPs in these cultures. Numbers of organoids were counted, and in concordance with the previous results, only C8C8 and C8E7 were able to maintain culture growth of organoids (FIG. 14D). Organoids maintained by Noggin, C8C8 and C8E7 shared the same characteristics (FIG. 14E). Three conclusions can be drawn from these experiments. One is that our VHHs C8C8 and C8E7 are able to inhibit BMP function ex vivo, to the same level as the natural inhibitor Noggin. The outcome indicates that C4C4 does not impair BMP2 signaling ex vivo, as the system requires inhibition of both BMP2 and BMP4 for the organoids to grow. Finally, specific inhibition of BMP4 lacks the deleterious side effects of unchecked stem cell proliferation.

Organoid Cultures

Organoids were cultured as previously described (Sato et al., 2009). Briefly, small intestines from wt mice were isolated and flushed with ice cold PBS to remove the feces. After they were opened longitudinally, the villi was scraped off gently with the use of a glass cover slip. The intestine was then cut in 0.5 cm pieces and washed with ice cold PBS for about 10-20 times until the supernatant was clean. The fragments were incubated with 2 mM EDTA in PBS for 30 min on ice whilst rolling. The tissue fragments were washed twice with ice cold PBS and the supernatant collected in PBS after 6 rounds of vigorous suspensions. The supernatant was passed through a 70 µm cell strainer (BD Bioscience) to remove residual villi and isolated crypts were centrifuged at 600 rpm for 5 min to remove single cells. Crypts were counted and resuspended in matrigel. 500 crypts were resuspended in 50 µl of polymerized Matrigel per well, in a 24-well plate. 500 µl Advanced DMEM/F12 (Invitrogen) medium containing 50 ng/ml EGF (Tebu-BIO, Heerhugowaard, The Netherlands), Fc-Noggin (10%) and fc-Rspondin (20%), both a kind gift of Prof. J. P Medema (AMC, Amsterdam) was added per well. Where indicated, VHHs were used in place of Fc-Noggin (C4C4 at 100 ng/ml, C8C8 at 500 ng/ml, C8C8 at 5 µg/ml, E7 at 5 µg/ml). As controls, some crypts were cultured in the absence of Noggin or VHHs. At day 3 supernatant was collected and medium was replaced. Lysates for protein extraction were collected at day 5.

ELISA

Concentrations of BMP present in the conditioned mouse organoid media were evaluated via ELISA, according to the manufacturers' protocol: BMP2 (RAB0028), BMP-4 (RAB0029), BMP-5 (RAB0031) and BMP-6 (RAB0032), from Sigma-Aldrich. Briefly, 1041 of conditioned media was added in duplicates to anti-BMP coated plates and incubated for 2.5 hours at room temperature. After 4-times washing with wash solution, 1000 of prepared biotinylated antibody were added to the plates and followed by one hour incubation period at room temperature. After another washing step, 100 µl of prepared streptavidin solution were added to each well and incubated for 45 minutes at room temperature with gentle shaking. After the incubation step, the wells were washed again 4 times and 100 µl of 3,3',5,5'-Tetramethylbenzidine (TMB) reagent were to each well. Plates were then incubated for 30 minutes at room temperature in the dark with gentle shaking. Finally, 50 µl of Stop Solution were added to each well and absorbance was read at 450 nm immediately.

Example 7: Affinity Measurements

Affinity Analysis of VHHs

To confirm their BMP specificities and to elucidate their binding affinities, our VHHs were subjected to surface plasmon resonance (SPR) analysis. In a first set of experiments, controls and VHHs (either as monomers or dimers) were coupled to SPR chips and the measurement of BMP affinities was obtained by injecting the different BMPs to the plate.

Figure 15:
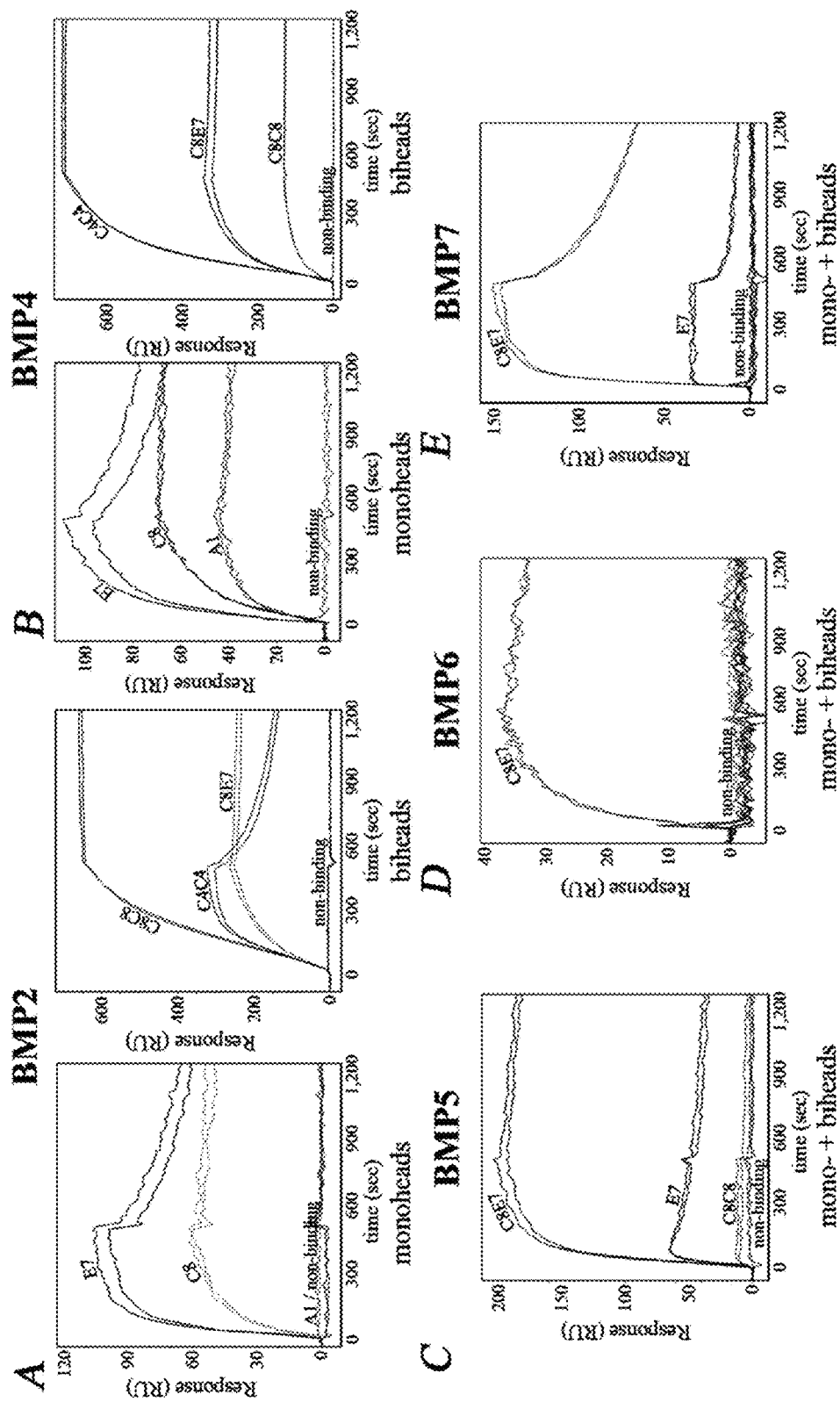
FIG. 15 shows the kinetic constants for BMP binding. Binding of VHHs to the different BMPs is tested in a direct SPR assay, where BMP2 (A), BMP4 (B), BMP5 (C), BMP6 (D) and BMP7 (D) are injected at different concentrations over a VHH-coated IBIS chip plate.

Noggin and BMPR1a were used as controls and bound all BMPs, concurring with published observations (Table 1) (Keller et al., 2004; Kirsch et al., 2000a). Amongst all the measured monomers, C8 and E7 had the highest binding affinity to BMP4, and were the only ones binding to BMP2 (FIGS. 15A and 15B, left graphs). For these two VHHs, the affinity for BMP4 was slightly higher than the one for BMP2 (Table 1). As expected, dimerization of C8 resulted in the generation of a homodimer (C8C8) with increased affinity for BMP2 and BMP4 as compared to its monomer (C8) (Table 1). Similarly, dimerization of E7 with C8 also produced a more effective VHH in binding to both BMP2 and BMP4. The lower KDs observed for these dimers result mainly from lower dissociation rates (Kd) as compared to the monomers (Table 1). This effect could be attributable to the presence of two binding sites per VHH-dimer and therefore a higher chance for re-binding BMP after initial dissociation. Interestingly, the association rate (Ka) for C8E7 to both BMP2 and BMP4 is similar to the one observed for C8, confirming the assumption that C8 is the prevalent molecule in this dimer. This data corresponds to the results from the functional experiments in which C8E7 behaves like CB rather than E7. Amongst the dimers, C4C4 and C8C8 were the ones with the highest affinities for BMP4 binding. The affinity of all the dimers for BMP2 and/or BMP4 binding was higher than those found for Noggin or the conventional commercially available anti-BMP4 antibody (RandD systems) (Table 1). In keeping with the functional experiments, E7, C8C8 and C8E7 bound to BMP5 (FIG. 15C). However, the affinity for these interactions is quite low as a result of a low association and a high dissociation constant (Table 2). These observations might explain why functional inhibition of BMP5 by these VHHs is not so significant.

Notably, and in contrast to the functional results, unspecific binding of dimers to diverse BMPs were observed. C4C4 was shown to bind BMP2; and C8C8 as well as C8E7 to BMP7 (FIG. 15A, 15C-E). These equilibrium dissociation constants befall within the ranges of 2-700 nM, a thousand times higher than the ones observed for BMP4 binding (~10-500 pM). Thus, the lack of functional implications for these interactions could be mainly attributable to the remarkably low binding affinities.

Thus, we have generated several VH Hs that can be classified into four groups (Table 3): BMP4, BMP2/4, BMP2/4/5 and BMP2/4/5/6-specific.

Surface Plasmon Resonance (SPR)

Serial dilutions (2.0-10 µg/ml) of purified VHHs were spotted on an amine-specific SensEye gold-film gel-type SPRchip (Ssens), using a Continuous Flow Microspotter (Wasatch Microfluidics, Salt Lake City, Utah, United States) as described (Lokate et al., 2007). BMP binding was analyzed on an IBIS MX96 (IBIS Technologies, Enschede, The Netherlands) instrument by performing injections with dilution series (0.05-2.0 µg/ml) of recombinant BMPs on the VHH-coated chip. In each injection, BMPs were injected and incubated for 8 min, followed by 15 min thorough washing with binding buffer (PBS+0.05% Tween20+0.05% sodium azide) to measure dissociation. Epitope binning was done by injecting VHH dilutions (2.0 µg/ml) over the chip, immediately after the dissociation step. Injections with blank binding buffer were used as reference. After each concatenated injection, the chip was regenerated with 10 mM glycine-HCl, pH 2.0. Experimental data were processed with SPRintX software (IBIS Technologies) and kinetic parameters were determined using Scrubber2 software (Bio-Logic Software, Campbell, ACT, Australia). Binding constants were obtained by global fitting to a one-site binding model.

TABLE 1

Kinetic constants for BMP2 and BMP4 binding

| Molecules | | BMP2 | | | BMP4 | | |
|---|---|---|---|---|---|---|---|
| Coupled to Chips | | $k_a$ | $k_d$ | $K_D$ | $k_a$ | $k_d$ | $K_D$ |
| VHHs | A1 | — | — | — | 51.4 (±6.0) | 29.8 (±9.6) | 574 (±184) |
| | C3 | — | — | — | 28.3 (±9.1) | 43.7 (±4.3) | 1,980 (±970) |
| | C4 | ND | ND | ND | ND | ND | ND |
| | C4-C4 | 37.0 (±11.5) | 70.6 (±3.6) | 2,150 (±760) | 19.2 (±2.4) | 0.2 (±0.03) | 9.7 (±1.6) |
| | C8 | 21.9 (±2.2) | 19.1 (±0.3) | 880 (±100) | 21.6 (±1.6) | 8.1 (±3.2) | 392 (±180) |
| | C8-C8 | 20.2 (±5.0) | 1.3 (±0.3) | 62.8 (±3.1) | 24.2 (±6.5) | 0.7 (±0.2) | 31 (±9) |
| | E7 | 44.6 (±3.2) | 47.2 (±3.1) | 1,070 (±130) | 60.1 (±5.1) | 30.8 (±5.1) | 512 (±73) |
| | C8-E7 | 19.4 (±3.1) | 10.7 (±1.0) | 554 (±38) | 34.6 (±6.6) | 3.4 (±0.8) | 99 (±12) |
| Controls | hNoggin | 17.1 (±2.5) | 16.2 (±0.9) | 961 (±91) | 47.2 (±11.9) | 3.9 (±0.8) | 91 (±38) |
| | BMPR1$_a$ | 28.2 (±2.0) | 14.0 (±2.0) | 498 (±33) | 16.3 (±4.5) | 9.2 (±2.8) | 635 (±268) |
| | αBMP4 (R&D) | — | — | — | 22.8 (±0.7) | 36.2 (±0.4) | 1,590 (±30) |

$k_a$ in $10^{-4}$ sec$^{-1}$M$^{-1}$, $k_d$ in $10^{-5}$ sec$^{-1}$, $K_D$ in pM
—: No binding detected
ND: Not Determined

TABLE 2

Kinetic constants for BMP5, BMP6 and BMP7 binding

| Molecules Coupled to chip | BMP5 $K_D$ | BMP6 $K_D$ | BMP7 $K_D$ |
|---|---|---|---|
| C8-C8 | 123,000 (±6,000) | — | — |
| E7 | 197,000 (±44,000) | — | 80,000 (±10,000) |
| C8-E7 | 95,000 (±7,000) | 50,000 (±20,000) | 31,000 (±2,000) |
| hNoggin | 68,000 (±5,000) | 50,000 (±10,000) | 80,000 (±10,000) |
| BMPR1$_a$ | 60,000 (±4,000) | 24,000 (±3,000) | 131,000 (±9,000) |

TABLE 3

BMP specificity of VHH antibodies

| Molecules | VHH | BMP4 | BMP2 | BMP5 | BMP6 | BMP7 |
|---|---|---|---|---|---|---|
| BMP4 | A1 | ●■ | ○ | ○ | ○ | ○ |
| | C3 | ●■ | ○ | ○ | ○ | ○ |
| | C4 | ●■ | ○ | ○ | ○ | ○ |
| | C4-C4 | ●■ | ●□ | ○ | ○ | ○ |

TABLE 3-continued

BMP specificity of VHH antibodies

| Molecules | VHH | BMP4 | BMP2 | BMP5 | BMP6 | BMP7 |
|---|---|---|---|---|---|---|
| BMP2/BMP4 | C8 | ●■ | ●■ | ○ | ○ | ○ |
| BMP2/4/5 | C8-C8 | ●■ | ●■ | ●■ | ○ | ●□ |
| | C8-E7 | ●■ | ●■ | ●■ | ●□ | ●□ |
| BMP2/4/5/6 | E7 | ●■ | ●■ | ●■ | ●■ | ●□ |

●■: Binding and inhibition of BMP function.
●□: Binding, but no inhibition.
○: No binding Example 8: Epitope Mapping In an effort to determine the binding epitopes and explain the different BMP specificities between these three VHHs (C4, C8 and E7), we employed an SPR sandwich cross-binding or "epitope binning" assay. In this assay, the VHHs (or control molecules) are spotted on an SPCR chip. In one concatenated cycle, the ligand (BMP4) is injected in the chip, followed by the injection of a second VHH (or control). This second molecule will only bind to the bound BMP4 if its epitope is still accessible. Thus, binding will not occur if both molecules compete for binding, whether allosterically or because they share the same epitope. The result of the BMP4 cross-binding assays are summarized in Table 4.

TABLE 4

Epitope Binning VHH Antibodies

| Injected Molecules | | Immobilized Molecules | | | | | |
|---|---|---|---|---|---|---|---|
| | | C8 | E7 | C4C4 | mNoggin | BMPR1a | aBMP4 |
| VHHs | C8 | ♦ | ● | ● | ○ | ○ | ● |
| | E7 | ● | ♦ | ● | ○ | ● | ● |
| | C4C4 | ● | ● | ♦ | ○ | ● | ● |
| Controls | mNoggin | ○ | ○ | ○ | ♦ | ○ | ● |
| | BMPR1a | ○ | ○ | ○ | ○ | ○ | ○ |
| | anti-BMP4 | ● | ● | ● | ● | ● | ♦ |

○: No binding, ●: binding, ♦: self-binding (binding to a free epitope in the BMP-dimer)
Injected BMPR1a did not bind to any immobilized BMP4

Figure 16:
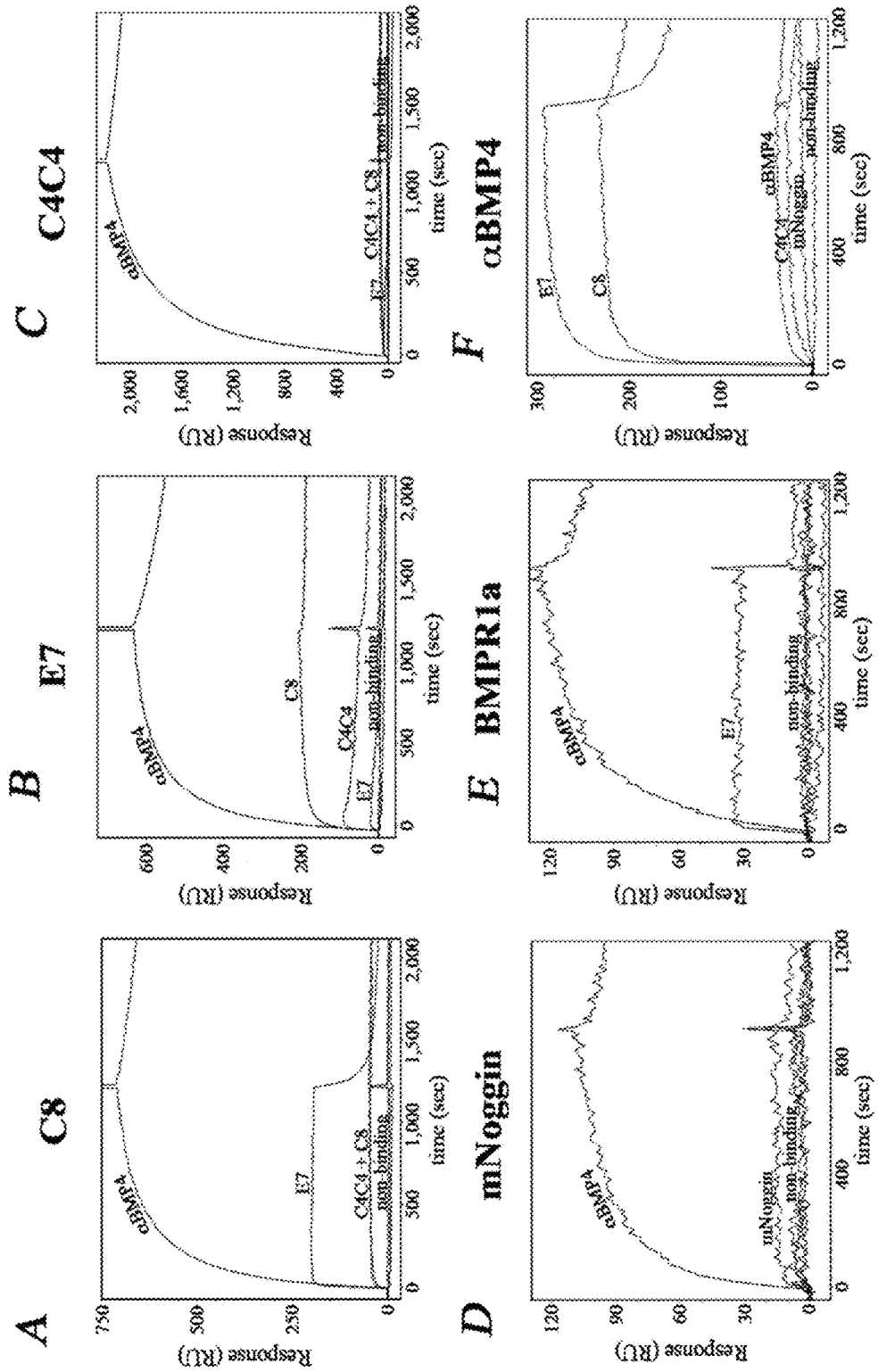
FIG. 16 shows the epitope binning of the different VHH Antibodies. Epitope mapping is done by coating chip plates with VHHs and the BMP4 is injected in the chip, followed by the injection of a second VHH or the corresponding controls. A) C8-; B) E7-; C) C4C4-; D) mouse Noggin-; E) BMPR1a-; F) R&D anti-BMP4-coated plates.

C8 and E7 do not share the same residues of the epitope, as they can cross-bind with each other in both directions: E7 can still bind to C8-bound BMP4 (FIG. 16A) and C8 can still bind to E7-bound BMP4 (FIG. 7B). E7 but not C8, can still bind to BMPR1a-bound BMP4 (FIG. 16C). This indicates that the C8 epitope resides in the BMPR1$_a$ binding site of BMP4, whereas E7 might interact with a region not targeted by BMPR1$_a$. Both C8 and E7, cannot bind to BMP4 bound to mouse Noggin, demonstrating that these VHHs compete with Noggin for BMP4 binding (FIG. 16D). Thus, it is most likely that the residues of the epitope of C8 overlaps with that of Noggin and that of the BMPR1$_a$, whereas the residues within the E7 epitope map to another region different to that of BMPR1$_a$, but targeted by Noggin. Because Noggin binds to both BMPR1$_a$ and BMPR2 epitopes, it is most likely that the residues within the E7 epitope map to the BMPR2 binding site.

As shown in Table 3, C8 and E7, but not Noggin or BMPR1$_a$, are able to weakly bind BMP4 bound to C4C4 (FIG. 16E). Conversely, C4C4 was able to bind C8- and E7-bound BMP4 (FIGS. 16A and 16B, respectively). This indicates that C4C4 binds to different residues of BMP4 than C8 and E7, but the residues of its epitope overlap with that of Noggin and BMPR1$_a$.

Cross-binding with the commercial anti-BMP4 was detected on all VHHs and controls, demonstrating that the epitope of anti-BMP4 is remarkably different than that of the VHHs and it resides in an area non-overlapping with Noggin or BMPR1$_a$ (FIG. 16F). Notably, most VHHs as well as Noggin, show weak self-binding in the cross-binding assay.

Example 9: Modelling VHHs with BMP4

To further understand the differential inhibitory mechanisms of C4, C8 and E7 we set out to model their interactions to BMP4 using the HADDOCK software (High Ambiguity Driven protein-protein DOCKing) (Dominguez et al., 2003). A threading model of BMP4 was generated with BMP2 (PBD X) as a template using Modeller9.9. Structures of the different VHHs were modeled based on resolved crystal structures of other VHHs, such as 4B5E (for C4) and SJX (for E7 and C8) based on their similarities at the sequence level (~74%). Interpretation of our functional and epitope binning data, provided the basis for the selection of residues to use for our Haddock modeling (Kirsch et al., 2000a, 2000b). Two areas are involved in the binding of BMP ligands to their receptors (FIG. 17A). The so-called 'wrist" is a large concave area involved in the binding to type I BMP receptors, whereas the knuckle is involved in type 2 Receptor binding. The epitope binning experiments indicated that C4 and C8 bind to a region overlapping both BMPR1a and Noggin, which would correspond to the wrist interface. These experiments also indicated that although targeting the same area, the exact epitope of these molecules differ as they weakly competed for BMP binding. This finding is not surprising due to the small nature of the VHHs and the large contact area of the wrist, allowing the simultaneous binding of these two single-domain antibodies to BMP4. Thus, it is reasonable to hypothesize that each VHH would bind to a different area within the wrist. Indeed, two contact points shape the wrist (Kirsch et al., 2000a).

One interface is formed by an hydrophobic groove filled by residues of monomer BMP2A (green residues in FIG. 17A). Residues located at the preβ, β1 and pre-helix loop (loop2) interact with receptor residues through salt bridges, hydrogen bonds and polar contacts (Kirsch et al., 2000a).

Figure 17:
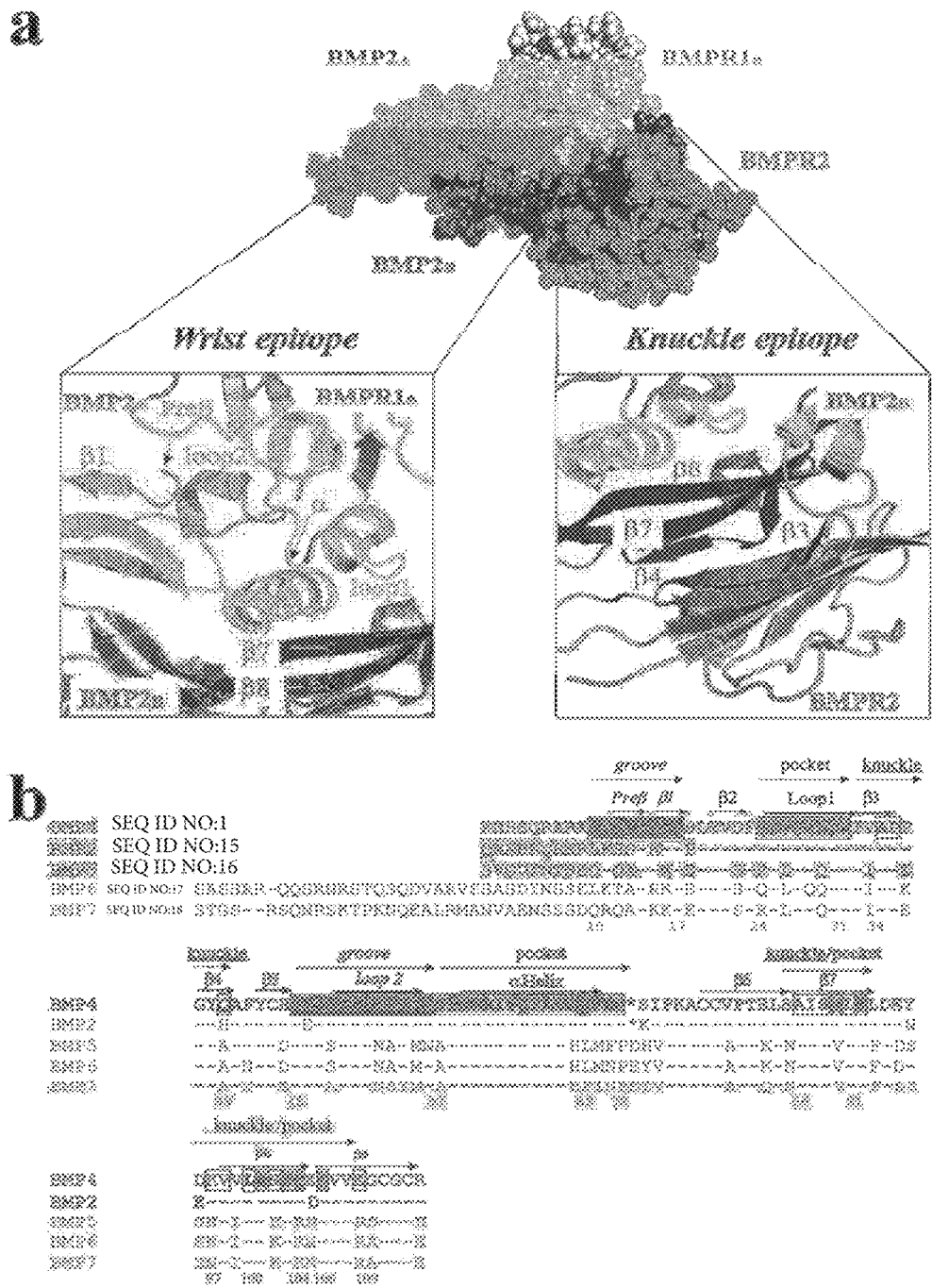
FIG. 17 shows BMP binding to BMPRs. A) Space filled view of BMP2 binding to BMPR1a and BMPR2 (PBD entry 2H62). BMP2 binds to BMPR1a through the wrist, whereas the knuckle is involved in BMPR2 binding. The insets show an enlarged cartoon diagram of each of the molecular binding interfaces. The wrist is composed by two contact points: an hydrophobic groove (formed by residues located at the preβ, β1 and loop2) and a hydrophobic pocket (composed by residues of the αhelix from BMP2A and residues from the loop1, β7 and β8 from BMP2B). The knuckle is formed by residues of monomer BMP2B located in the β strands: β3, β4, β7 and β8. B) Sequence alignment of different BMPs. NCBI accession numbers: BMP2, NP_001191.1; BMP4, AAH20546; BMP5, NP_066551.1; BMP6, NP_001709.1, BMP7, NP_001710.1. Location of secondary structures such as p strands, loops and a helix are adapted from (Kirsch, Nickel, and Sebald 2000). Dashes represent identical amino acids and stars represent gaps in the sequence. The residues located in the hydrophobic groove or the hydrophobic pocket of the wrist are shaded in dark or light grey, respectively. Residues located in the knuckle are squared (Kirsch, Sebald, and Dreyer 2000, Allendorph, Vale and Chloe 2006). Residues in bold are the residues shown to be involved in BMP4 binding to our VHHs by HADDOCK MODELLING.
Figure 18:
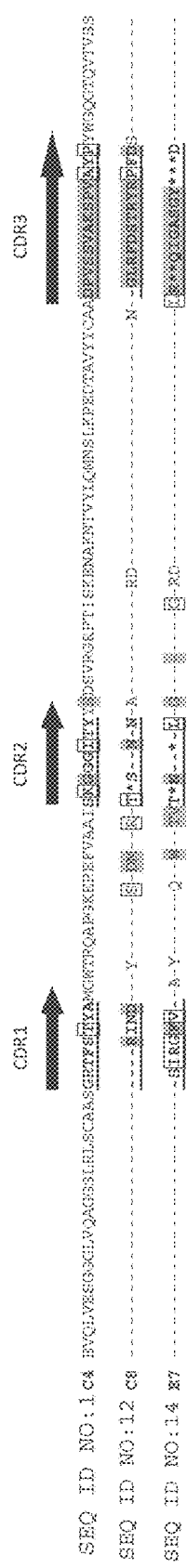
FIG. 18 shows the alignments of the VHH sequences. The hypervariable domains (CDRs) are in bold and underlined. The shaded residues are the ones that deviate from the V and J-gene germline sequences of Vs, or are in the part of CDR3 that is derived from the D-gene. Boxed are the residues that differ from the germline and require two mutations in the germline DNA sequence, indicative of higher order maturation. Stars represent identical amino acids and d represent gaps in the sequence.

Because C4 can bind and inhibit only BMP4-mediated activation, C4 must target a BMPR1a molecular interface in which differences in residues between BMP2 and BMP4 are observed. Examination of the sequences of BMP2 and BMP4 reveals some differences in the residues that form this hydrophobic groove (FIG. 17B). In particular, K15 of BMP2 (R15 in BMP4), located at the β1, has been found to form a salt bridge with Asparagine 46 of BMPR1a. Therefore the residues involved in the hydrophobic groove of the wrist (FIG. 17) were used for docking C4 to BMP4. Analysis of the amino acid sequence of C4 in comparison with a wide array of VHH sequences, revealed a number of non-conserved residues in the CDR3 region (FIG. 18). Therefore the following residues were selected for docking: T31, K53, I57, A110 and P112. In addition D99 was also used, as it has been reported that Asparagine 46 of BMPR1a is important for BMP-BMPR1a binding.

The docking results were grouped into 10 clusters. Cluster 1 contained 78 structures and presented a HADDOCK score of −86.7+/−8.7. In this model, loop2 of BMP4 packs hydrophilically against residues from both CD R2 and CDR3 (FIG. 19A). P50 of BMP sustains hydrophilic hydrophobic interactions with 157; and D46 forms an hydrogen bond with S102 of C4 (FIG. 19B). In contrast, the pre β1 and β1 region mainly interact with CDR3 residues. Of note is D99, that forms salt bridges with both K12 and R15, a similar interaction was observed between K15 of BMP2 and D46 of BMPR1a (Kirsch et al 2000).

Figure 20:
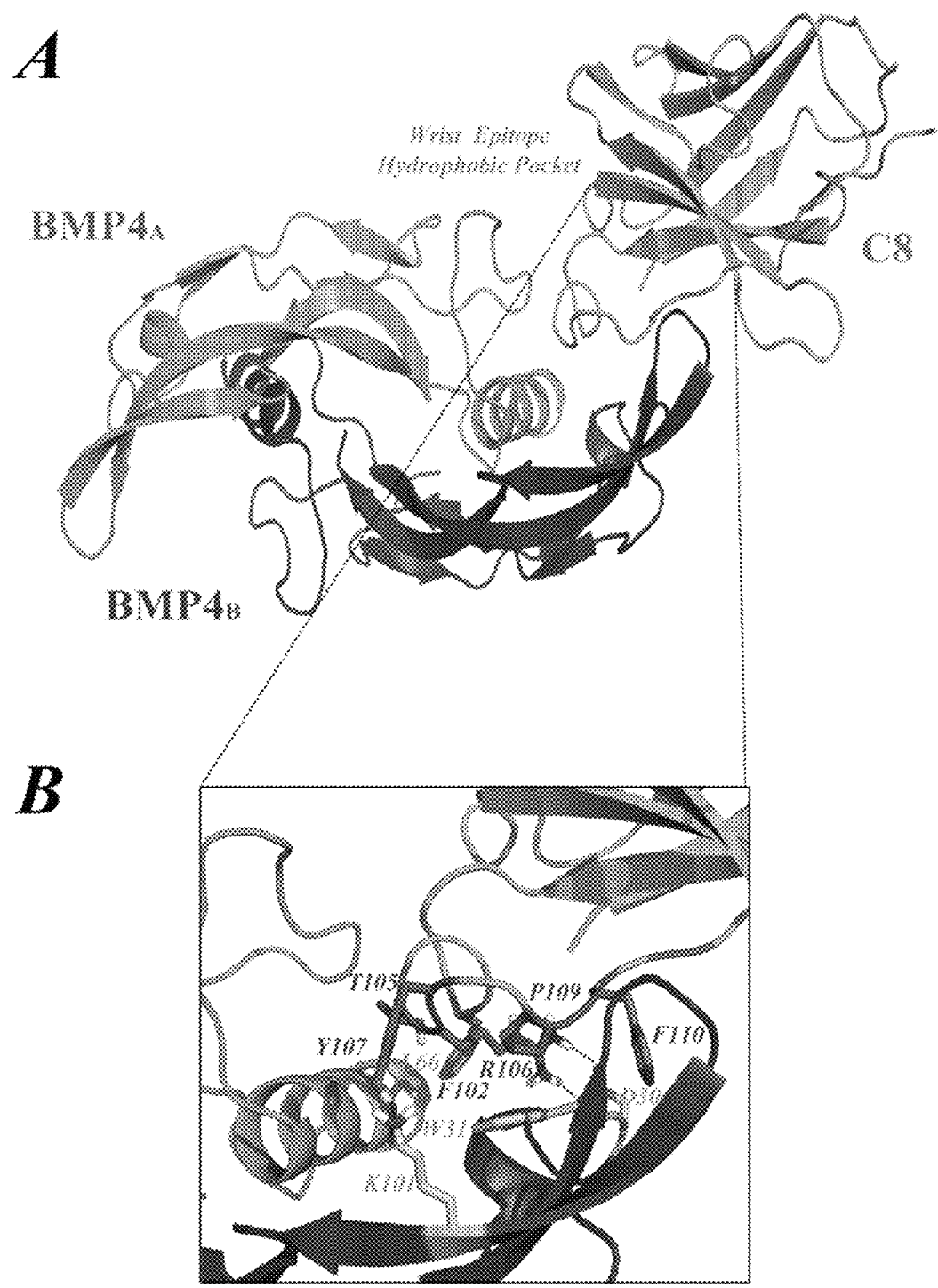
FIG. 20 shows a cartoon diagram of BMP4-C8 binding. A) The BMP4 dimer is shown in green and red. C8 is shown in cyan. B) Enlarged view of the molecular interface between BMP4 and C8. Dotted lines represent hydrogen bonds and/or salt bridges. BMP4 (yellow) and C8 (magenta) residues participating in interactions are displayed as sticks.

A hydrophobic pocket constitutes the other contact point of the wrist (FIG. 8A). Residues within the αhelix of BMP2A and residues in loop1, β7 and β8 of BMP2B fit like a "knob-into-pocket" with a Phe85 of a molecule of BMPR1a 31. Because C8 can only bind to BMP2/4 and no other BMPs, the epitope for C8 must be in a BMPR1a binding region displaying differences in the residues between BMP2/4 and BMP5/6/7 but weakly overlapping with C4. Thus, it is tempting to speculate that C8 might target the hydrophobic pocket, where a few invariant residues locate: V26, W30, N31, N68, S69, M89 (FIG. 17B). As for C8, the following invariant residues in the C8 sequence were selected for docking: P109, L100, F102, F110, Y107, R101, R106, R108 (FIG. 18). HADDOCK grouped 191 structures into 6 clusters. Cluster 1 presented a score of −142.6+/−2.9 that included 138 structures. In this model, C8-BMP4 binding appears to be driven by interactions between residues in the CDR3 region of C8 and the hydrophobic pocket of the wrist (FIG. 20A). In the hydrophobic surface of the BMP4 αhelix, L66 sticks out to interact with T105 of C8. Residues in loop1 of BMP4 provide a hydrophobic area allowing for interactions like P109 with W31 of BMP4 and the double salt bridge between D30 and R106 of C8 (FIG. 20B). Also F110 and F102 make multiple contacts with the area that D30 is enclosed. Y107 forms a hydrogen bond with K101 located at the inner side of the β8 strand.

Figure 21:
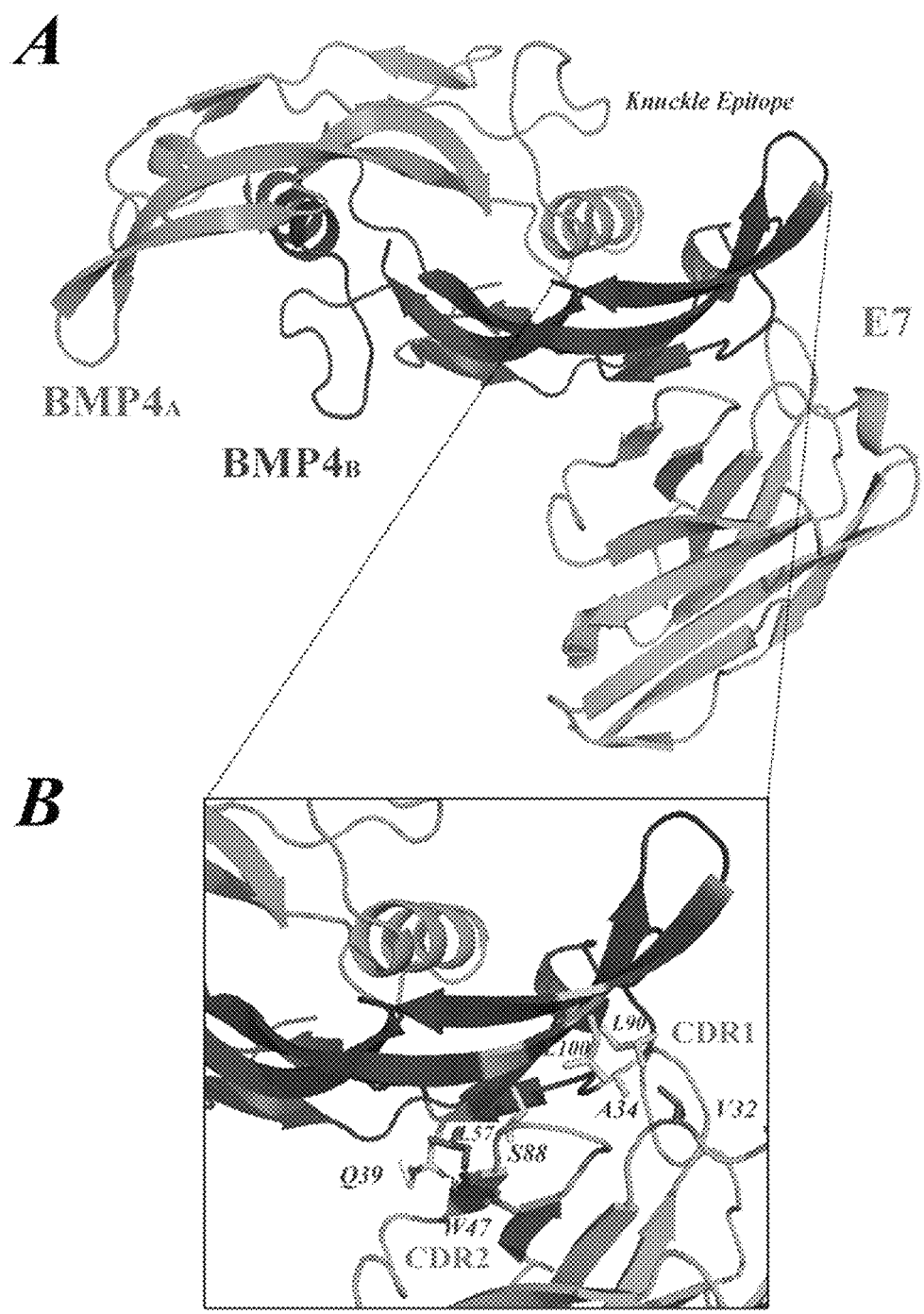
FIG. 21 shows a cartoon diagram of BMP4-E7 binding. A) The BMP4 dimer is shown in green and red. E7 is shown in cyan. B) Enlarged view of the molecular interface between BMP4 and E7. Dotted lines represent hydrogen bonds and/or salt bridges. BMP4 (yellow) and E7 (magenta) residues participating in interactions are displayed as sticks.

Our epitope binning experiments show that E7 does not overlap with binding of C8/C4 nor BMPR1a, thus indicating that its binding site it is not located in the wrist. Because E7 still competes with Noggin for BMP2 binding, and Noggin also binds to the knuckle, it is tempting to speculate that the knuckle might be the region targeted by E7. The 'knuckle" area, is formed by amino acids of BMP2B (FIG. 17A) in which four regions, with highly conserved residues, are involved in binding to BMPR2. Because we have shown that E7 binds to all tested BMPs, the knuckle residues located in this epitope were used for docking of E7 (Nickel et al. 2001). HADDOCK clustered 173 structures into 4 clusters. Cluster 1 with 150 structures gave the highest score: −83.5+/−5. In this model, both CD R1 and CDR2 residues of E7 are involved in this binding (FIG. 21A). W47 from E7 interacts with Q39 forming an hydrogen bond. The nitrogen atom from the main chain of T56 in E7 forms an hydrogen bond with S88. L57 from E7 is also in close proximity to S88 (FIG. 21B). V32 from the CDR1 is in close proximity to an hydrophobic area formed by the residues located in the outer sides of the β3 (A34) and β8 strands (L90).

Figure 22:
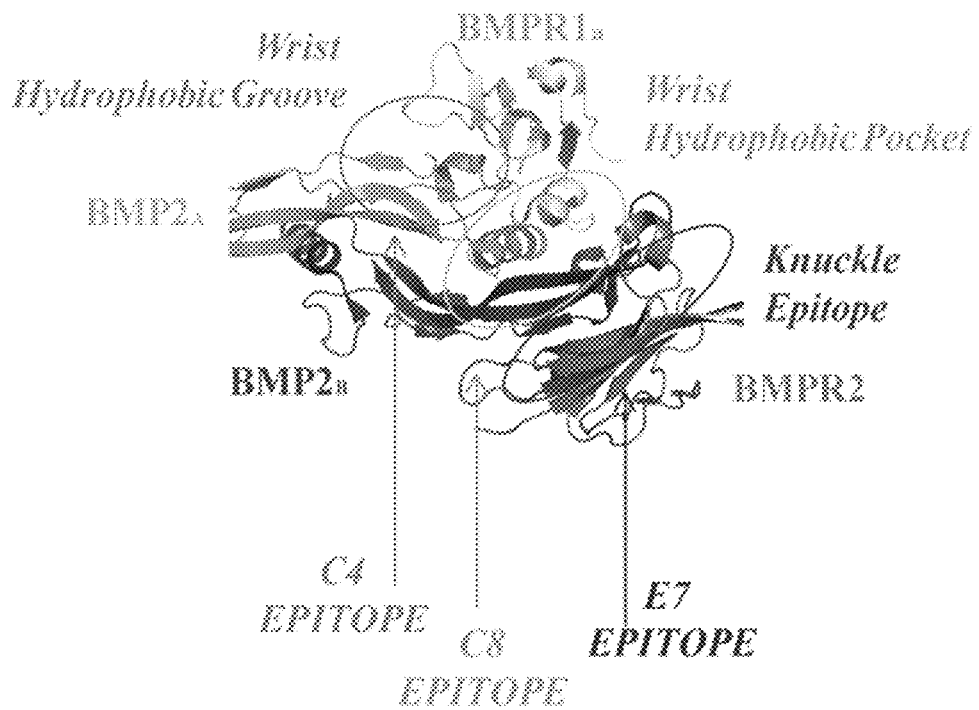
FIG. 22 shows modeling of VHH inhibition. Ribbon diagram of BMP2 binding to BMPR1a and BMPR2 (PBD entry 2H62) shows three contact points to receptor binding. Two of these contact points form the so called "wrist", involved in high affinity binding to BMPR1a. Due to differences between BMP2 and BMP4 residues, the epitope in BMP4 but not in BMP2 is recognized by C4. The hydrophobic pocket in the wrist is comprised by residues from both BMP2 monomers. The residues in this region are conserved between BMP2/BMP4 but differ to other BMPs and form the contact area for C8 binding. The third contact point constitutes the knuckle epitope, which is composed by residues from BMP2B. The notion that all the residues in this region are highly conserved between BMPs indicates this being the E7 epitope.

In sum, HADDOCK modeling has provided important structural evidence for the specificity of the tested VH Hs (FIG. 22). These results seem to indicate that selective targeting of the hydrophobic groove of BMP4 involved in BMPR1a provides BMP4-specificity, whereas selective targeting of the hydrophobic pocket of this molecular interface supports specificity for both BMP2 and BMP4. VHHs targeting the knuckle display restricted BMP specificity, being able to bind BMP2, BMP4, BMP5, BMP6 and BMP7.

HADDOCK Modelling

A 3D homology model of BMP4 was generated with BMP2 (PBD 1ES7) as a template using Modeller9.9. Structures of the different VHHs were modelled based on crystal structures of other VHHs, such as 4B5E (for C4) and SJX (for E7 and C8) based on their similarities at the sequence level (~74%). HADDOCK software (High Ambiguity Driven protein-protein DOCKing) (Dominguez et al., 2003) was used to model BMP4 binding to the different VHHs. Residues located in the complementary-determining regions (CDR1 and CDR2) that differ from the germline as a result of one or more mutations in the codon, as well as residues in CDR3, were chosen as the VHH active sites for the docking. Therefore, for C4, those residues were: T31, K53, I57, D99, A110, P112; for C8: S44, L100, R101, F102, R106 Y107, R108, F110; and for E7: R29, G30, V32, G55, T56, L57, G68 and L96.

Epitope binning experiments suggested that C4 interacts with the molecular interface involved in BMP4-BMPR1a binding. Because C4 can bind and inhibit BMP4- but not BMP2-mediated activation, C4 most likely targets a BMPR1a binding region in which differences in residues between BMP2 and BMP4 are observed. Examination of the sequences of BMP2 and BMP4 reveals that the hydrophobic groove of the wrist is the only BMPR-binding area where differences between BMP2 and BMP4 exist (K12, N13 and R15). Therefore this region was used for docking C4 to BMP4. Residues located in this region and used for the docking were: S12, S13 and K15 (different between BMP2 and BMP4) as well as F49, P50, L51, A52, D53, H54 and S69 (identical between BMP2 and BMP4) (FIG. 17B).

Because C8 can only bind to BMP2 and BMP4 and not the rest of the BMPs, the epitope for CB presumably resides in a BMPR1a binding region displaying differences between BMP2,4 and BMP5,6,7 but not overlapping with C4. A large number of non-conserved residues between these two subgroups of BMPs are found in this region (FIG. 17B). Since they might represent a determinant for C8 specificity, residues within the hydrophobic pocket and different between BMP2,4 and BMP5,6,7 were used for docking: V26, W30, N31, N68, S69, M89. HADDOCK grouped 191 structures into 6 clusters.

Our epitope mapping experiments show that E7 binds to the knuckle. Moreover, all the residues in this region are highly conserved between BMPs, a notion that corresponds to the unspecific nature of E7. The 'knuckle" area, is formed by residues of only BMP2B in which four regions are involved in binding to BMPR2 (Nickel et al., 2001). In this area, a small shallow pocket is formed by hydrophobic residues surrounded by a ring of polar and non-polar amino acids. The central hydrophobic residues have been shown to be binding determinants for this molecular interface and were therefore used to model E7 with BMP4: S88, L90, A34, H39 and L100 (FIG. 17B).

Example 10: Confirmation of Modelling with Mutational Variants

Figure 23:
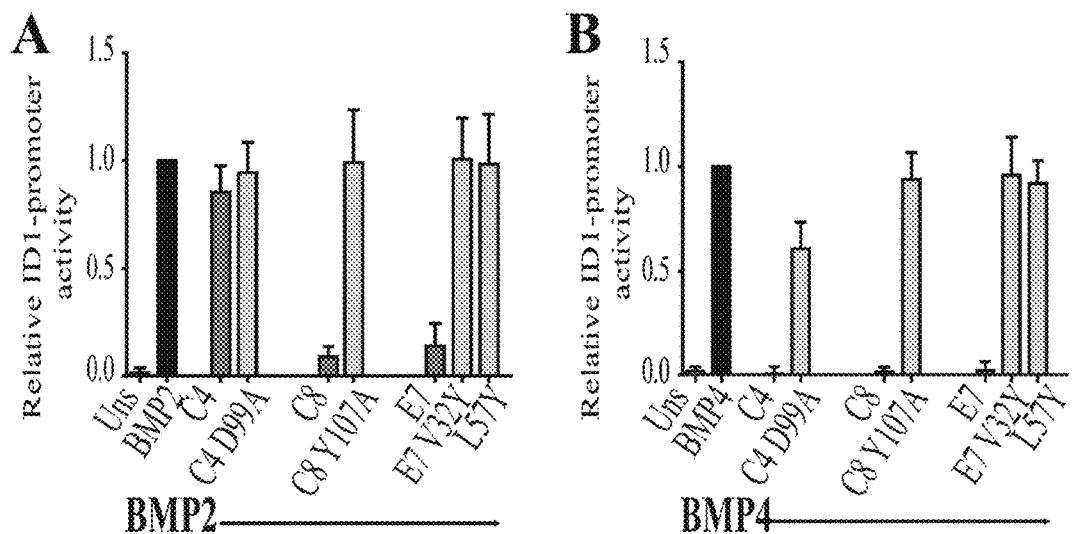
FIG. 23 shows the functional characterization of the generated mutant variants. C2C12 were stimulated with (A) BMP2 (50 ng/ml) or (B) BMP4 (5 ng/ml) for 16 hours. VHHs or the variants were added at the same time as BMPs at 5 µg/ml. Luciferase activity was assayed with the Bright-Glo™ Luciferase Assay System. Luciferase values were normalized to background activity and represented as ratio to the activity of BMP-stimulated cells (black bar). Uns=unstimulated C2C12 cells. Values calculated from three independent experiments, with experimental triplicates each.

To validate the HADDOCK models, we generated mutational variants of each VHH. Some of the residues shown to be involved in VHH-BMP4 binding were substituted singly by in vitro mutagenesis. Mutation of the residues found to be involved in E7-BMP4 interactions, resulted in variants unable to inhibit both BMP2 and BMP4-mediated transcriptional activation (FIG. 23). Similarly, variant Y107A of C8 exerted no effect on BMP2 or BMP4 function, suggesting its inability to bind these BMPs. Finally, D99A of C4 was found to affect C4's ability to inhibit BMP4 signaling. As expected, C4 nor its D99A mutant, had any effect on BMP2 function. Because these mutations affect the potency of the different VHHs, these data validate the HADDOCK models and confirm that the mutated residues are important binding determinants. Furthermore, analysis of the sequences of the different VHHs and of the binding determinants of the BMPR epitopes, seem to confirm the results from our docking modellings. The paratopes of the VHHs involved in the binding to BMP4 are non-conserved and might provide the basis for their specificity to those regions. For instance, I57, located at the CDR2 of C4 which sustains hydrophilic interactions with P50 of BMP4, presents a higher order maturation from the VHH germline. S102 and S107, located at CDR3 of C4, are also determinants for BMP4 binding and are not shared with C8 or E7. Similarly, the paratope of C8 is formed by residues mainly located in the CDR3, which only shares 28.5% similarities with C4 and E7. Likewise, the binding determinants of the modelled binding of E7 to BMP4 are not conserved in C4 and C8 (such as W47, V32, L57). Of note, is the low percentage of similarities in the CDR1 region of E7 with C4 (25%) and C8 (12.5%), suggesting an important functional role for this region.

Generation of VHH Variants by Site-Directed Mutagenesis

Site directed mutagenesis by overlap extension PCR (Ho et al., 1989) was used to substitute a single amino acid in the designated VHH. Two divergently oriented and partly complementary primers were designed with the substituted sequence. These primers were subsequently used together with the VHH outward primers to amplify two fragments with the VHH sequence. The generated two DNA fragments with an overlapping region were then used as template for a second PCR to glue the 2 fragments together and restore the complete VHH sequence. Final PCR fragment was digested with the restriction enzymes with unique recognition sites at the N and C terminus of the VHH and cloned in the expression plasmid pMEK222. Substitutions were confirmed by sequencing and VHH mutants were produced and purified as indicated before.

Example 11: Functional Comparison with Other Commercially Availables Anti-BMP4s

Figure 24:
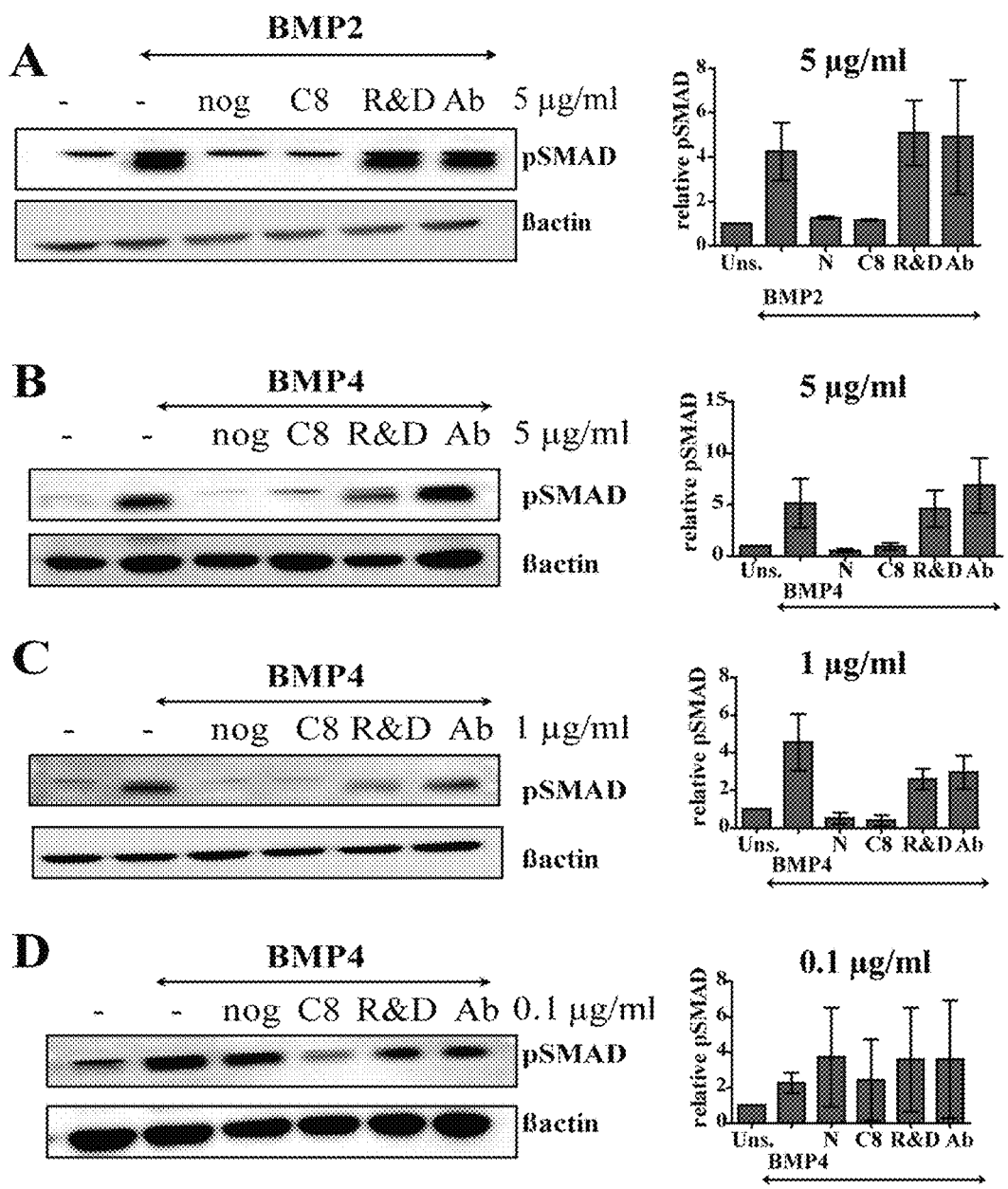
FIG. 24 shows a functional comparison of commercial anti-BMP4 antibodies. EPC2-hERT cells were activated with 100 ng/ml of human BMP2 (A or BMP4 (B-D) for 4 hours. Noggin, C8 or the commercial anti-BMP4 from R&D (clone 66119) or Abcam (ab39973) (Ab) were added at the same time at a concentration of 5 µg/ml (A,B), 1 µg/ml (C), or 0.1 µg/ml (D). Phosphorylation of SMAD1/5/8 was detected by western blot after cell lysis. Equivalent protein loading was confirmed by detection of β-actin. Protein quantification was measured with ImageJ and calculated as a ratio to BMP-stimulated cells. Error bars represent standard deviations of the mean, calculated from 3 independent experiments.

The functional activity to inhibit BMP signaling of our VHHs was compared to the one of two commercially available antibodies: anti-BMP4 R&D (Clone 66119, Mouse IgG2B, MAB757) and anti-BMP4 Abcam (Rabbit polyclonal, ab39973). These two antibodies are BMP4 specific as described in their data sheet and confirmed by us in FIG. 24A. When their inhibitory capacity was tested in EPC cells stimulated with BMP4, we observed that only when used at higher doses (FIG. 24B-C) they were able to inhibit signaling, albeit to a much lesser extent than our VHH C8 or the natural antagonist Noggin. When used at 0.1 µg/ml, (FIG. 24D), they were unable to inhibit signaling altogether. Moreover, the use of the antibody R&D was not sufficient to block BMP4 function in other studies, as it failed to inhibit BMP4-mediated increase in the expression of extracellular matrix proteins in mouse mesengial cells (Tominaga et al., 2011).

Figure 12:
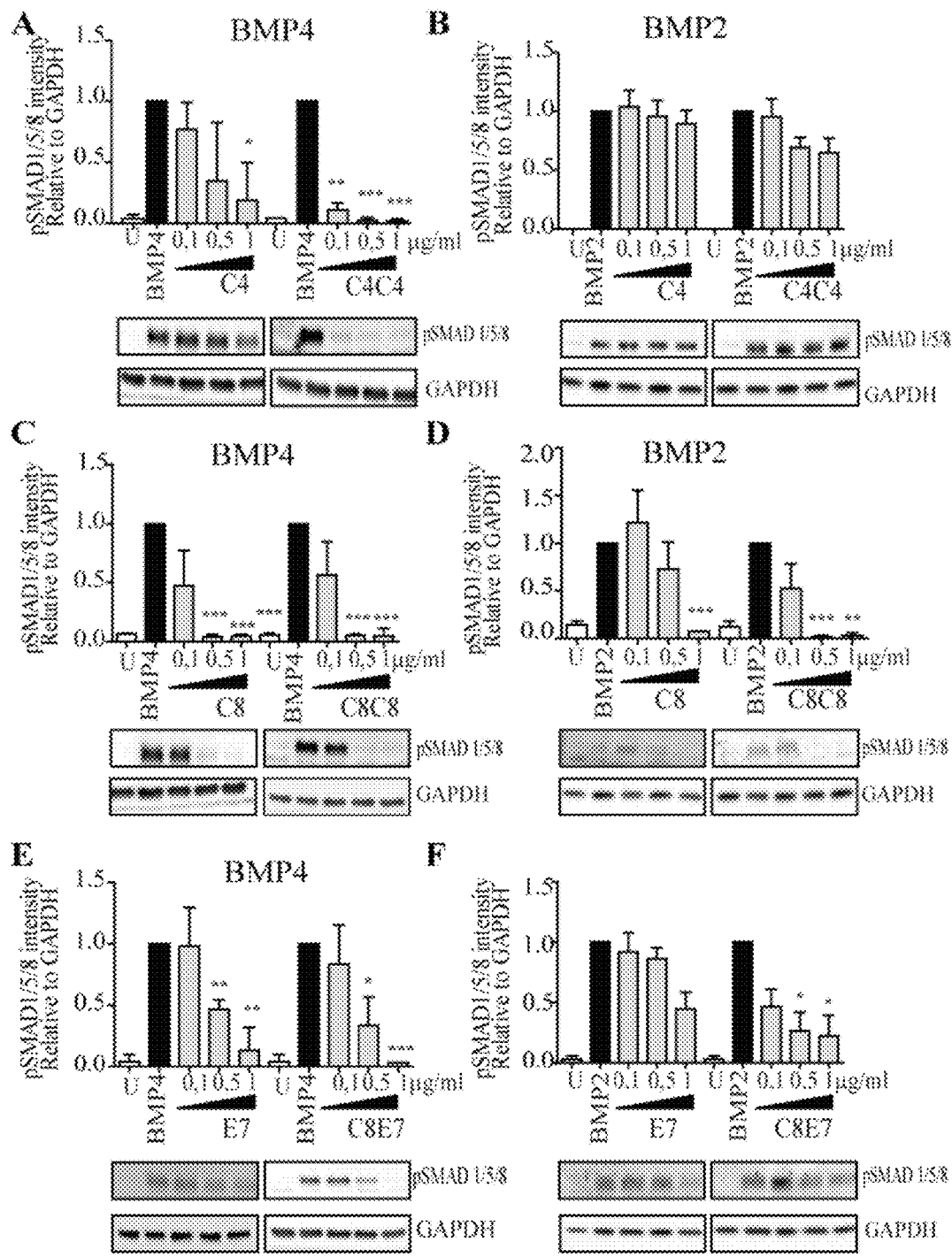
FIG. 12 shows that VHH biheads display differential specificity to BMPs. EPC2-hERT cells were activated with 100 ng/ml of human BMP4 (A,C,E) or BMP2 (B,D,F) for 4 hours. VHH monoheads and biheads at the indicated concentrations were added at the same time. Phosphorylation of SMAD1/5/8 was detected by western blot. Equivalent protein loading was confirmed by detection of GAPDH. Protein quantification was measured with ImageJ. Error bars represent standard deviations of the mean, calculated from 3 independent experiments. *=<0.0001, =<0.01, *=<0.1
Figure 25:
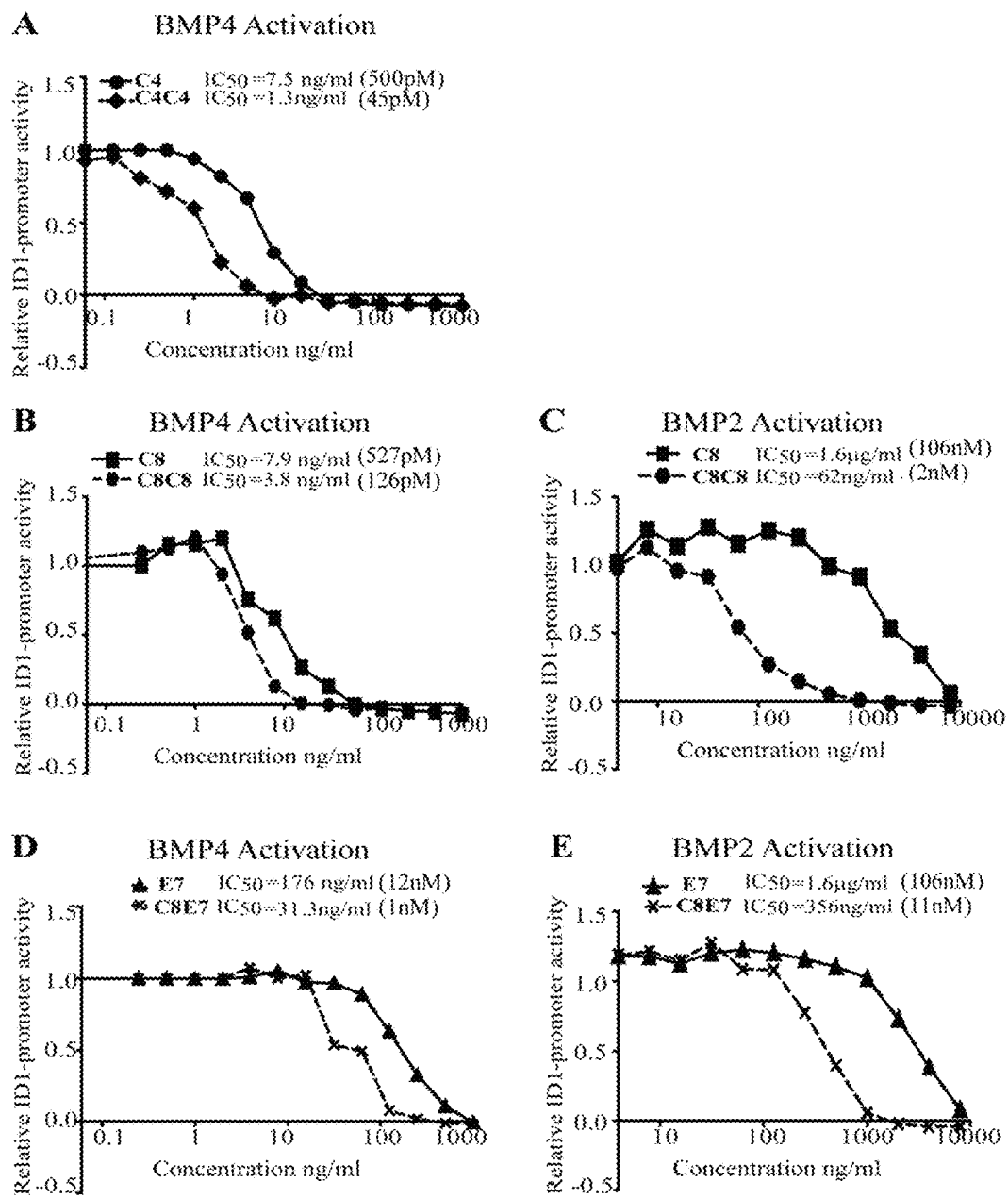
FIG. 25 shows the $IC_{50}$ curves of VHH biheads and monoheads. C2C12 were activated with human BMP4 at 5 ng/ml (A,B,D) or BMP2 at 50 ng/ml (C,E) for 16 hours. VHHs were added at the same time as the BMPs at the indicated concentrations. Luciferase activity was assayed with the Bright-Glo™ Luciferase Assay System. Luciferase values were normalized to background activity and represented as ratio to the activity of BMP-stimulated cells. Data is representative from two experiments and with experimental triplicates each. IC50 values were fitted using Graph-Prism Software (La Jolla, Calif.) in a nonlinear regression model.

Our data and previous results seem to indicate that their epitope is not located in the wrist or the knuckle of BMP4. For instance, the Abcam anti-BMP4 was generated using a peptide that corresponds to residues 50-150 from the immature pro-BMP4 region. Since mature BMP4 starts at residue 299, the epitope of Abcam anti-BMP4 does not therefore correspond to the region involved in signaling through the BMP receptors. The anti-BMP4 antibody from R&D was raised against a peptide corresponding to residues 293-408 of the immature pro-BMP4 protein, which encompasses a highly BMP4-specific N-terminal region upstream the preβ (residues 1-9 in FIG. 17B) as well as the BMPR binding molecular interfaces. However, our epitope binning data clearly demonstrated that this antibody does not compete with BMPR1a or Noggin, or any of the VHH tested (FIG. 16), demonstrating that anti-BMP4 from R&D does not target the BMPR binding epitopes. Thus, a likely region to comprise its epitope might be the highly BMP4-specific N-terminal part of the mature BMP4 protein that is not involved in binding with the receptors but rather to binding with heparin. Because functional experiments with these two antibodies demonstrate that the affinity (Table 1) and the inhibition of BMP-mediated pSMAD activation (FIG. 24) is much lower than the one provided by Noggin or our VHHs, it indicates that targeting BMPR binding areas such as the wrist and the knuckle provides superior affinity which translates into more potent functional BMP inhibition Example 12: Stronger Functional Inhibition with VHH Biheads Experiments in EPC2-hTERT cells demonstrated that the dimers presented increased inhibitory capacities (FIG. 12). To evaluate the extent of this increase in potency, the $IC_{50}$ of the different VHHs were determined in a dose-dependent inhibition assay in C2C12 cells (FIG. 25). C2C12 cells were plated in 96-well plates at $5 \times 10^3$ cells/well and cells were allowed to attach overnight 100 µl of DMEM with 0.1% BSA were added in each well. VHH antibodies were added at the indicated concentrations at the same time as 5 ng/ml BMP4 (FIG. 25A-B, D) or 50 ng/ml of BMP2 (FIG. 25C,D). Luciferase activity was measured after 16 hours. Values are represented as ratio to the activity of BMP-stimulated cells. C4C4 displayed a 9-fold increase at inhibiting BMP4-mediated transcriptional activation as compared to monomer C4 and the lowest $IC_{50}$ amongst all tested VHHs (1.3 ng/ml or 45 nM). Similarly, dimerization of C8 also resulted in a more potent dimer (FIG. 25B-C). However, its effects were more striking for BMP2 rather than BMP4 inhibition. Nevertheless, C8C8 was still 16 times more potent at inhibiting BMP4 than BMP2. Albeit better than E7, C8E7 proved to be similar at inhibiting both BMP2 and BMP4 as compared to C8 (FIG. 25D-E), suggesting that C8 might be the dominant molecule in this hetero-dimer. In sum, all the herein described VHHs displayed an IC50 for BMP4-mediated inhibition in the range of 1-200 ng/ml and for BMP2-mediated inhibition in the range of 0.6-1.6 µg/ml. The IC50 values for BMP4 inhibition observed in our VHHs are considerably lower than those observed for anti-BMP4 commercially available from R&D (Katagiri et al 1994) and those described in WO_2008/030611.

Figure 26:
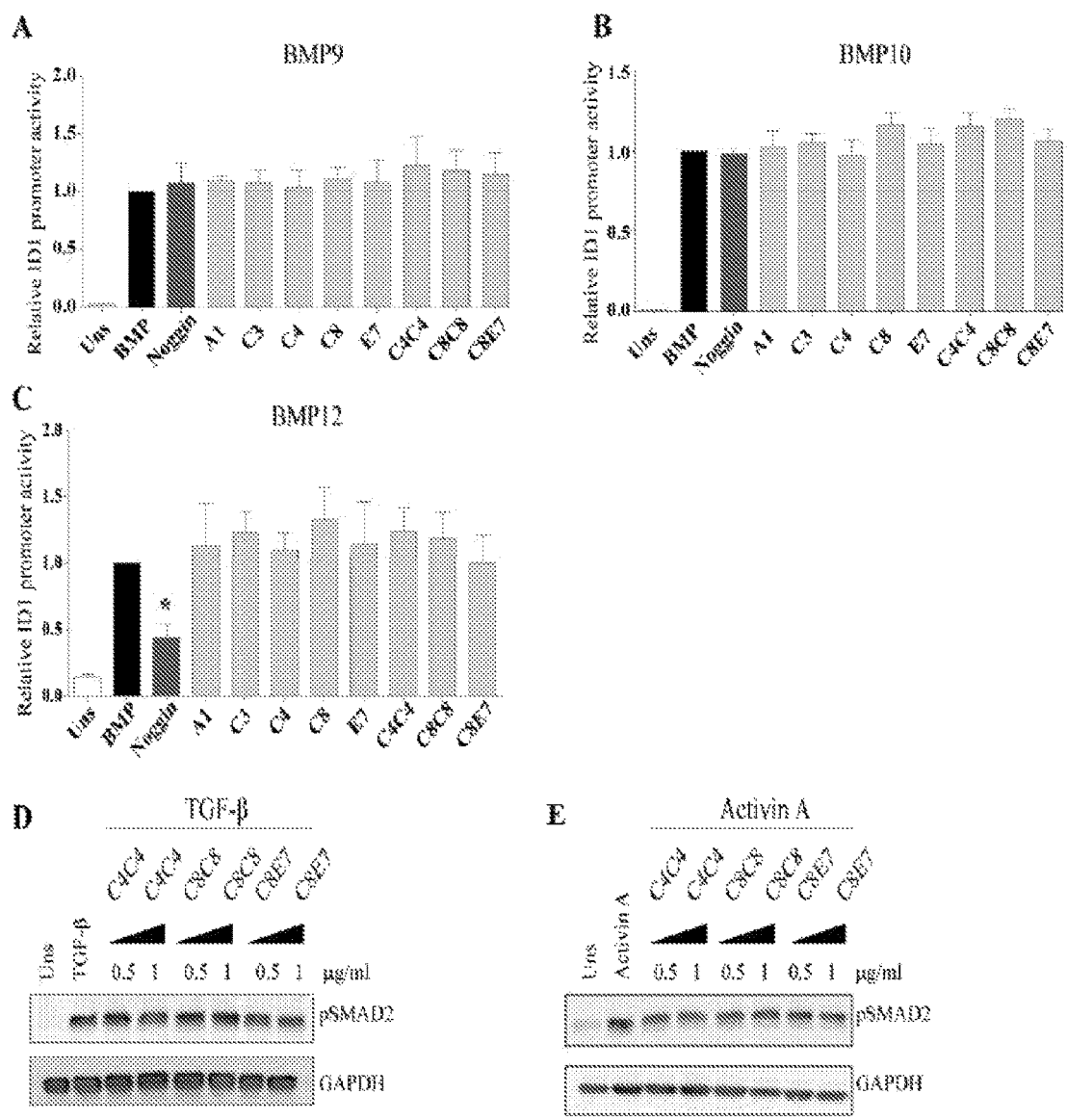
FIG. 26 shows that VHH do not inhibit other members of the BMP subfamily or the TGF-β superfamily. C2C12 were activated with human A) BMP9 (25 ng/ml), B) BMP10 (50 ng/ml) or C) BMP12 (50 ng/ml), for 16 hours. VHH or Noggin were added at the same time at a concentration of 5 µg/ml. Luciferase activity was assayed with Bright-Glo™ Luciferase Assay System (Promega). Luciferase values were normalized to background activity and represented as ratio to the activity of BMP-stimulated cells. Error bars represent standard deviations of the mean, calculated least three independent experiments, with experimental triplicates each. \*=<0.1. Statistical analysis was done using a two-tailed P-test. D) C2C12 were activated with 2 ng/ml of TGF-β (R&D Systems) for one hour. VHHs at the indicated concentrations were added at the same time. Western blots of phospho SMAD2 are representative of two experiments. E) HEK293 cells were activated with 100 ng/ml of Activin-A (R&D Systems) for one hour. VHHs at the indicated concentrations were added at the same time. Western blots of phospho SMAD2 are representative of two experiments.

The specificity of the biheads is retained, except for C8C8, which surprisingly, weakly inhibits BMP5-mediated transcriptional activity at higher doses (FIG. 13). The remaining members of the BMP subfamily have low sequence similarities to BMP4 (~30% identities). Nevertheless, they were tested to confirm the specificity of the monoheads and biheads. As expected, no inhibition of BMP9, BMP10 or BMP12 was observed by any of the VHHs tested (FIG. 26A-C). Other members of the TGF-β superfamily were also tested to further confirm the BMP-specificity of the VHHs. No inhibition of SMAD2 phosphorylation was observed after TGF-β or Activin A activation (FIG. 26D-F).

Specificity VHHs

C2C12 cells were plated in 96-well plates when they reached confluency, cells were treated in triplicate with 25 ng/ml of BMP9, 50 ng/ml of BMP10 or 50 ng/ml of BMP12 (all from R&D Systems), for 16 hours. VHHs or Noggin were added at a concentration of 5 ug/ml. C2C12 cells or HEK293 were plated on 12-well plates and starved for 5 hours, before stimulation with 2 ng/ml of TGF-β (R&D Systems) or 100 ng/ml Activin-A (R&D Systems), respectively. VHHs at the indicated concentrations were added at the same time. After 1 hour cells were lysed, and protein isolation and SDS-PAGE separation were performed as described previously. For protein detection the following antibodies were used: antiphospho-SMAD2 at 1:1000 (Cell Signaling).

Example 13: Confirmation of Modelling with Heterodimeric BMPs

To further confirm the nature of the epitopes of the VHHs, experiments with heterodimer BMP4 and BMP2 using the C2C12 cells system were conducted. Although C8 is able to inhibit the homodimer BMP2, it fails at inhibiting the heterodimer of BMP2 with either BMP6 or BMP7. This shows that the epitope of C8 binds to a region formed by both monomers of BMP2. Conversely, C4 inhibits BMP4-derived signals but only half of the BMP4/7 signals. Similarly, E7 inhibits BMP4 and BMP2 signals, but only half of the ones of BMP2 or BMP4 heterodimers. Therefore, these experiments confirm that whereas C4 and E7 target an epitope formed by one BMP monomer only, C8 binds to an epitope formed by two monomers as it is unable to inhibit heterodimers of BMP4 or BMP2 (FIG. 27).

Epitope Mapping with Heterodimer BMPs.

C2C12 were activated with 10 ng/ml of human BMP4 and BMP4/6 or 50 ng/ml of BMP2, BMP2/6 or BMP2/7. The VHHs or Noggin were added at the same time at a concentration of 5 ug/ml. Luciferase activity was assayed with Bright-Glo™ Luciferase Assay System (Promega). Luciferase values were normalized to background activity and represented as ratio to the activity of BMP-stimulated cells. Error bars represent standard deviations of the mean, calculated least three independent experiments.

Figure 28:
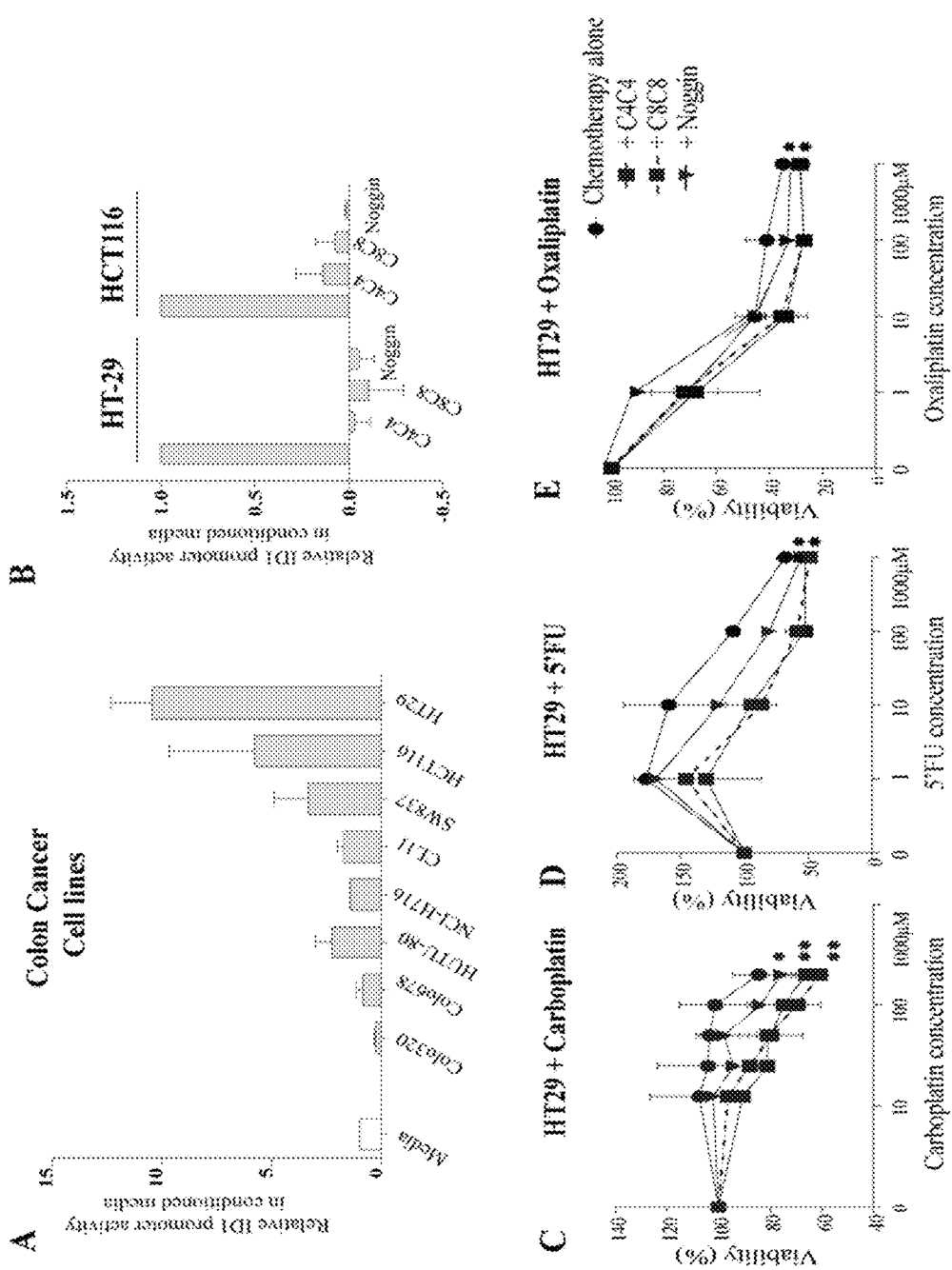
FIG. 28(A-F) shows that anti-BMP4 VHHs inhibit cancer derived BMP signals and function.

Example 14: Inhibition of BMP4 by the VHHs Increase the Chemosensitivity of BMP4+ Colorectal Cancer Cells BMP signaling has been shown to be implicated in chemoresistance in colorectal cancer cell lines. We wanted to determine whether this effect could be attributable to BMP4 that is being secreted by the cancer cells, and if therefore, could be inhibited by our BMP4-specific VHHs. A panel of colorectal cancer cells was tested for the presence of active BMPs in their conditioned media (FIG. 28A). To that end, the C2C12 cells were cultured with supernatants from different cancer cell lines. When normalized for the BMPs present in normal fetal calf serum, we found a high variability in BRE-luciferase activity across cell lines. Incubation of the conditioned media of the cancer cell lines with the different VHHs, showed that certain lines were secreting exclusively BMP4 and not BMP2 or other BMPs, as C4C4 was already sufficient to completely inhibit this signal (FIG. 28B). One of those cell lines, HT29, was used to test the effect of BMP4 inhibition in terms of proliferation. No effect was observed when cultured with the VHHs or Noggin alone (data not shown). However, both VHHs C4C4 and C8C8 proved to increase the chemosensitivity when combined with different types of chemotherapeutics. This is demonstrated by the fact that combining the VHHs with Carboplatin, 5'FU or Oxaliplatin had a significant stronger effect on cell viability as compared to chemotherapy alone (FIGS.

28,C,D and E). The effect on cell viability by Noggin was not as effective as observed for C4C4 or C8C8.

Chemosensitivity

HT29 cells were plated in 96-well plates at a density of 10,000 cells per well. After 24 hours they were stimulated at the indicated concentrations of 5'Fluorouracil (5'FU, Oxaliplatin and Cisplatin) for 48 hours. The VHHs or Noggin were added at the same time at a concentration of 500 ng/ml. Cell viability was measured by adding the Presto Blue Reagent (Invitrogen) for 2 hours at 37° C., after which absorbance was measured at 520 nm.

Example 15: VHHs Inhibit the Non-Canonical Pathway in Colorectal Cancer Cells

Figure 29:
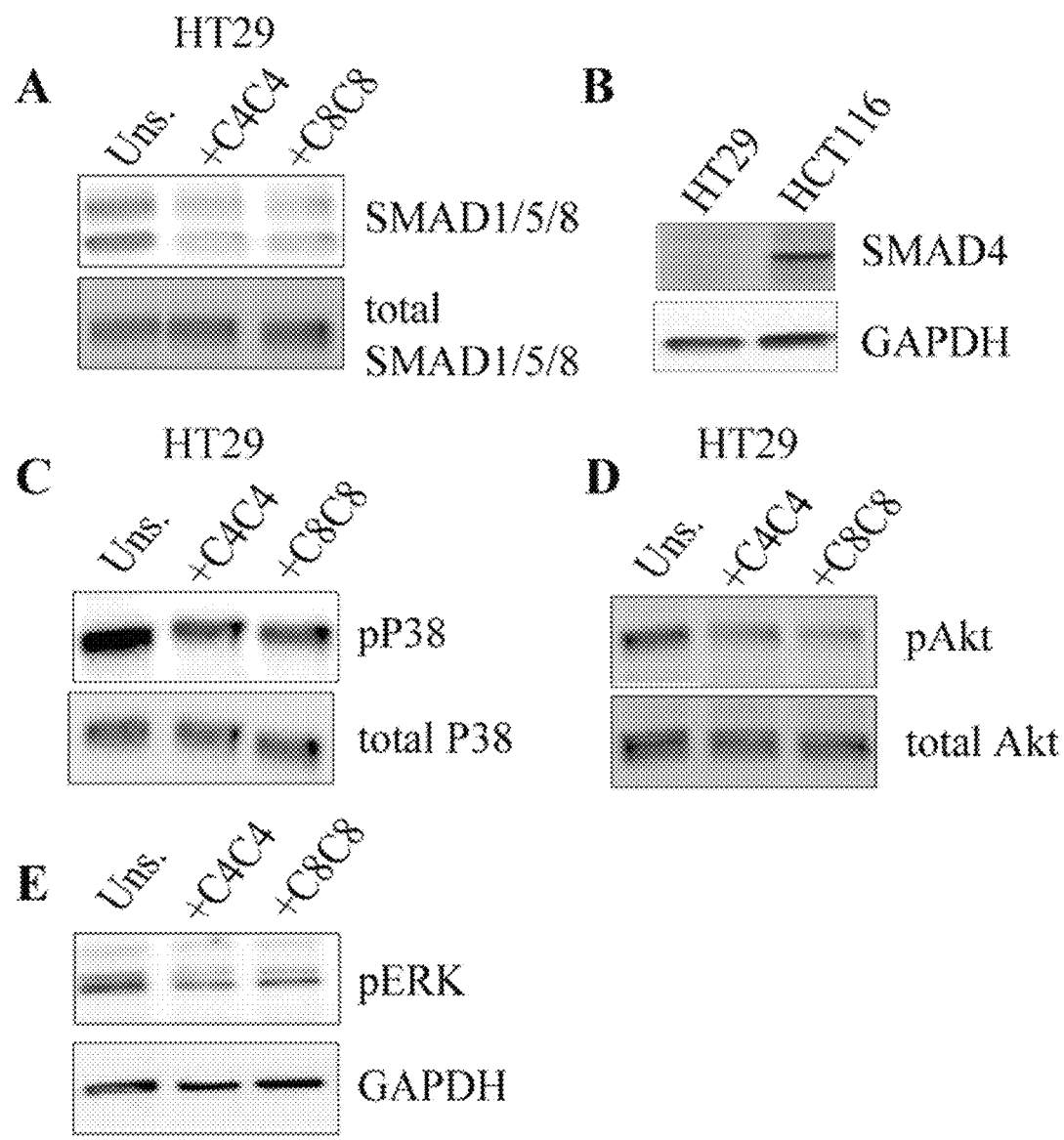
FIG. 29(A-E) shows that single chain antibodies (VHHs) of the invention inhibit non-canonical signals in a colorectal SMAD4-cell line.

As SMAD-independent signaling has been shown to mediate BMP-induced chemoresistance we next studied whether the VHHs would inhibit non-canonical BMP4 signals in HT29 cells. FIG. 29 shows that C4C4 and C8C8 inhibit the phosphorylation of the kinases p38, Akt as well as ERK. As HT29 cells harbour mutations in the SMAD4 gene and therefore do not express SMAD4 protein (FIG. 29B), the SMAD pathway is inactive in these cells and therefore the inhibition of pSMAD by the VHHs has no functional consequences (FIG. 29F). Together, these results show that the VHHs increase chemosensitivity of HT29 cells through the inhibition of non-canonical BMP4 signals.

Western Blot for Non-Canonical Pathways

HT29 cells were starved overnight and treated with the VHHs or Noggin at a concentration of 500 ng/ml for 1 hour. Protein isolation and SDS-PAGE separation were performed next. HT29 were lysed with 100 μl of M-PER buffer (Sigma-Aldrich). Cell debris were pelleted and supernatant was collected. For protein detection the following antibodies were used: antiphospho-SMAD1/5/8 at 1:500; p-p38 (T180/Y182) at 1:500, pAkt (ser473) at 1:1000, total Akt at 1:500, total p38 at 1:500; (Cell Signalling); anti-SMAD4 at 1:500, anti-pERK (Y204) at 1:1000 (Santa Cruz); anti-GAPDH at 1:500 (Millipore).

Figure 30:
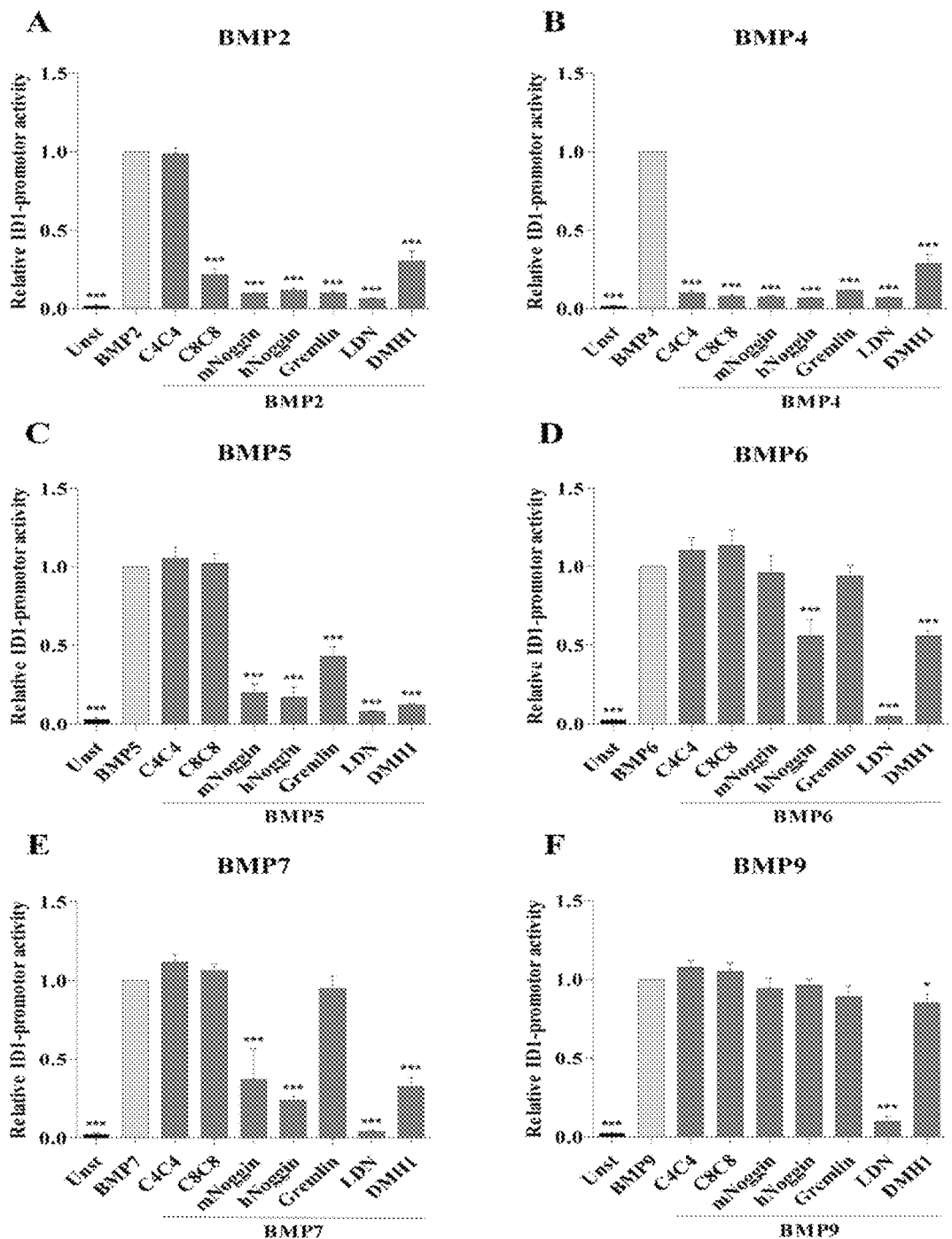
FIG. 30(A-H) shows comparison of specificity between antibodies of the invention and commercially available antibodies and other inhibitors. C2C12 cells were activated with 50 ng/ml of hBMP2 (FIG. 30A), 10 ng/ml of hBMP4 (FIG. 30B), 200 ng/ml of hBMP5 (FIG. 30C), 50 ng/ml of hBMP6 (FIG. 30D), 200 ng/ml of hBMP7 (FIG. 30E), 25 ng/ml of hBMP9 (FIG. 30F), 25 ng/ml of hBMP10 (FIG. 30G) and 50 ng/ml of hBMP12 (FIG. 30H) for 16 h. At the same time the inhibitors were added. VHH, mNoggin, hNoggin and Gremlin were added at a concentration of 500 ng/ml; LDN-193189 (LDN) at 0.5 µM and DMH1 at 0.2 µM.
Figure 30:
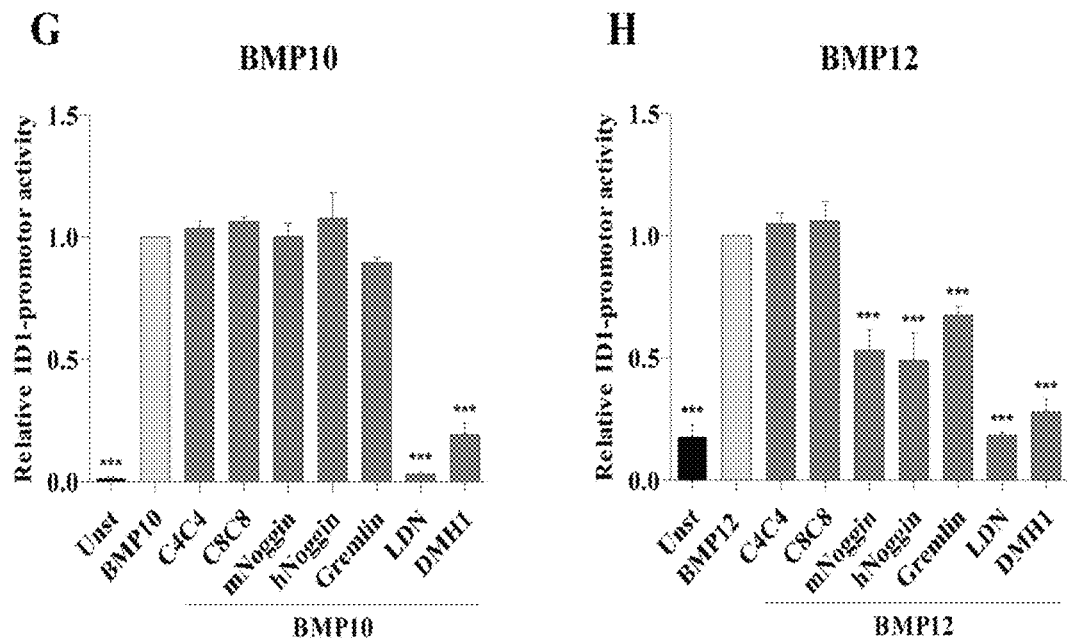
Figure 32:
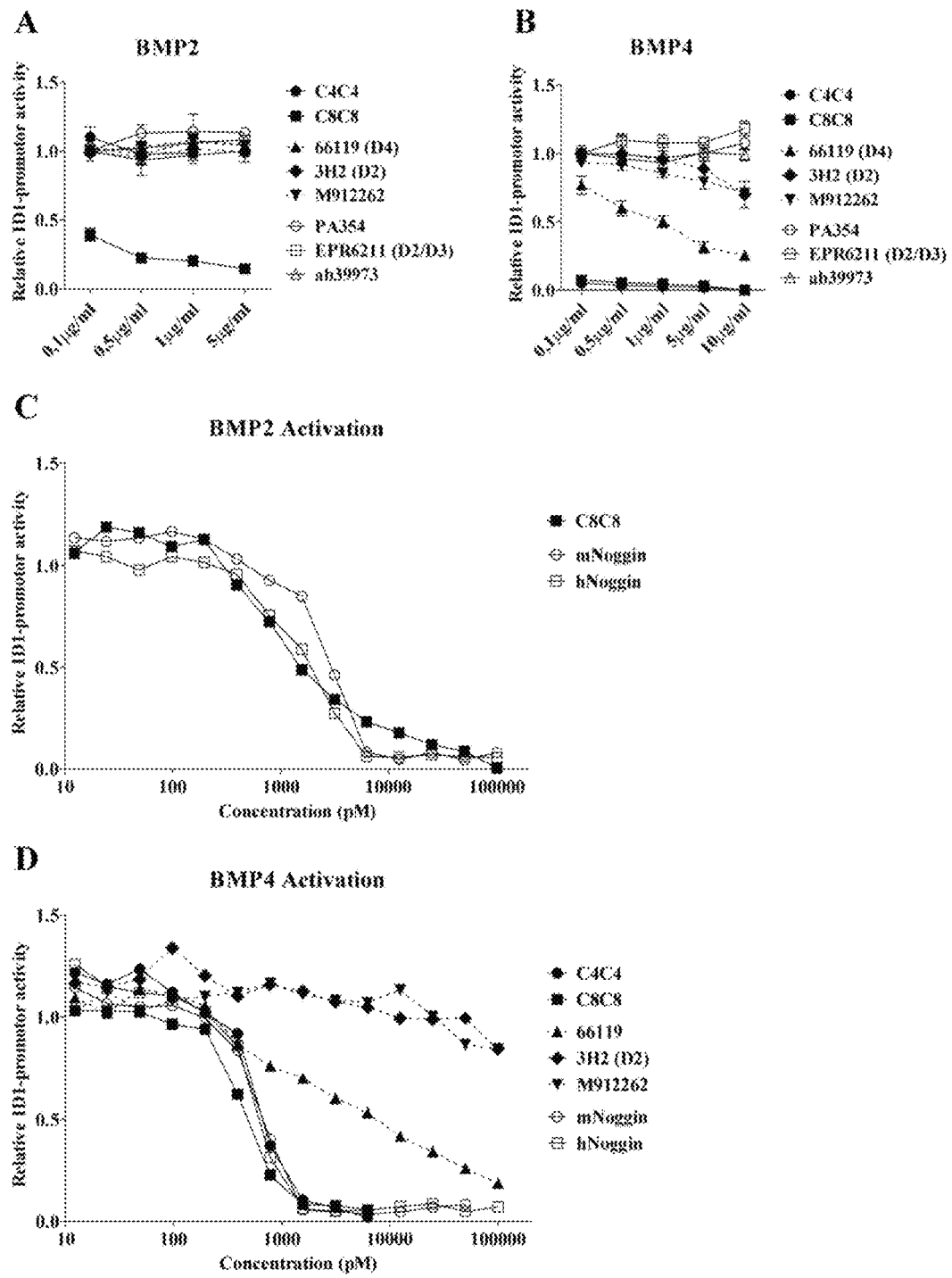
FIG. 32(A-D) shows the efficacy of VHH of the invention compared to different available inhibitors. C2C12 cells were stimulated with 10 ng/ml of hBMP4 (FIG. 32A) or 50 ng/ml of BMP2 (FIG. 32B), and at the same time increasing concentrations of anti-BMP4 antibodies and VHHs were added (0.1 µg/ml to 5 µg/ml). IC50 curves of inhibition of BMP2-mediated signals by C8C8 and natural antagonists (FIG. 32C). IC50 curves of the inhibition of BMP4-mediated signals by VHHs, commercial anti-BMP4 antibodies and natural antagonists (FIG. 32D). Results are represented by the mean of relative ID-1 promoter activity from three independent experiments with experimental triplicates each. Error bars represent the standard error of the mean.

Example 16: Comparative Example Between Antibodies of the Invention and Available Antibodies and Inhibitors Compared to Noggin, C4C4 and C8C8 exhibit increased specificity, as they only bind to BMP4 or BMP2 and 4, respectively. We wanted to determine whether this superiority would also extend to other natural antagonists as well as chemical inhibitors of BMP receptors. Therefore, we compared these two VHHs with two natural antagonists, noggin and gremlin, and two chemical inhibitors, LDN and DMH1, using a BMP response element (BRE)-luciferase reporter assay. In this assay, the activation of the BMP-SMAD dependent response gene ID1 was measured in luciferase reporter C2C12 myoblast cells. As expected, the results shown in FIG. 30 confirm that specificity of C4C4 is restricted to BMP4 and of C8C8 to BMP2 and BMP4. In contrast, the other inhibitors are less selective. For instance, Noggin and Gremlin could greatly inhibit BMP-2, BMP-4 and BMP5 signals. Further, Noggin inhibited BMP-6, BMP-7 and BMP12-mediated SMAD pathways. The chemical inhibitors LDN and DMH1 were proven to be even less selective than Noggin, as they were also shown to inhibit BMP-9 and BMP-10-derived signals. At the concentrations tested, all the inhibitors were equally potent at inhibiting BMP4-derived signals. These results confirm that C4C4 and C8C8 are more specific than current BMP antagonists, being able to neutralize only BMP4 or BMP2/BMP4-mediated SMAD signaling, without affecting the signaling of other BMPs. Next, we compared the inhibition capabilities of our VHHs with several anti-BMP4 antibodies (FIG. 32). For this purpose several anti-BMP4 antibodies were used. For instance, clone EPR6211 (from Chemicon/Millipore) has been used to check expression in NT2/D1 teratocarcinoma cells (Kwak et al 2014) and in adult rat vaginas (Bhattacherjee et al., 2013). Other antibodies have been used for both research applications as well as functional experiments. For instance, clone 66119 (from Santa Cruz, R&D, and Abcam) has been used to check the expression of BMP4 on the murine BM stroma-derived cell line ST2 (Khurana et al 2014) and to inhibit BMP4-mediated smooth muscle cell proliferation. Another anti-BMP4, clone 3H2, was able to inhibit BMP4 mediated glial differentiation (Bhattacherjee et al., 2013). Surprisingly, the concentrations at which those antibodies were used in those and in other publications (Jeanpierre et al 2008, and Hue et al 2006) range between 1-10 μg/ml, in stark contrast to the nanomolar range of which the VHH of the invention were shown to be biologically active. To test whether these disparities are not due to differences in experimental conditions, we compared the activity of C4C4 and C8C8 with current anti-BMP4 antibodies in the luciferase C2C12 system. We compared several antibodies described in the art. Their catalog numbers as well as their clone name can be seen in Table 5. Most of these clones available from different companies.

TABLE 5

List of antibodies used for the comparison with the VHHs

| Clone | Isotype | Company | Catalog number |
|---|---|---|---|
| 3H2 | Mouse Monoclonal IgG2b | Prepotech[1] | 500-M121 |
| | | Millipore | MAB1049 |
| | | Santa Cruz | sc-12721 |
| EPR6211 | Rabbit monoclonal | Millipore[1,2] | MABD188 |
| | | abcam | ab124715 |
| 66119 | Mouse Monoclonal IgG2b | abcam | ab6296 |
| | | GeneTex | GTX26296 |
| | | GeneWay | GWB-41AEF0 |
| | | RandD/Novus[3] | MAB757 |
| | | Santa Cruz | sc-73536 |
| PA354-16.1.1 | Mouse Monoclonal IgG2ak | Millipore | MABD411 |
| ab39973 | Rabbit polyclonal | abcam | ab39973 |
| M912262 | Mouse Monoclonal IgG2b | Antibodies online | ABIN934071 |
| | | Biosource | MBS531999 |
| | | Fitgerald | 10R-B1193 |

[1]described in Bhattacherjee, A.et al. (2013). J. Neurosci. Off. J. Soc. Neurosci. 33, 1050-1061a.
[2]described in Kwak, Y.-D. et al(2014) Biochem. Biophys. Res. Commun. 447, 394-399.
[3]described in Khurana, S.et al. (2014) Stem Cells Dayt. Ohio 32, 3012-3022.

These experiments confirmed that these commercial antibodies do not bind to BMP2, as only C8C8 inhibited BMP2-mediated signals (FIG. 32A). Exceptionally, at concentrations of 100 ng/ml, both VHHs completely inhibited BMP4-specific signals, whereas clone 66119 and 3H2 were only able to inhibit 30% and 1% of the BMP4-specific signal, respectively. Clone M912262 was also very weak at inhibiting BMp4-mediated signals. Surprisingly, three anti-BMP4s antibodies were unable to inhibit the BMP4 signals even at high concentrations of 10 μg/ml (FIG. 32B). The superiority in functionality of the VHHs is also maintained at the molarity level, as shown by the IC50 curves of these antibodies (FIG. 32C). Remarkably, the neutralization activities of C4C4 for BMP4 (IC50=~600 pM) and C8C8 for BMP4 (IC50~450 pM) and BMP2 (IC50=1205 pM) are similar to those of mouse (BMP4 IC50~615 pM; BMP2 IC50~2500 pM) and human Noggin (BMP4 IC50~540 pM and BMP2 IC50~1600 pM) (FIG. 32C and FIG. 32D). These results establish C4C4 and C8C8 as highly effective inhibitors with higher neutralization capabilities as compared to current anti-BMP4 antibodies.

Luciferase Assay

C2C12 cells were cultured in 96-well plates at 5×103 cells/well. After overnight attachment cells were stimulated with 10 ng/ml hBMP4 (Cat No. 314-BP-020; R&D Systems), 50 ng/ml hBMP2 (Cat No. 355-BM-010; R&D Systems), 200 ng/ml hBMP5 (Cat No. 615-BMC-020; R&D Systems), 50 ng/ml hBMP6 (Cat No. 506-BP-020; R&D Systems), 200 ng/ml hBMP7 (Cat No. 354-BP-010; R&D Systems), 25 ng/ml hBMP9 (Cat No. 3209-BP-010; R&D Systems), 25 ng/ml hBMP10 (Cat No. 2926-BP-025; R&D Systems), 50 ng/ml hBMP12 (Cat No. 779-G7-010; R&D Systems) and with or without VHH antibodies: C4C4 and C8C8 at 500 ng/ml; natural antagonist: mNoggin (Cat No. 1967-NG-025; R&D Systems), hNoggin (Cat No. 6057-NG; R&D Systems) and mGremlin (cat#956-GR-050; R&D Systems) at 500 ng/ml; chemical antagonist: 0.5 µM LDN-193189 (Cat No. 11802; Cayman Chemical) and 0.2 µM DMH1 (Cat No. 57146; Selleckchem).

VHH efficacy was evaluated by stimulating cells with 10 ng/ml of hBMP4 and 50 ng/ml of hBMP2, with and without increase concentrations (from 0.1-10 µg/ml) of VHH and anti-BMP4 antibodies: clone 66119, clone 3H2, clone M912262, clone PA354-16.1.1, Clone EPR6211, and anti-BMP4 (ab39973). To determine and compare the IC50 of each antibody, cells were stimulated with 10 ng/ml of hBMP4 or 50 ng/ml of hBMP2, with and without increased molar concentrations (from 0.048-100000 pM) of VHH of the invention, anti-BMP4 antibodies (clone 66119, clone 3H2 and clone M912262) and natural antagonist (mNoggin, and hNoggin). Unstimulated cells were used as controls and wells with no cells used to normalize the background activity. Each condition were treated in triplicate with the different conditions for 16 hours and afterwards luciferase activity was measured by adding 100 µl of luciferase substrate (Bright-Glo™ Luciferase assay System, Promega Benelux, Leiden, The Netherlands). After an incubation period of 5 min, luciferase activity was measured using Synergy HT Multi-Mode Microplate Reader (Biotek, Winooski, Vt., United States). Data was normalized and represented as ratio to the activity of cells stimulated with only BMP.

Figure 33:
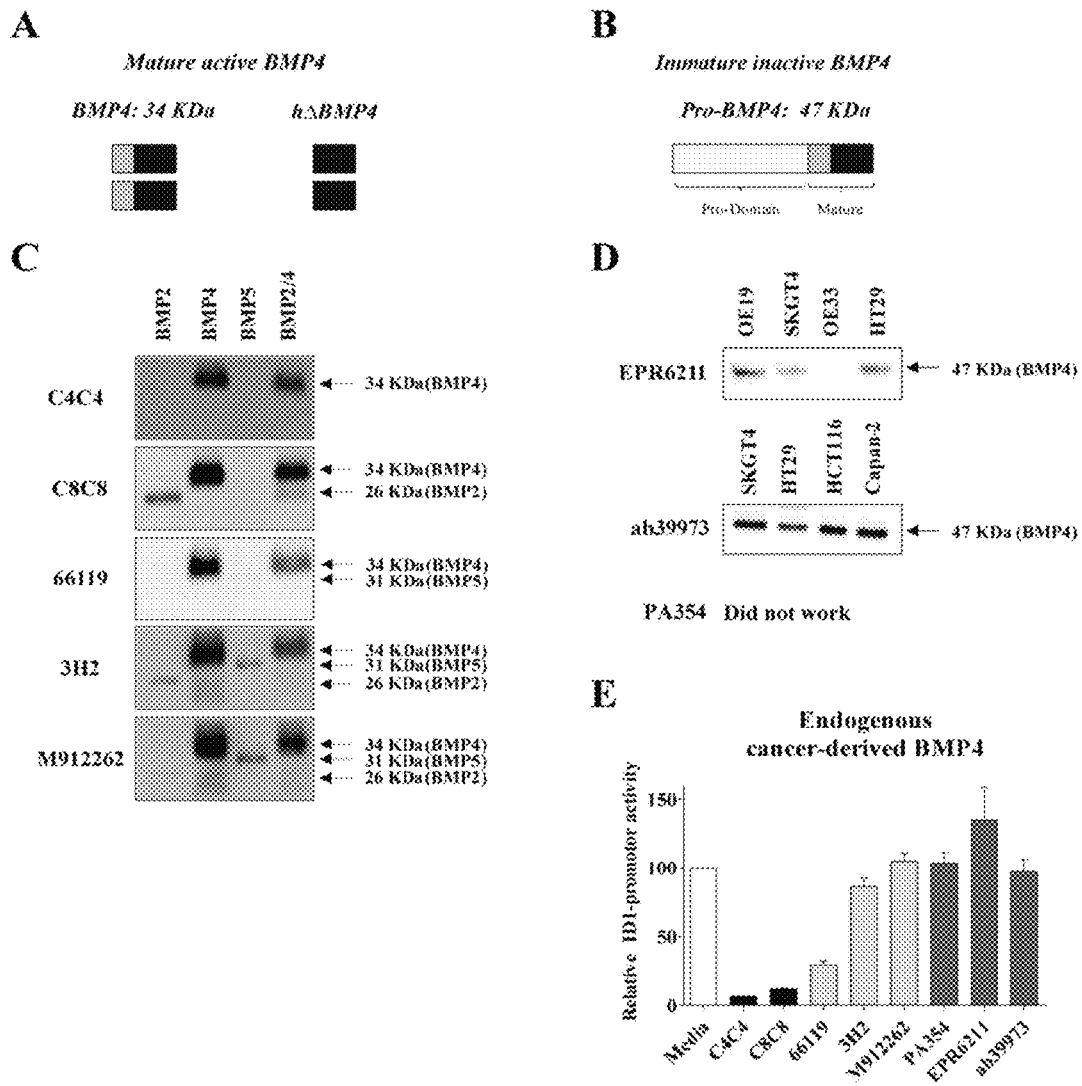
FIG. 33(A-D): BMP4 epitope mapping. Schematic representation of mature active BMP4: complete mature active BMP4 dimer and BMP4 dimer mutant lacking the heparin domain (ΔBMP4) (FIG. 33A).) Schematic representation of immature inactive pro-BMP4 form (FIG. 33B). Western Blot detection of unreduced mature recombinant BMP proteins (FIG. 33C) and reduced cancer cell lines lysates (FIG. 33D). Conditioned media from HT29 was added to the C2C12 cells in the presence of 10 µg/ml of VHHs or anti-BMP4 antibodies (clone 66119, clone 3H2, clone PA354, clone and EPR6211 and antibody ab39973) (FIG. 33E).
Figure 34:
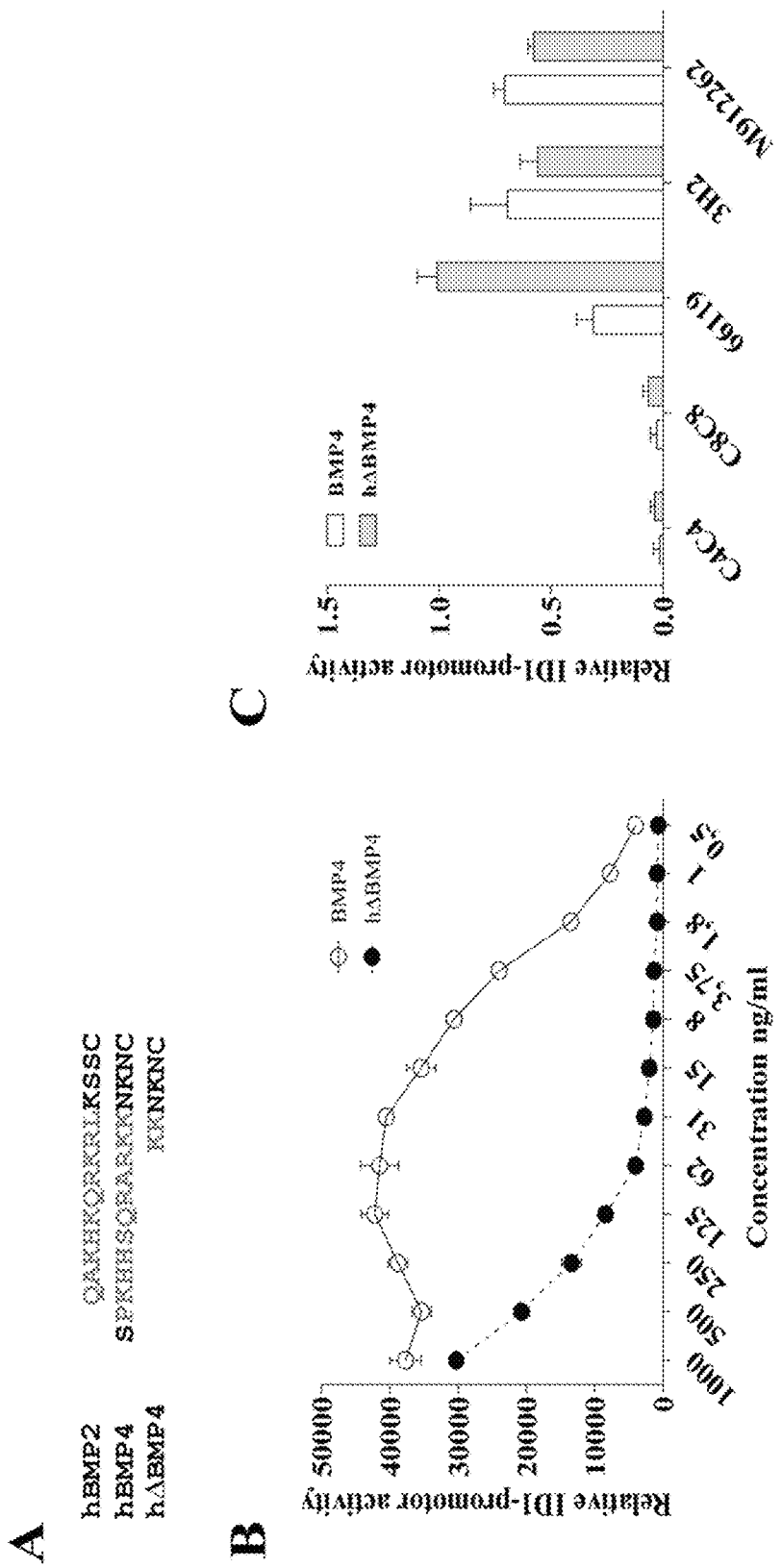
FIG. 34: Schematic alignment of hBMP2, hBMP4 and mutated BMP4 (hΔBMP4) (FIG. 34C A). Comparison of relative ID-1 promoter activity of BMP4 and hΔBMP4 (FIG. 34C B). Comparison of inhibition of wt or mutant BMP4 (HΔBMP4) by the VHHs or the different anti-BMP4 antibodies analyzed using the C2C12 system. Cells were stimulated with 10 µg/ml of VHHs and anti-BMP4 antibodies (clone 66119, clone 3H2 and M912262) (FIG. 34C).

Example 17: Epitope Mapping of the VHHs in Comparison to Current Anti-BMP4 Antibodies
Epitope Mapping of the VHHs in Comparison to Current Anti-BMP4 Antibodies We have compared epitopes recognized by several available anti-BMP4 antibodies with epitopes recognized by antibodies of the invention. FIG. 33 and FIG. 34 show epitope mapping of several commercial anti-BMP4 antibodies. From the previous experiments described above, we concluded that three different types of anti-BMP4 antibodies exist those that are functionally inactive, those that weakly inhibit BMP4 BRE-signals and those that strongly inhibit BMP4 BRE-signals. These results could be explained by differences in epitope binding.

The active mature form of BMP4 (FIG. 33A) results from proteolytic cleavage from a secreted inactive form (pro-BMP4) (FIG. 33B). As only the active dimeric form of BMP4 is used in the C2C12 luciferase-based assays, it is likely that the lack of activity of some antibodies would be due to binding to pro-BMP4 rather than the active dimeric form. Indeed, when the mature dimers of BMP4 were immobilized in nitrocellulose membranes, they were not recognized by the functionally neutral antibodies. In contrast, all the antibodies with functional activity, detected a band of ~34 KDa, which corresponds to the mature BMP4 dimer (FIG. 33B). In these blots, C8C8 also identified dimers of BMP2 (band at ~26 KDa28 KDa, FIG. 33B). Surprisingly clones M9122623 and 3H2H2, also seemed to recognize BMP2 and BMP5. There was also a weak BMP5 band observed when the clone 66119 was used. To confirm that indeed the inactive antibodies bind to the long pro-BMP4 but not the mature BMP4, lysates of different cancer cell lines were blotted with those antibodies (FIG. 33C). A single line of about of ~47 KDa, corresponding to the reduced pro-BMP4, was observed. These results explain why these antibodies do not directly inhibit the signals of the active form of BMP4 in the C2C12 experimental setting. It could be postulated that blocking the inactive form of BMP4 indirectly results in a decreased BMP4 activity, because of blocking its cleavage into an active BMP4. To test whether that is the case or not, we incubated the supernatants of the colorectal cancer cell line HT29, known to produce and secrete BMP4, with the different antibodies. Addition of the antibodies that target pro-BMP4 had no effect on total BMP signal, indicating that these antibodies bind to a region within the pro-domain that does not interfere with proteolitic cleavage. Therefore these antibodies do not affect BMP4 function and their biological significance is limited. The other anti-BMP4 antibodies inhibited endogenous BMP4 activity at different levels (FIG. 33D).

C4C4 and C8C8 target different areas of the BMP4 molecular interface that binds BMPR1a. We therefore wanted to test whether the superiority of the VHHs over the weak commercial anti-BMP4 antibodies was due to the specific targeting of the BMPR1 areas, as opposed to targeting other regions within the mature dimer. To that end, we used a mutated form of BMP4 (FIGS. 33A and 34A), that lacks an N-terminal region containing several basic residues known to be involved in binding to the extracellular matrix through interactions with heparin. Using the C2C12 system, this mutated BMP4 (HΔBMP4) was shown to be less active in activating BMP4-mediated ID1 promoter activity than the full length mature dimer of BMP4 (FIG. 34B). The VHHs efficiently inhibited HΔBMP4-mediated activity, indicating that deletion of this region had no effect on binding of the VHHs to their epitopes on BMP4 (FIG. 34C). In contrast, deletion of the N-terminal part had an effect on the binding of the other antibodies to BMP4 (FIG. 34C). Clone 66119, for instance, was unable to inhibit HΔ-BMP4 mediated signals, demonstrating that the deleted region is indeed the epitope of this antibody. Interestingly, 3H2 and M912262 were able to inhibit HΔBMP4-mediated signals better than BMP4, indicating that this N-terminal domain negatively interferes with their epitope (FIG. 34C).

Figure 31:
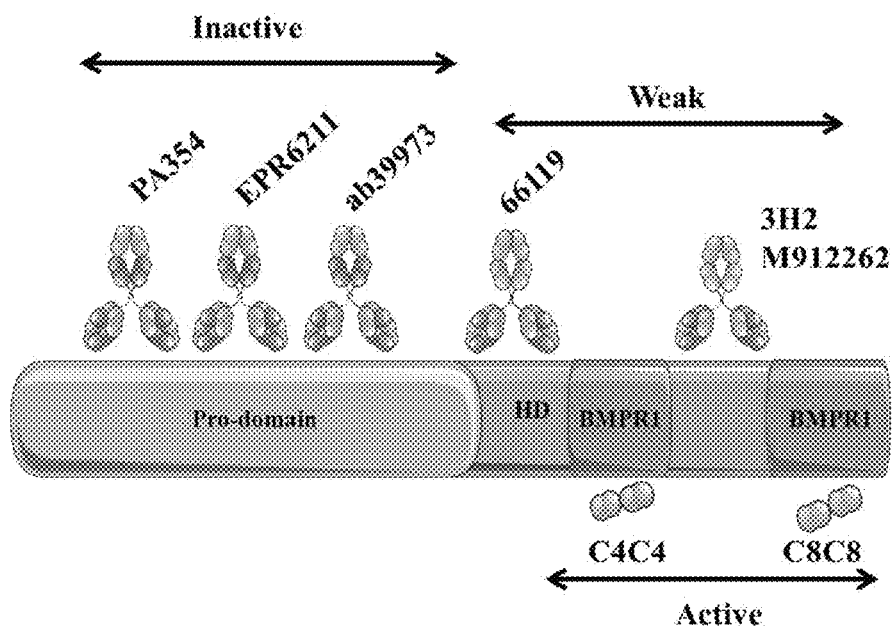
FIG. 31 shows a representation of different epitopes of commercially available anti-BMP4 antibodies and VHHs. Available anti-BMP4 antibodies engage their target via interactions through different domains within BMP4. Whereas C4C4 and C8C8 bind to the BMPR1a binding site, inactive antibodies bind to the prodomain and weak antibodies to certain regions of the mature protein, such as the heparin domain (HD).

Our study has revealed three types of anti-BMP4 antibodies (FIG. 31). We show that antibodies that recognize pro-BMP4 are uncapable of inhibiting BM P4 function. First, they cannot directly inhibit the functional activity of mature BMP4 as they do not bind to this active form. And second their binding to pro-BMP4 does not affect its cleavage and therefore its released into the active form, therefore the BMP4 activity in the system remains unchanged.

We have further shown that anti-BMP4 antibodies that do not bind to the BMPR1a binding site of BMP4 have only weak inhibitory capabilities. Using western blot we found that all the antibodies in this group bind the mature region of BMP4. In particular, and as confirmed in previous results, clone 66119 binds to an N-terminal region of BMP4 that might correspond to the heparin domain of BMP4. Here, we prove that this antibody is remarkably less effective at inhibiting BMP4-mediated function than the VHHs of the invention. The other anti-BMP4 antibodies of this group, not only were extremely poor at functionally inhibiting BMP4 but they bound other BMPs, such as BMP2 and BMP5. This indicates that their epitope lies within a region containing residues shared by these BMPs. Because they bind other BMPs, this demonstrates that their epitope does not overlap with that of the antibodies of the invention. Together, these results show that the antibodies in this group, bind to a region within the mature BMP4 that is functionally irrelevant and that does not correspond to the BMPR1 binding region. Indeed, the finding that HΔBMP4 is still able to activate (albeit at much lesser concentrations) the ID1 promoter in C2C12 cells, suggests that complete removal of this region is not sufficient to block the ability of BMP4 to activate its receptors. Further, we also explored the low biological significance of these antibodies. When using a colorectal cancer cell line that exclusively secretes BMP4, we found that using a saturating amount of the commercially available antibodies does not inhibit BMP4-mediated signals.

The third group of antibodies tested, includes C4C4 and C8C8. These are llama-derived antibodies raised against human BMP4 that binds to the BMPR1 epitope of BMP4 with high affinity. The results herein show that these antibodies are superior both in specificity as well as effectiveness. To our knowledge, these are the first anti-BMP4 antibodies described to target the BMPR1-binding region of BMP4. Without wishing to be bound by theory, we therefore postulate that targeting BMP4 areas involved with BMPR1 binding, confers functional superiority to the anti-BMP4 antibodies, as opposed to targeting other areas within the mature dimeric form of BMP4.

Cells and Cell Culture

Stably transfected C2C12 mouse myoblasts with BRE-luciferase vector containing mouse ID1 promoter (BMP Responsive Element) were kindly donated by Dr. L. Zilberberg and Dr. D. Rifkin (27). C2C12 cells were culture in Dulbecco's Modified Eagle Medium (DMEM) supplemented with 10% of Fetal Bovine Serum (FBS), 2 mM of glutamine, 100 units/ml of penicillin, 100 µg/ml of streptomycin and 70014/ml of G418 (InvivoGen SAS, Toulouse, France).

Esophageal adenocarcinoma cell line 0E19, 0E33 and SKGT4 and colorectal adenocarcinoma cell line HT29 were culture in Roswell Park Memorial Institute 1640 medium (RPMI) supplemented with 10% FBS, 2 mM of glutamine, 100 units/ml of penicillin and 100 µg/ml of streptomycin. Colorectal adenocarcinoma cell line HCT116 and pancreas adenocarcinoma cell line Capan-2 were culture in DMEM supplemented with 10% FBS, 2 mM of glutamine, 100 units/ml of penicillin and 100 µg/ml of streptomycin. All carcinoma cell lines were culture for at least 4 days, were the medium was change every 2 to 3 days.

Western Blotting

To determine the different forms of BMP4, recombinant proteins and carcinoma cell lines lysate were used. Protein concentrations of cell lysates were determined using Pierce™ BCA Protein Assay Kit (Pierce Biotechnology, Rockford, Ill. USA), following the manufacturer's protocol. Equal amount of sample were loaded (between 8 and 30 µg/lane) on a 10% SDS-polyacrylamide gel and subsequently blotted onto PVDF transfer membranes. The membranes were blocked with blocking solution (5% Nonfat-milk+Tris-Buffered Saline with Tween®-20 (TBST) or 5% bovine serum albumin (BSA)+TBST) and subsequently incubated with the appropriate primary antibody and secondary antibody. Afterwards, membranes were washed and incubate with chemiluminescent solution (Pierce™ ECL subtract, Pierce Biotechnology, Rockford, Ill. USA) and visualized using ImageQuant LAS 4000 (GE Healthcare Life Science). Densitometry analysis was performed using Image J 1.45s (Wayne Rasband, National Institutes of Health, USA). Primary antibodies include: anti-BMP4 clone 66119 (1 µg/ml; Cat. No. MAB757; R&D Systems), anti-BMP4 clone 3H2 (0.5 µg/ml; Cat. No. 500-M121; Peprotech); anti-BMP4 clone M912262 (0.5 µg/ml; Cat No. ABIN934071; Antibodies-Online), anti-BMP4 Clone EPR6211 (0.1 µg/ml; Cat. No. ab124715; Abcam), anti-BMP4 (0.8 µg/ml; Cat No. ab39973; Abcam), C4C4 (0.1 µg/ml) and C8C8 (0.1 µg/ml). Secondary antibodies include: HRP-anti-rabbit (1:200; Cat No. P0448; Dako), HRP-anti-mouse (1:2000; Cat No. P0447; Dako) and HRP-anti-llama (1:1000; Cat No. ab112786; Abcam).

Luciferase Assays

To check the activity of the ID1 promoter of different forms of BMP4, cells were cultured with increased concentrations (from 0.5-1000 ng/ml) of BMP4 and the mutated form of BMP4 (HΔBMP4). Also, the superiority of the VHH target sites compared with the different anti-BMP4 antibodies were ascertained by stimulating the cells with the different BMP4, mutated and unmutated BMP4, with and without 10 µg/ml of VHHs and anti-BMP4 antibodies: clone 66119, clone 3H2 and clone M912262. Analysis of the different antibodies in the binding of endogenous BMP4 was performed by stimulated C2C12 cells with conditioned medium of HT-29 cell line with and without 10 µg/ml of VHHs and anti-BMP4 antibodies: clone 66119, clone 3H2, clone PA354-16.1.1, clone EPR6211 and Abcam antibodies ab39973.

All experiments were performed for a final volume of 1001 of DMEM supplemented with 0.1% BSA, 2 mM of glutamine, 100 units/ml of penicillin and 100 µg/ml of streptomycin, in each well. Unstimulated cells were used as controls and wells with no cells used to normalize the background activity. Each condition were treated in triplicate for 16 hours and afterwards luciferase activity was measured by adding 1001.11 of luciferase substrate (Bright-Glo™ Luciferase assay System, Promega Benelux, Leiden, The Netherlands). After an incubation period of 5 min, luciferase activity was measured using Synergy HT Multi-Mode Microplate Reader (Biotek, Winooski, Vt., United States). Data was normalized and represented as ratio to the activity of cells stimulated with only BMP.

Statistical Analysis

All experimental data were carried out with at least three independent experiments. Data is expressed as mean±standard error mean (SEM). Statistical analysis was analysed using one-way analysis of variance (ANOVA) followed by Dunnett's multiple comparison test. Probabilities of $p \leq 0.05$ (*), $p \leq 0.01$ () and $p \leq 0.001$ (*) were considered to be statically significant. Statistical analysis was performed using Graph Pad Prism 5.01 (Graph Pad Software, Inc., CA USA)

Example 18 In Vivo Treatment of SMAD4 Negative Cancer Using C4C4 and C8C8 Anti BMP4 and Anti BMP2 and 4 Antibodies In vitro experiments proved that C4C4 and C8C8 together with different types of chemotherapeutics have a synergistic effect on tumor cell growth. To test the therapeutic and synergistic effects of C4C4 and C8C8 with chemotherapy in vivo the following experiment was performed:

An esophageal adenocarinoma human cancer cell line, ISO76-A, derived from a PDX of a patient cancer biopsy using a method as recently described (Read M, Liu D, Duong C P, et al. Intramuscular transplantation improves engraftment rates for esophageal patient-derived tumor xenografts. Ann Surg Oncol 2015. Published Online First 18 Feb. 2015. doi:10.1245/s10434-015-4425-3) was used for this experiment. The ISO76-A cell line was found to carry a SMAD4 mutation. Thirty female NOD scid gamma (NSG) mice aged 6 to 8 weeks were inoculated with the ISO76-A human esophageal cancer cell line randomized into six groups of 5 mice each. Each mouse was inoculated subcutaneously with the ISO76-A tumour cells. Cells were prepared in 50%:50% Matrigel:PBS mix and injected subcutaneously into the right flank of the NSG mice, (2.5×10^6 cells/mice in 100 uL suspension). Once tumours reached a volume of >80 mm3 treatments were initiated. Before treatment animals were randomized into six groups: group 1 received vehicle (0.9% NaCl saline); Group2 received Cisplatinum 2 mg/kg once per week; Group 3 received daily 100 microgram C4C4 via intraperitoneal injections (IP); Group 4 received daily 100 microgram C8C8 via intraperitoneal injections (IP); Group 5 received Cis-platinum 2 mg/kg once per week in combination with C4C4, 100 microgram daily IP, and Group 6 which received Cisplatinum 2 mg/kg once per week and C8C8 100 microgram daily IP. All formulations were dissolved in saline.

Figure 35:
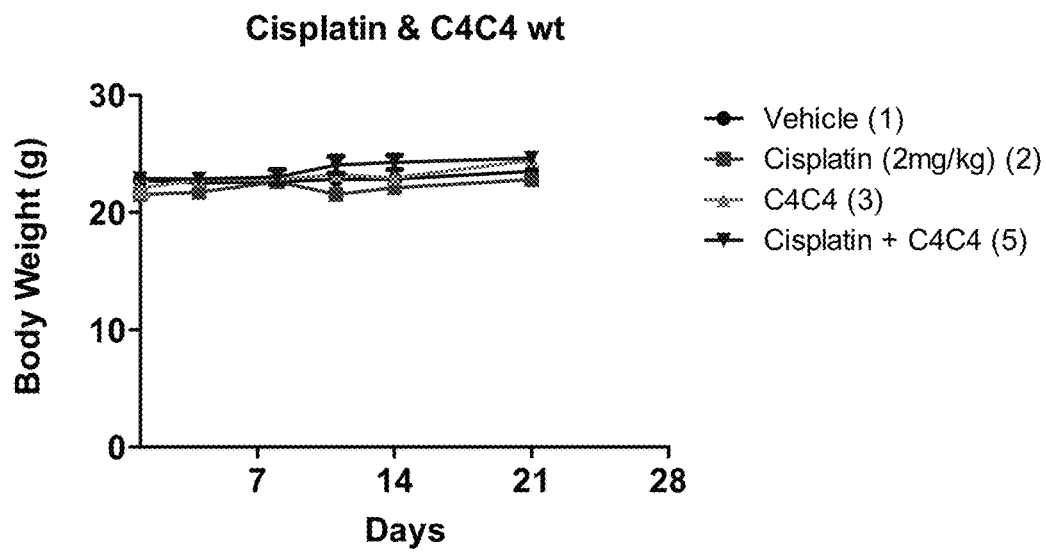
FIG. 35 shows that the animal weights of the animals treated with C4C4 or C4C4 and cis-platinum are comparable to the control group
Figure 36:
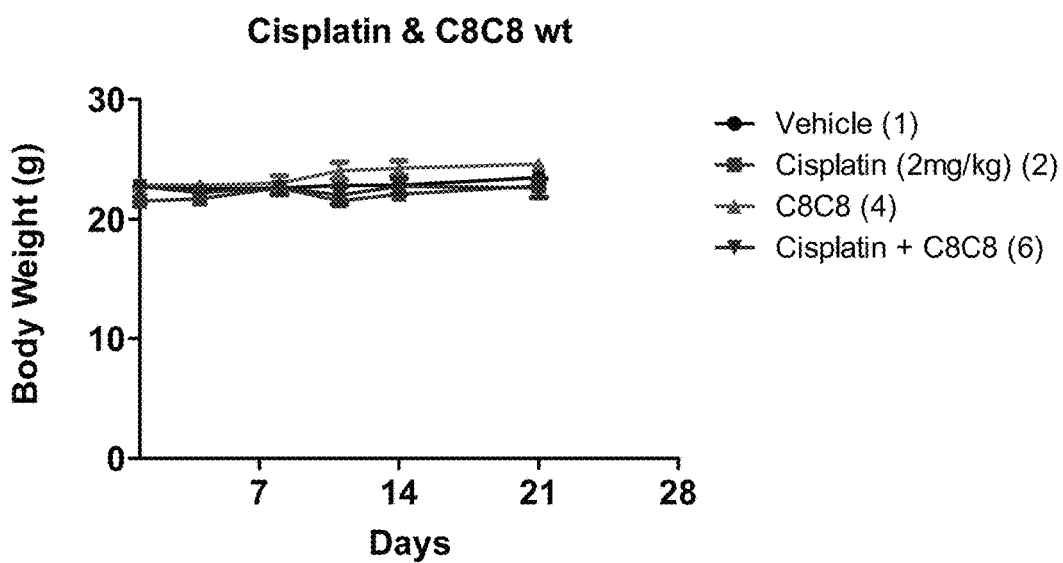
FIG. 36 shows that the animal weights of the animals treated with C8C8 or C8C8 and cis-platinum are comparable to the control group.
Figure 37:
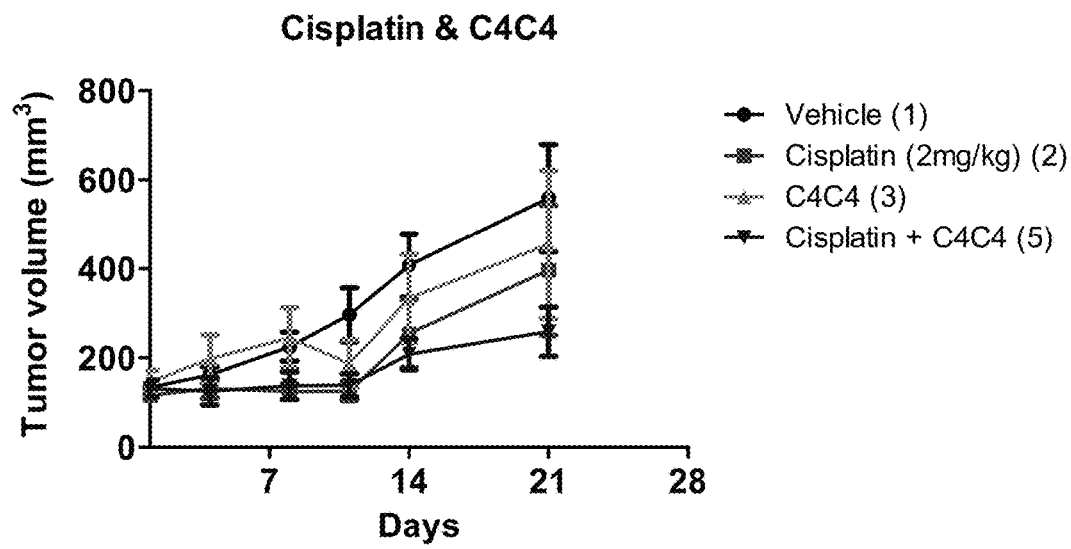
FIG. 37 shows that C4C4 as a single compound has a growth inhibitory effect on the iso76-A cell line in vivo. In combination with cis-platinum C4C4 has a synergistic effect and overcomes chemoresistance.
Figure 38:
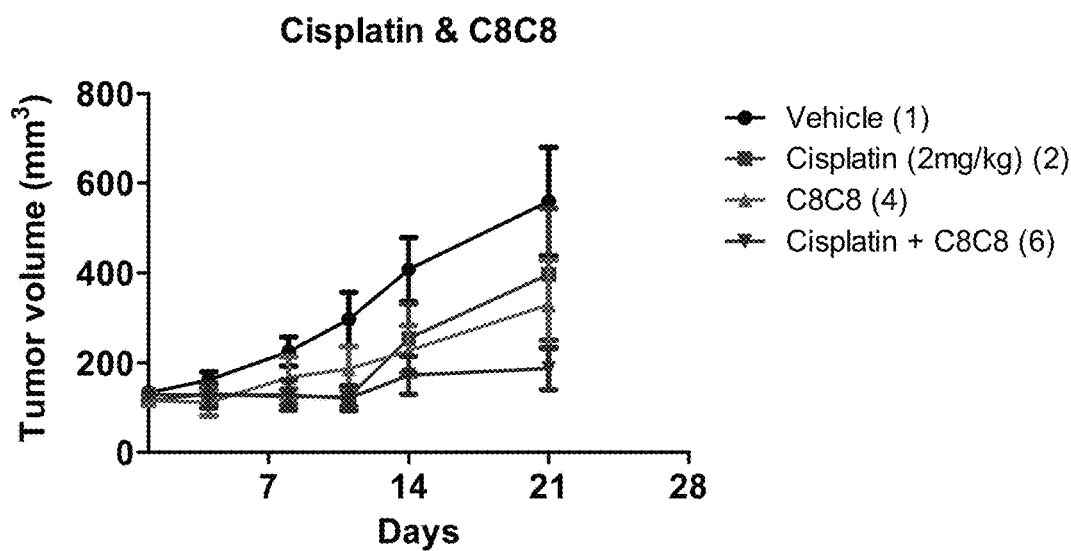
FIG. 38 shows that C8C8 as a single compound has a growth inhibitory effect on the iso76-A cell line in vivo. In combination with cis-platinum C8C8 has a synergistic effect and overcomes chemoresistance.

Tumor growth was monitored biweekly with electronic calipers and animal weight was recorded. FIGS. 35 and 36 show that for all groups the animal weight gain were comparable to that of the control group indicating that the compounds have no negative effect on weight gain in this specific setting. At week 3 (day 21) FIGS. 37 and 38 show that both C4C4 and C8C8 inhibit tumor growth. Both compounds thus synergize with cis-platinum and overcome chemoresistance, which resulted in significant decrease and even stabilization of tumor growth.

The invention claimed is:

1. An antibody that binds BMP4, said antibody comprising:
   a) a heavy chain CDR1 consisting of the amino acid sequence of SEQ ID NO:2,
   b) a heavy chain CDR2 consisting of the amino acid sequence of SEQ ID NO:3, and
   c) a heavy chain CDR3 consisting of the amino acid sequence of SEQ ID NO:4.

2. The antibody of claim 1, said antibody comprising the amino acid sequence of SEQ ID NO:11.

3. An antibody that binds BMP4, consisting of a dimer of the antibody of claim 1.

4. An antibody that binds BMP4, consisting of a dimer of the antibody of claim 2.

5. An antibody that binds BMP4, said antibody comprising:
   a) a heavy chain CDR1 consisting of the amino acid sequence of SEQ ID NO:5,
   b) a heavy chain CDR2 consisting of the amino acid sequence of SEQ ID NO:6, and
   c) a heavy chain CDR3 consisting of the amino acid sequence of SEQ ID NO:7.

6. The antibody of claim 5, said antibody comprising the amino acid sequence of SEQ ID NO:12.

7. An antibody that binds BMP4, consisting of a dimer of the antibody of claim 5.

8. An antibody that binds BMP4, consisting of a dimer of the antibody of claim 6.

9. An antibody that binds BMP4, said antibody comprising:
   a) a heavy chain CDR1 consisting of the amino acid sequence of SEQ ID NO:8,
   b) a heavy chain CDR2 consisting of the amino acid sequence of SEQ ID NO:9, and
   c) a heavy chain CDR3 consisting of the amino acid sequence of SEQ ID NO:10.

10. The antibody of claim 9, said antibody comprising the amino acid sequence of SEQ ID NO:14.

11. An antibody that binds BMP4, consisting of a dimer of the antibody of claim 9.

12. An antibody that binds BMP4, consisting of a dimer of the antibody of claim 10.

* * * * *